(12) United States Patent
Weisleder et al.

(10) Patent No.: US 9,458,465 B2
(45) Date of Patent: *Oct. 4, 2016

(54) COMPOSITIONS AND METHODS TO MODULATE CELL MEMBRANE RESEALING

(75) Inventors: Noah Weisleder, Elizabeth, NJ (US); Chuanxi Cai, Highland Park, NJ (US); Jianjie Ma, Belle Mead, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 1369 days.

This patent is subject to a terminal disclaimer.

(21) Appl. No.: 12/328,646

(22) Filed: Dec. 4, 2008

(65) Prior Publication Data

US 2009/0208473 A1    Aug. 20, 2009

Related U.S. Application Data

(60) Provisional application No. 61/005,410, filed on Dec. 4, 2007.

(51) Int. Cl.
| | |
|---|---|
| *C12N 9/00* | (2006.01) |
| *C12N 5/06* | (2006.01) |
| *A61K 38/53* | (2006.01) |
| *C12N 15/62* | (2006.01) |
| *C07K 14/47* | (2006.01) |

(52) U.S. Cl.
CPC ........... *C12N 15/62* (2013.01); *C07K 14/4716* (2013.01); *C12N 9/93* (2013.01); *A61K 38/53* (2013.01)

(58) Field of Classification Search
CPC ... C07K 14/4702; C12N 15/62; A61K 38/53
USPC ........................................ 435/183; 424/94.1
See application file for complete search history.

(56) References Cited

U.S. PATENT DOCUMENTS

| | | | |
|---|---|---|---|
| 6,943,241 B2 | 9/2005 | Isogai et al. | |
| 7,842,467 B1 * | 11/2010 | Heidbrink et al. | 435/7.1 |
| 8,420,338 B2 | 4/2013 | Weisleder et al. | |
| 2003/0165937 A1 | 9/2003 | Brown et al. | |
| 2003/0216424 A1 | 11/2003 | Davis | |
| 2003/0224464 A1 | 12/2003 | Thompson | |
| 2003/0236392 A1 | 12/2003 | Isogai et al. | |
| 2005/0054832 A1 | 3/2005 | Lazar et al. | |
| 2006/0121496 A1 | 6/2006 | Srivastava et al. | |
| 2007/0015815 A1 | 1/2007 | Deloach | |
| 2007/0020637 A1 | 1/2007 | Isogai et al. | |
| 2007/0123494 A1 | 5/2007 | Seipelt | |
| 2009/0075875 A1 | 3/2009 | Hoffman et al. | |
| 2009/0318348 A1 | 12/2009 | Ma et al. | |
| 2011/0202033 A1 | 8/2011 | Weisleder et al. | |
| 2011/0251256 A1 | 10/2011 | Ko et al. | |
| 2011/0287004 A1 | 11/2011 | Ma et al. | |
| 2011/0287015 A1 | 11/2011 | Ma et al. | |
| 2014/0127211 A1 | 5/2014 | Geles | |

FOREIGN PATENT DOCUMENTS

| | | |
|---|---|---|
| CN | 101797375 B | 1/2013 |
| JP | 2004-357715 | 12/2004 |
| JP | 2003-135075 | 5/2013 |
| WO | WO 2008-054561 | 5/2008 |
| WO | WO 2009/073808 | 6/2009 |
| WO | WO 2011/142744 A1 | 11/2011 |

OTHER PUBLICATIONS

Seffernick et al. J Bacteriol. Apr. 2001; 183 (8): 2405-10.*
Witkowski et al. Biochemistry. Sep. 7, 1999; 38(36): 11643-50.*
File History of 7,981,866.
International Search Report for PCT/US2010/034331, 2010.
Cai et al. JBC, Jun. 5, 2009, v284(23): 15894-902.
Cai et al. Biophysical Journal, 2007, Supplement S, pp. 20A-21A.
Coral-Vazquez, R. et al. Disruption of the sarcoglycan-sarcospan complex in vascular smooth muscle: a novel mechanism for cardiomyopathy and muscular dystrophy. Cell 98, 465-74 (1999).
Doherty, K. R. & McNally, E. M. Repairing the tears: dysferlin in muscle membrane repair. Trends Mol Med 9, 327-30 (2003).
Kudryashova, E., Kudryashov, D., Kramerova, I. & Spencer, M. J. Trim32 is a ubiquitin ligase mutated in limb girdle muscular dystrophy type 2H that binds to skeletal muscle myosin and ubiquitinates actin. J Mol Biol 354, 413-24 (2005).
Miyake, K. & McNeil, P. L. Vesicle accumulation and exocytosis at sites of plasma membrane disruption. J Cell Biol 131, 1737-45 (1995).
Perez-Caballero, D., Hatziioannou, T., Yang, A., Cowan, S. & Bieniasz, P. D. Human tripartite motif 5alpha domains responsible for retrovirus restriction activity and specificity. J Virol 79, 8969-78 (2005).
Reymond et al., May 1, 2001, EMBO J, 20(9): 2140-2151.
Tsutsumi et al. Cardiac-specific expression of caveolin-3 induces endogenous cardiac protection by mimicking cardiac ischemic preconditioninng circulation. Nov. 4, 2008 118(19): 1979-88.
XP002562730: Database Geneseq [Online] Oct. 7, 2004, xP002562730 retrieved from EBI accession No. GSP:ADQ67780.
XP002562731: Database EMBL [Online] Apr. 4, 2006, Oryctolagus cuniculus MG53 mRNA for mitsugumin 53, compiete cds. xP002562731 retrieved from EMBL accession No. EMBL : AB231473.

(Continued)

*Primary Examiner* — Md. Younus Meah
(74) *Attorney, Agent, or Firm* — Bryan D. Zerhusen; Locke Lord LLP

(57) ABSTRACT

Disclosed herein are compositions and methods for repairing cell membranes. In addition, the invention relates to therapeutic compositions comprising nucleotides and/or polypeptides of the invention in combination with a pharmaceutically acceptable carrier, wherein the composition facilitates the repair of cell membranes. Moreover, the invention relates to the treatment and/or prevention of pathological conditions associated with cell membrane damage.

17 Claims, 58 Drawing Sheets

(56) References Cited

OTHER PUBLICATIONS

XP002562732: Database EMBL [Online] Apr. 4, 2006, Mus musculus MG53 mRNA f or mitsugumin 53, complete cds. xP002562732 retrieved from EBI accession No. EMBL : AB231474, AB231473.
Extended European Search Report for EP 08 85 5963.
ISR, Int'l Preliminary Report on Patentability, and Written Opinion of the ISA for PCT/US2008/085573.
International Search Report for PCT/US2007/015815.
*Supplementary European Search Report and Opinion* for: App. No. EP 07 86 7154.2-1212 / 2037737; PCT/US2007/015815.
Short, K. M., and Cox, T.C. Subclassification of the RBCC/TRIM Superfamily Reveals a Novel Motif Necessary for Microtubule Binding. JBC v281(13):8970-80.
Meroni Germana et al: TRIM/RBCC. A novel class of single protein Ring finger E3 ubiquitin Ligases. Bioessays : News and Reviews in Molecular. Cellular and Developmental Biology Nov. 2005, vol. 27, No. 1.1, Nov. 2005, pp. 1147-1157, XP002562734 ISSN:0265-9247.
Bansal Dimple et al:—Dysferlin and the plasma membrane repair in muscular dystrophy. Trends in Cell Biology, vo1. 14, No. 4, Apr. 2004, pp. 206-213, XP002562733 ISSN: 0962-8924.
Cai Chuanxi et al: MG53 regulates membrane budding and exocytosis in muscle cells. The Journal of Biological Chemistry Jan. 30, 2009, vo1 . 284, No. 5, Jan. 30, 2009, pp. 33t4-3322, XP002562735 ISSN: 0021-9258.
Cai Chuanxi et al: MG53 nucleate assembly of cell membrane repair machinery. Nature Cell Biology Jan. 2009, vol. 11, No. L, Jan. 2009, pp. 56-64, XP002562736 ISSN: 1476-4679.
Arnau et al. Current strategies for the use of affinity tags and tag removal for the purification of recombinant proteins. Protein expression and Purification: 48:1-13, 2006 (online publication Dec. 28, 2005).
Bork et al., "Go hunting in sequence databases but watch out for the traps," Trends in Genetics 1996. 12(10): 425-427.
Bork, "Powers and pitfalls in sequence analysis: the 70% hurdle," Genome Res2000. 10: 398-400.
Brenner. "Errors in genome annotation," Trends in Genetics 1999, 15(4): 132-133.
Cao et al. MG53 constitutes a primary determinant of cardiac ischemic preconditioning. Circulation 121: 2565-75. 2010.
Casset et al. Biochemical and Biophysical Research Communications 2003. 307: 198-205.
Chen et al. J Mol Biol. 1999. 293: 865-881.
Cleland et al. A specific molar ratio of stabilizer to protein is required for storage of a lyophilized monoclonal antibody. J Pharmaceutical Sci 2001. 90(3): 310-321.
De Pascalis et al. The Journal of Immunology 2002. 169: 3076-84.
Doerks et al., "Protein annotation: detective work for function prediction," Trends In Genetics. 14(6): 248-250, 1998.
Hoge. "Peptide Antigen Design for Antibody Production". Sigma-Genosys technical sheet. Jul. 31, 2003. 2 pages.
Holm et al. Mol Immunology 2007. 44:1075-1084.
Jia Yanlin et al: Treatment of acute lung injury by targeting MG53-mediated cell membrane repair. Nature Communications 2014. 5:4387. XP002734684; ISSN: 2041-1723.
Juengst. "What next for human gene therapy?" BMJ 2003. 326: 1410-1411.
Lee et al. Molecular Cloning of agonistic and antagonistic monoclonal antibodies against human 4-1BB, Eur J Immunogenet. 29(5): 449-552, 2002.
Liu et al. Cardioprotection of recombinant human MG53 protein in a porcine model of schemia and reperfusion injury. J Mol Cell Cardiol. 80: 10-19, 2015.
MacCaallum et al. J Mol Biol 1996. 262: 732-745.
Murray. "Cloning Genes in Mammalian Cell-lines" in Molecular Biology andBiotechnology. Great Britain: The Royal Society fo Chemistry. 2000, pp. 177-201.

Ngo et al., "Computational complexity, protein structure prediction, and the Levinthal paradox." Computational Complexity Protein Structure Prediction and the Levinthal Paradox, pp. 492-495. 1994.
Novagen pET System Manual; 50 ages; Feb. 1999.
Paul. Fundamental Immunology, 3rd Ed., Raven Press, New York, Chapt. 8, pp. 242, 292-295 (1993).
Phillips. "The challenge of gene therapy and DNA delivery," J Pharm Pharmacology 2001. 53:1169-1174.
"Recombinational Cloning". Current Protocols in Molecular Biology. 2006. John Wiley & Sons, Inc. 3.20.01-3.20-22.
Rubanyi. "The future of human gene therapy," Mol Aspects Med 2001. 22: 113-142.
Rudikoff et al. Proc Natl Acad Sci USA 1982. 79: 1979-83.
Skolnick et al., "From genes to protein structure and function: novel applications of computational approaches in the genomic era," Trends In Biotech 18(1): 34-39, 2000.
Smith et al., "The challenges of genome sequence annotation or 'The devil is in the details'," Nature Biotech 1997. 15: 1222-1223.
Takebe et al. Sralpha promoter: an efficient and versatile mammalian cDNA expression system composed of the simian virus 40 early promoter and the R-U5 segment of human T-cell leukemia virus type 1 long terminal repeat. Mol Cell Biol 1988. 8(1): 466-472.
Takeshima. Genbank Accession No. AB231474; Apr. 4, 2006; 2 total pages.
Takeshima. Genbank Accession No. AB231473; Apr. 4, 2006; 2 total pages.
Takeshima et al., Mitsugumin 29, a novel synaptophysin family member from the triad junction in skeletal muscle. Biochem J 1998. 331: 317-322.
Tamarin. Principles of Genetics. Iowa: Wm. C. Brown Publishers. 1993, pp. 250-252.
Terpe. Overview of tag protein fusions: from molecular and biochemical fundamentals to commercial systems. Appl Microbiol Biotechnol 2003. 60: 523-533.
Tokuriki et al., "Stability effects of mutations and protein evolvability," Curr Opin Structural Bio 2009. 19: 596-604.
Vajdos et al. J Mol Biol 2002. 320: 415-428.
Waddell Leigh B et al. Dysferlin, annexin A1, and mitsugumin 53 are upregulated in muscular dystrophy and localize to longitudinal tubules of the T-system with stretch. Apr. 2011, Journal of Neuropathology & experimental neurology, 70(4): 3012-13. XP009176985; ISSN: 0022-3069.
Wang et al. Cardioprotection of ischemia/reperfusion injury by cholesterol-dependent MG53-mediated membrane repair. Circ. Res 2010. 107(1): 76-83.
Weisleder et al. Immuno-proteomic approach to excitation-contraction coupling in skeletal and cardiac muscle: molecular insights revealed by the mitsugumins. Cell Calcium 2008. 43: 1-8.
Weisleder et al. Mitsugumin 53 (MG53) facilitates vesicle trafficking in striated muscle to contribute to cell membrane repair. Commun Intergrat Biol 2009. 2(3): 225-226.
Weisleder et al. Recombinant MG53 protein modulates therapeutic cell membrane repair in treatment of muscualr dystrophy. Sci Translat Med. 4(139): 139ra85; 12 pages. 2012.
Wells, "Additivity of mutational effects in proteins," Biochemistry 1990. 29(37): 85098517.
Wu et al. J Mol Biol. 1999. 294: 151-162.
Wong. The ABCs of Gene Cloning. Dec. 9, 2005. United States: Springer, p. 93-94.
Zhang et al., MG53 Particpates in Ischaemic Post conditioning through the RISK Signaling Pathway. Cardiovascular Research 2011. 91(1): 108-15.
Zhu, H. et al. "Polymerase Trascriptase Release Factor (PTRF) Anchors MG53 Protein to Cell Inujury Site for Initiation of Membrane Repair", JBC, Apr. 15, 2011, 286(15): 12820-24.
Supplemental European Search Report for 08855963, issued Feb. 23, 2011.
International Search Report for PCT/US2011/030703, issued Apr. 6, 2012.
International Search Report for PCT/US2012/031918, issued Sep. 27, 2012.
File History of U.S. Patent No. 8,420,338, 2013.
NCBI GenBank Accession No. NM 001082015.1 (Mar. 8, 2007).

(56) References Cited

OTHER PUBLICATIONS

U.S. Appl. No. 13/152,077, filed Jun. 2, 2011, Nov. 24, 2011.
U.S. Appl. No. 13/152,096, filed Jun. 2, 2011, Nov. 24, 2011.
U.S. Appl. No. 13/290,070, filed Nov. 5, 2011, U.S. Patent No. 8,420,338.
U.S. Appl. No. 13/526,954, filed Jun. 19, 2012, U.S. Patent No. 9,139,630.
U.S. Appl. No. 13/804,654, filed Mar. 14, 2013, Dec. 5, 2013.
U.S. Appl. No. 14/343,560, filed Nov. 17, 2014, Apr. 23, 2015.
U.S. Appl. No. 14/008,130, filed Sep. 27, 2013, Jan 23, 2014.

* cited by examiner

FIG. 1

```
                      10         20         30         40         50         60
                      |          |          |          |          |          |
Mouse         MSAAPGLLR---QELSCPLCLQLFDAPVTAECGHSFCRACLIRVAGEPAADGTVACPCCQ
Rat           MSTAPGLLR---QELSCPLCLQLFDAPVTAECGHSFCRACLIRVAGEPADDGTVACPCCQ
Human         MSAAPGLLH---QELSCPLCLQLFDAPVTAECGHSFCRACLGRVAGEPAADGTVLCPCCQ
Chimpanzee    MSAAPGLLH   QELSCPLCLQLFDAPVTAECGHSFCRACLGRVAGEPAADCTVLCPCCQ
Rhesus        MSAAPGLLH   QELSCPLCLQLFDAPVTAECGHSFCRACLGRVAGEPAADCTVLCPCCQ
Canine        MSAAPGLLH   QELSCPLCLQLFDAPVTAECGHSFCRACLSRVAGEPAADCTVPCPCCQ
Bovine        MSAAPGLLH   QELSCPLCLQLFDAPVTAECGHSFCRACLSRVAGEPAADCTVLCPSCQ
Rabbit        MSAAPGLLH   QELSCPLCLQLFDAPVTAECGHSFCRACLSRVAGEPAADCTVNCPCCQ
Opposum       MSGAPALMQGMYQDLSCPLCLKLFDAPTTAFCGHSFCRNCLLRLAPDPQAG-TVLCPSCQ
X. laevis     -MSTPQLMQGMQKDLTCQLCLELFRAPVTPECGHTFCQGCLTGVPKNQDQNGSTPCPTCQ
X. tropical   -MSTPQLMQGMQKDLTCPLCLELFRAPVTPECGHTFCQGCLTGAPKNQDQNGSTPCPTCQ
               :*  *:        ::*:* ***:** **:*:****:**: **   . :  .:  ** :*
Prin.cons.    MSAAPGLLHGMQQEL...............................................Q 70         80         90        100        110        120
                      |          |          |          |          |          |
Mouse         APTRPQALSTNLQLSRLVEGLAQVPQGHCEEHLDPLSIYCEQDRTLVCGVCASLGSHRGE
Rat           ASTRPQALSTNLQLARLVEGLAQVPQGHCEEHLDPLSIYCEQDRRLVCGVCASLGSHRGE
Human         APTRPQALSTNLQLARLVEGLAQVPQGHCEEHLDPLSIYCEQDRALVCGVCASLGSHRGE
Chimpanzee    APTRPQALSTNLQLARLVEGLAQVPQGHCEEHLDPLSIYCEQDRALVCGVCASLGSHRGE
Rhesus        APTRPQALSTNLQLARLVEGLAQVPQGHCEEHLDPLSIYCEQDRALVCGVCASLGSHRGE
Canine        ALTRPQALSTNQQLARLVEGLAQVPQGHCEEHLDPLSIYCEQDRALVCGVCASLGSHRCE
Bovine        APTRPQALSTNLQLARLVEGLAQVPQGHCEEHLDPLSIYCEQDRALVCGVCASLGSHRCE
Rabbit        APTRPQALSTNLQLARLVEGLAQVPQGHCEEHLDPLSIYCEQDRVLVCGVCASLGSHRCE
Opposum       APTKPDGLNTNQQLARLVESLAQVPQGHCEEHLDPLSVYCEQDRALICGVCASLGKHRGE
X. laevis     SPSRPETLQINRQLEHLVQSFKQVPQGHCLEHMDPLSVYCEQDXELICGVCASLGKHKGE
X. tropical   TPSRPETLQINRQLEHLVQSFKQVPKGHCLEHLDPLSVYCEQDXELICGVCASLGKHKGE
              : ::*:   *.   *  **::.: ***:*** ** :**** :*****: *:*******.*:**
Prin.cons.    APTRPQALSTNLQLARLVEGLAQVPQGH.................................

130        140        150        160        170        180
                      |          |          |          |          |          |
Mouse         RLLPAAEAQARLKTQLPQQKMQLQEACMRKEKTVAVLEEQLVEVEETVRQFRGAVGEQLG
Rat           RLLPAAEAHARLKTQLPQQKAQLQEACMRKEKSVAVLEEQLVEVEETVRQFRGAVGEQLG
Human         RLLPAAEAHARLKTQLPQQKLQLQEACMRKEKSVAVLEEQLVEVEETVRQFRGAVGEQLG
Chimpanzee    RLLPAAEAHARLKTQLPQQKLQLQEACMRKEKSVAVLEEQLVEVEETVRQFRGAVGEQLG
Rhesus        RLLPAAEAHARLKTQLPQQKLQLQEACMRKEKSVAVLEEQLVEVEETVRQFRGAVGEQLG
Canine        RLLPAAEAHARLKTQLPQQKLQLQEACMRKEKSVALLEEQLMEVEEMVRQFRGAVCEQLG
Bovine        RLLPAAEAHARLKTQLPQQKMQLQEACMRKEKSVALLEEQLLEVEETVRQFRGAVCEQLG
Rabbit        RLLPAAEAHSRLKTQLPQQRLQLQEASMRKFKSVAVLEEQLTEVEFTVRQFRGAVGEQLG
Opposum       SVVTAAEAHQRMKKQLPQQRLQLQEACMRKFKTVALLDRQLAEVEETVRQFQRAVGEQLG
X. laevis     NIITASEEAFAKLKRQLPQQQVILQEARLKKEKTVAVLDRQVAEVQDTVSRFKGNVKHQLN
X. tropical   NIITAAEAYAKLKRQLPQQQVILQEARLKKEKTVAVLDRQVAEVQDTVSRFKGNVKHQLN
              ::.*:**   ::* *****:    ****  ::***:**:*:*:  **:: *  :*:    * .**
Prin.cons.    RLLPAAEAHARLKTQLPQ...........................................

190        200        210        220        230        240
                      |          |          |          |          |          |
Mouse         KMRMFLAALESSLDREAERVRGDAGVALRRELSSLNSYLEQLRQMEKVLEEVADKPQTEF
Rat           KMRMFLAALESSLDREAERVRGEAGVALRRELSSLNSYLEQLRQMEKVLEEVADKPQTEF
Human         KMRVFLAALEGSLDCEAERVRGEAGVALRRELGSLNSYLEQLRQMEKVLEEVADKPQTEF
Chimpanzee    KMRVFLAALEGSLDREAERVRGEAGVALRRELGSLNSYLEQLRQMEKVLEEVADKPQTEF
Rhesus        KMRVFLAALEGSLDREAERVRGEAGVALRRELGSLNSYLEQLRQMEKVLEEVADKPQTEF
Canine        KMRVFLAALEGSLDREAERVRGEAGVALRRELGSLNSYLEQLRQMEKVLEEVADKPQTEF
Bovine        KMRLFLAALEGSLDREAERVRGEAGVALRRELGSLNSYLEQLRQMEKVLEEVADKPQTEF
Rabbit        KMRVFLAALEGSLDREAERVRSEAGVALRRELGGLHSYLEQLRQMEKVLEEVADKPQTEF
Opposum       VMRAFLAALESSLGKEAERVTGEAGTALKAERRIMTSYLDQLQQMEKVLDEVTDQPQTEF
X. laevis     AMRSYLNIMEASLGKEADKRESAATEALLVERKTMGHYLDQLRQMEGVLKDVEGQEQTEF
X. tropical   AMRSYLSIMEASLSKEADNREHTATEALLVERKTLGHYLDQLRQMDGYLKDVESQEQTEF
              **:*:  :*.**. **:.    *: **  *   *  **:**:*: *:**   : :****
Prin.cons.    ...............................................PQTEF
```

FIG. 1 Continued

```
                250        260        270        280        290        300
                 |          |          |          |          |          |
Mouse       LMKFCLVTSRLQKILSESPPPARIDIQLPVISDDFKFQVWKKMFRALMPALFEITFDPSS
Rat         LMKFCLVTSRLQKILSESPPPARIDIQLPVISDDFKFQVWKKMFRALMPALFEITFDPSS
Human       LMKYCLVTSRLQKILAESPPPARLDIQLPIISDDFKFQVWRKMFRALMPALEELTFDPSS
Chimpanzee  LMKYCLVTSRLQKILAESPPPARLDIQLPIISDDFKFQVWRKMFRALMPALEELTFDPSS
Rhesus      LMKYCLVTSRLQKILAESPPPARLDIQLPIISDDFKFQVWRKMFRALMPALEELTFDPSS
Canine      LMKYCLVTSRLQKILAESPPPARLDIQLPVISDDFKFQVWRKMFRALMPVTKELTFDPSS
Bovine      LMKYCLVTSRLQKILAESPPPARLDIQLPIISDDFKFQVWRKMFRALMPARQELTFDPST
Rabbit      LMKYCLVTSRLQKILAESPPPARLDIQLPIISDDFKFQVWRKMFRALMPALEELTFDPSS
Opposum     LRKYCLVTSRLQKILAESPPAARIDIQLPIISDDFKFQVWRKMFRALMPGMFVITFDPAS
X. laevis   LRKYCVVAARLNKILSESPPPGRIDIQLPIISDRFKFQVWRKMFRALMPALFNMTFDPDT
X. tropical LRKYCVVAARLNKILASPPPGRLDIQLPIISDEFKFQVWRKMFRALMPALENLTFDPDT
            *  *:*:*  :**:***:***  .:*******:***:*******:********    : :****  :
Prim.cons.  LMKYCLVTSRLQKILAESPPPARLDIQLPIISDDFKFQVWRKMFRALMPA 310        320        330        340        350        360
                 |          |          |          |          |          |
Mouse       AHPSLVVSSSGRRVECSDQKAPPAGEDTRQFDKAVAVVACQLLSQGEHYWEVEVGDKPRW
Rat         AHPSLVVSASGRRVECSEQKAPPAGEDTCQFDKTVAVVAKQLLSQGEHYWEVEVGDKPRW
Human       AHPSLVVSSSGRRVECSEQKAPPAGEDPRQFDKAVAVVAHQQLSEGEHYWEVDVGDKPRW
Chimpanzee  AHPSLVVSSSGRRVECSEQKAPPAGEDPRQFDKAVAVVAHQQLSEGEHYWEVDVGDKPRW
Rhesus      AHPSLVVSSSGRRVECSEQKAPPAGEDPRQFDKAVAVVAHQQLSECEHYWEVGVGDKPRW
Canine      AHPSLVLSPSGRRVECSDQKAPPAGEDPCQFDKAVAVVACQVLSDGEHYWEVQVGEKPRW
Bovine      AHPSLVISNSGRCVECGEQKAPPAGEDPRQFDKAVAVVTHQLISEGEHYWEVEVGDKPRW
Rabbit      AHPSLVVSPTGRRVECSEQKAPPAGDDARQFDKAVAVVACQLLSDGEHYWEVEVGDKPRW
Opposum     AHPSLLVSPSGRRVECVEQKAPPAGDDPQQFDKAVALVAKQQLSECEHYWEVGVGDKPRW
X. laevis   ACQYLVVSSEGKSVECADQKQS-VSDEPNREDKSNCLVSKQSFTECEHYWEVIVEDKPRW
X. tropical ACQNIVVFSDGKSVECSEQKQS-VSDEPNREDKSNCLVSKESFTECEHYWEVLVEDKPRW
            *:      *:     *: ***  :**   . .::.  :***:  :*:::  ::*******  *  :****
Prim.cons.

370        380        390        400        410        420
                 |          |          |          |          |          |
Mouse       ALGVMAADASRRCRLHAVPSQGLWLLCLRDGKILEAHVEAKEPRALRTPERPPARICLYL
Rat         ALGVMAADASRRGRLHAVPSQGLWLLGLRDGKILEAHVEAKEPRALRTPERPPARIGLYL
Human       ALGVIAAEAPRRGRLHAVPSQGLWLLCLREGKILEAHVEAKEPRALRSPERRPTRICLYL
Chimpanzee  ALGVIAAEAPRRCRLHAVPSQGLWLLCLREGKILEAHVEAKEPRALRSPERRPTRICLYL
Rhesus      ALGVIAAEGPRRGRLHAVPSQGLWLLGLREGKILEAHVEAKEPRALRSPERRPTRIGLYL
Canine      ALGVIAAQASRRGRLHAVPSQGLWLLGLRDGKILEAHVEAKEPRALRTPERRPTRIGIYL
Bovine      ALGVIGAQAGRRGRLHAVPSQGLWLLGLRDGKILEAHVEAKEPRALRTPERRPTRIGIYL
Rabbit      ALGVMASEASRGRLHAVPSQGLWLLGLRDGKTLEAHVEAKEPRALRTPERRPTRLGLYL
Opposum     GLGLISADVSRRCKLHPTPSQGFWMLGLREGKVYEAHVESKEEPKVLRVDGR-PSKIGLYL
X. laevis   ALGIISETANRKGKLHATPSNGFWIIGCKEGKVYEAHTEQKEPRVLRVEGR-PEKIGVYL
X. tropical ALGVISETANRKGKLHASPSNGFWLIGCKEGKVYEAHTEQKEPRVLRVEGR-PEKICIYL
            .**::.      *:*:**   **:*:*::*   ::**    **:.*  ***:.*:   *   *  ::*:**
Prim.cons.

430        440        450        460        470        480
                 |          |          |          |          |          |
Mouse       SFADGVLAFYDASNPDVLTPIFSFHERLPGPVYPTFDVCWHDXGKNAQPILLVGPE-----QFQA(Seq Id No 3)
Rat         SFADGVLTFYDASNTDAITPLFSFHERLPGPVYPMFDVCWHDXGKNSQPILLVGPD-----SFQA(Seq Id No 14)
Human       SFGDGVLSFYDASDADALVPLFAFHERLPRPVYPFFDVCWHDXGKNAQPLLLVGPE-----GAEA(Seq Id No 1)
Chimpanzee  SFGDGVLSFYDASDADALVPLFAFHERLPRPVYPFFDVCWHDXGKNAQPLLLVGPE-----GAEA(Seq Id No 11)
Rhesus      SFGDGVLSFYDASDADALVPLFAFHERLPGPVYPFFDVCWHDXGKNSQPLLLVGSE-----GAEA(Seq Id No 12)
Canine      SFGDGVLSFYDASDPPALELLFAFHERLPGPVYPFFDVCWHDXGKNAQPILLVGPD-----GRFA(Seq Id No 10)
Bovine      SFGDGVLSFYDASDPDALELLFAFHERLPGPVYPFFDVCWHDXGKNAQPLLLVGPEVSGGSGSEA(Seq Id No 13)
Rabbit      SFGDGVLAFYDASDADALELLFAFHERLPGPVYPFFDVCWHDXGKNAQPLLLVGPD-----GQEA(Seq Id No 5)
Opposum     SFRDGVLSFYDASDLDNLLPLYAFHERLPGPVYPFFDVCWHDXGKNAQPLLLLGPD     GEQ(Seq Id No 9)
X. laevis   SFSDGVVSFFDSSDEDNLKLLYTFNERFSGRLHPFFDVCWHDXGKNSQPLKIFYPP-----AEQL(Seq Id No 15)
X. tropical SFSDGVVSFFDSSDEDNIKLLYTFNERFSGRLHPFFDVCWHDXGKNAQPLKIFYPP-----AEQL(Seq Id No 16)
            ** ***::*:*:*:   *  : :::*.**:.   : *.*********:***  :  ..
Prim.cons.                                                              EVSGGSGEEA
```

FIG. 13
a
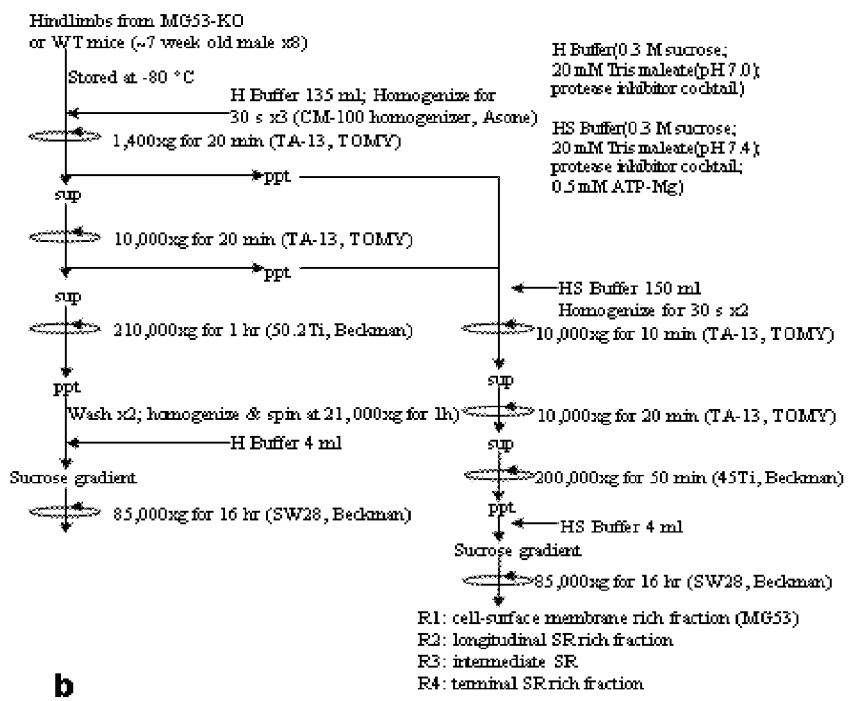
R1: cell-surface membrane rich fraction (MG53)
R2: longitudinal SR rich fraction
R3: intermediate SR
R4: terminal SR rich fraction
b
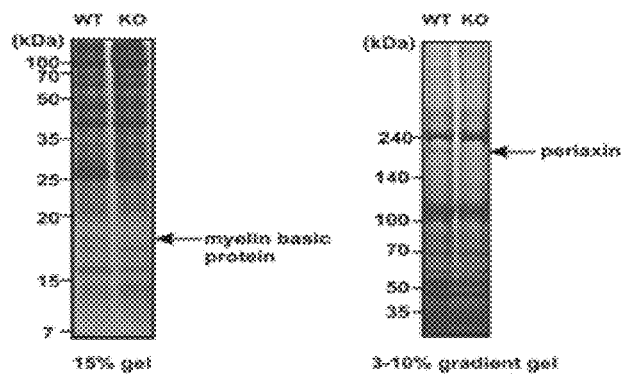

FIG. 16
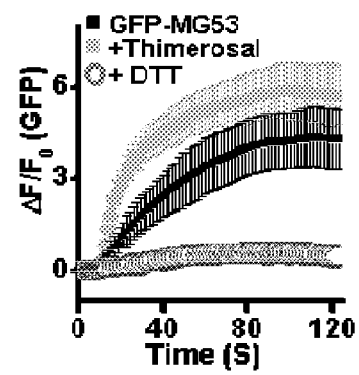
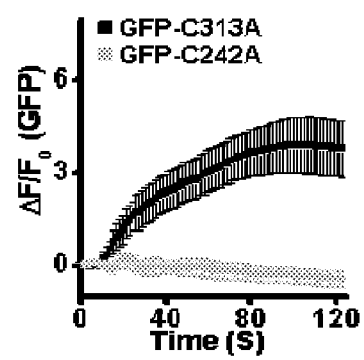
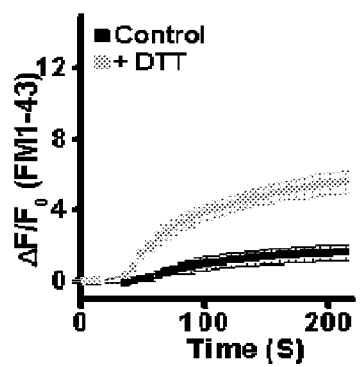

FIG. 18 a-c
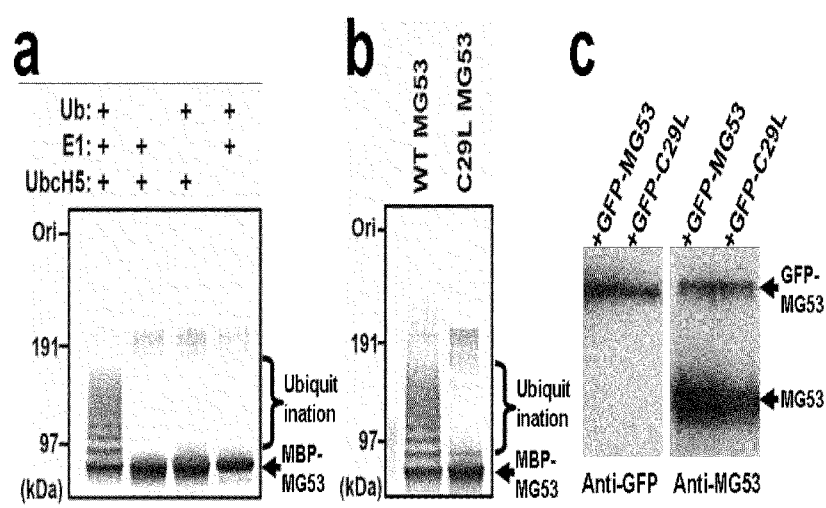

FIG. 18 d-e
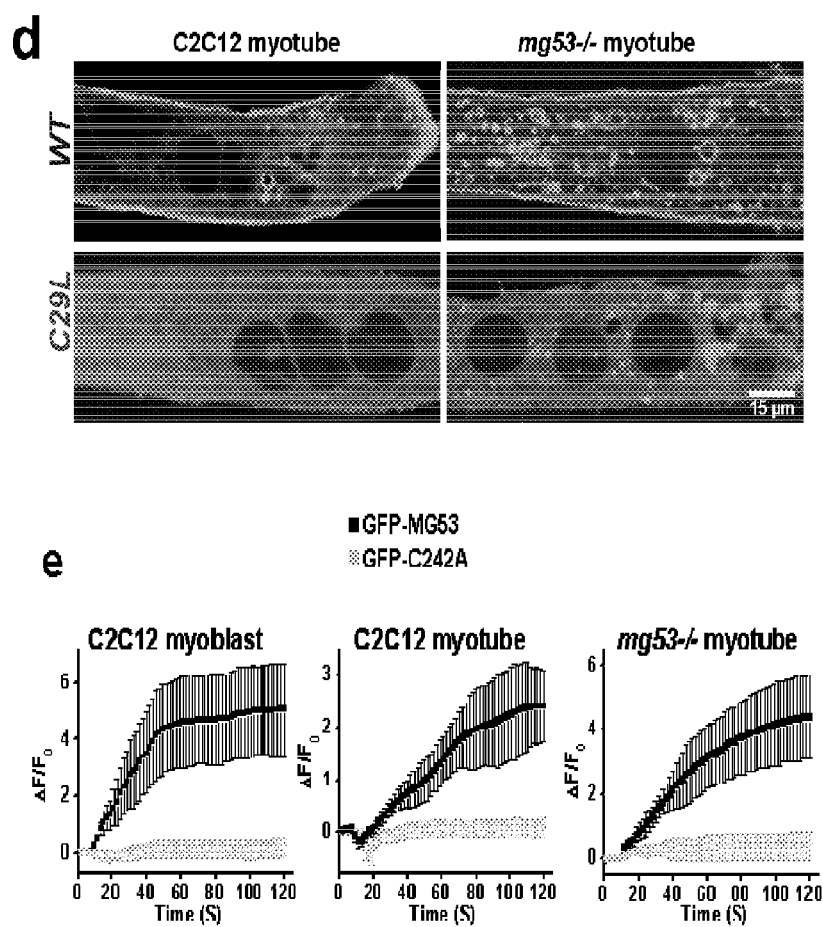

FIG. 20 a-b
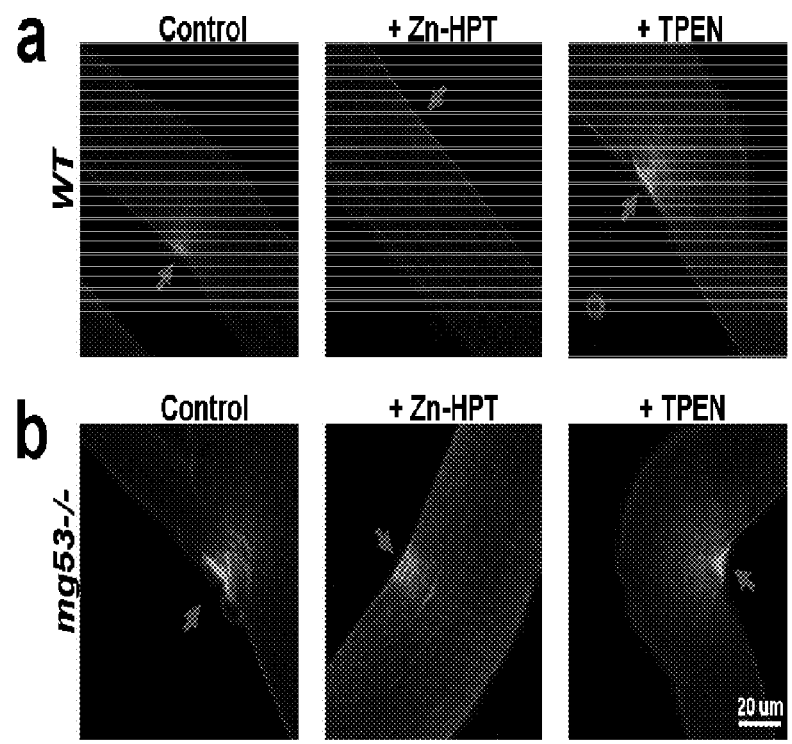

FIG. 20 c-d
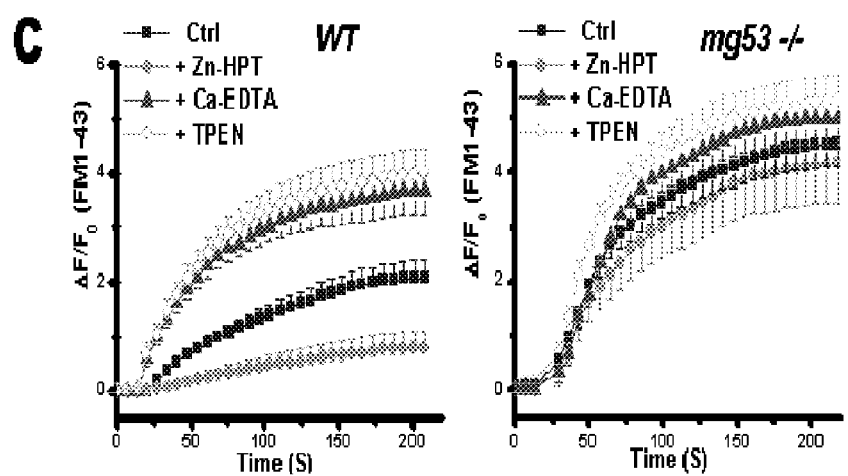
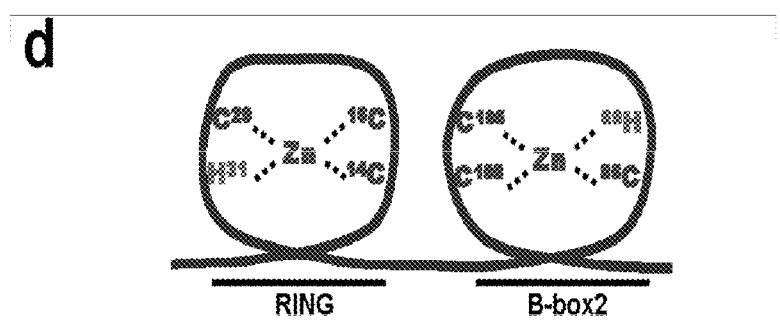

FIG. 21 a-b
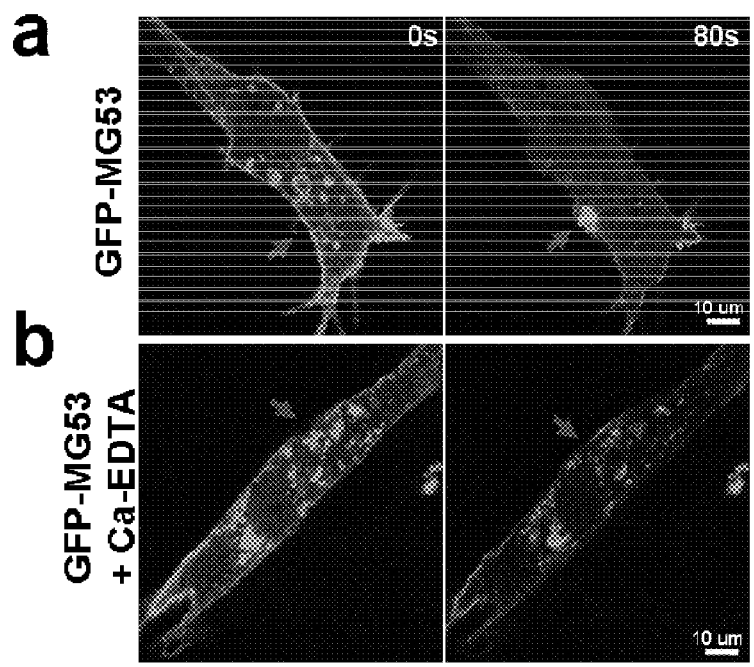

FIG. 21 c-e
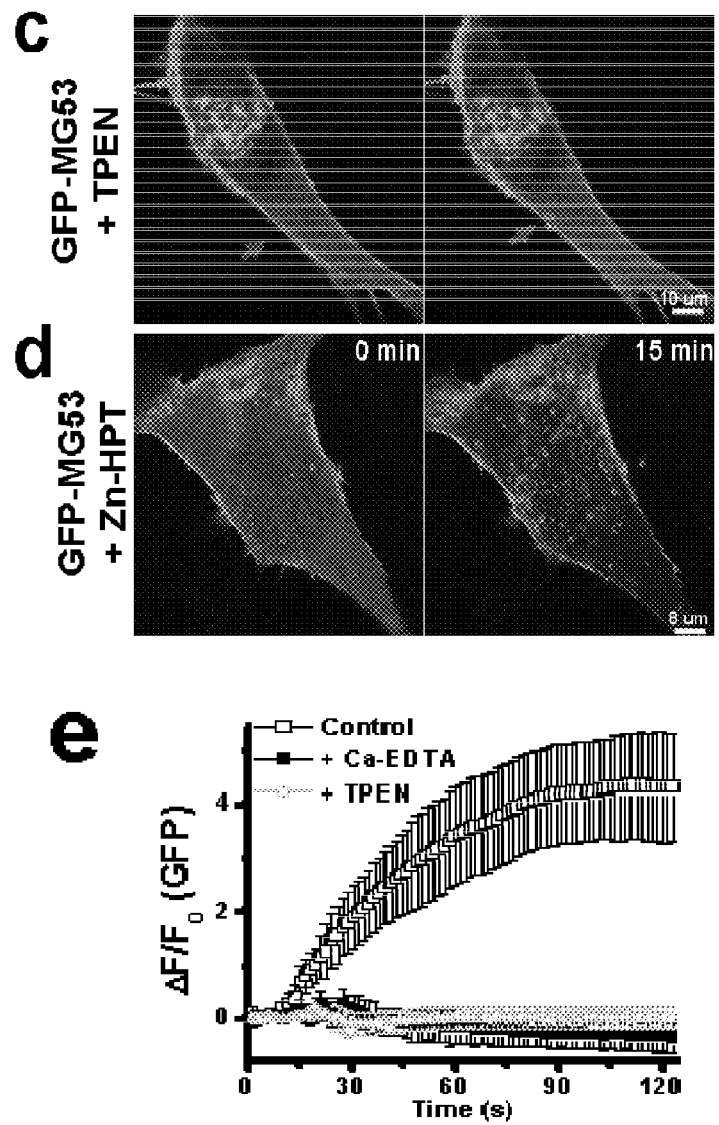

FIG. 23
a
MG53 Ring Motif:
SCPLCLQLFDAPVTAECGHSFCRACLGRVAGEPAADGTVLCPCC
MG53 Bbox Motif:
CEEHLDPLSIYCEQDRALVCGVCASLGSHRGH
b
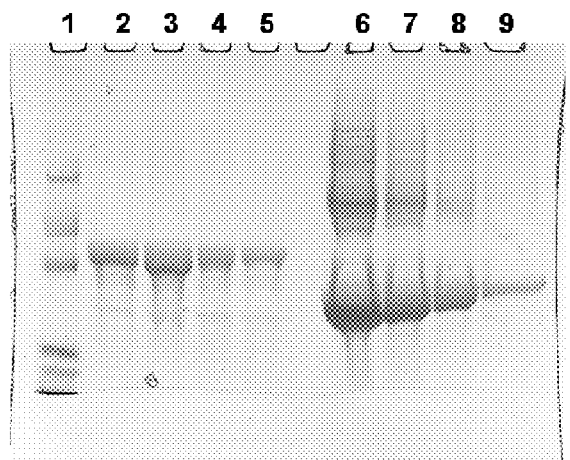
c
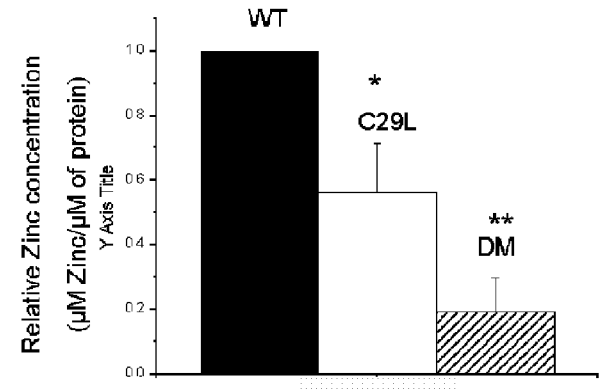

FIG. 30
Before notoginseng
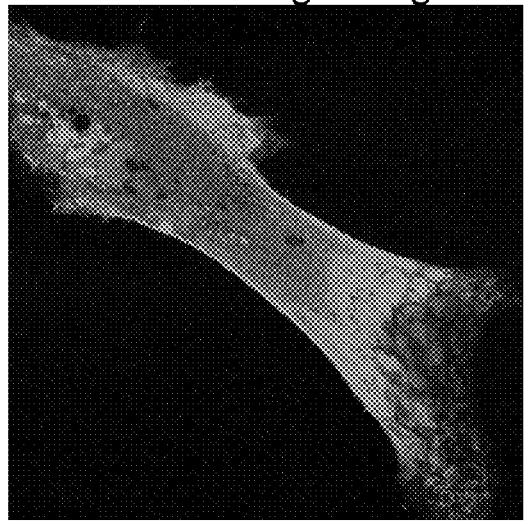
Following notoginseng
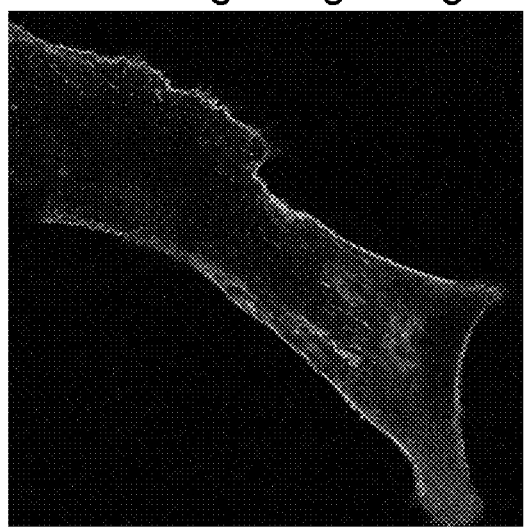

```
                        SEQUENCE LISTING

<160> NUMBER OF SEQ ID NOS: 16

<210> SEQ ID NO 1
<211> LENGTH: 477
<212> TYPE: PRT
<213> ORGANISM: Homo sapiens
<220> FEATURE:
<221> NAME/KEY: misc_feature
<222> LOCATION: (1)..(477)
<223> OTHER INFORMATION: Human MG53 Polypeptide

<400> SEQUENCE: 1

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
                20                  25                  30

Phe Cys Arg Ala Cys Leu Gly Arg Val Ala Gly Glu Pro Ala Ala Asp
            35                  40                  45

Gly Thr Val Leu Cys Pro Cys Cys Gln Ala Pro Thr Arg Pro Gln Ala
        50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
```

```
                100             105             110
     Ser His Arg Gly His Arg Leu Leu Pro Ala Ala Glu Ala His Ala Arg
                    115             120             125
     Leu Lys Thr Gln Leu Pro Gln Gln Lys Leu Gln Leu Gln Glu Ala Cys
             130             135             140
     Met Arg Lys Glu Lys Ser Val Ala Val Leu Glu His Gln Leu Val Glu
     145             150             155             160
     Val Glu Glu Thr Val Arg Gln Phe Arg Gly Ala Val Gly Glu Gln Leu
                         165             170             175
     Gly Lys Met Arg Val Phe Leu Ala Ala Leu Glu Gly Ser Leu Asp Cys
                     180             185             190
     Glu Ala Glu Arg Val Arg Gly Glu Ala Gly Val Ala Leu Arg Arg Glu
                 195             200             205
     Leu Gly Ser Leu Asn Ser Tyr Leu Glu Gln Leu Arg Gln Met Glu Lys
             210             215             220
     Val Leu Glu Glu Val Ala Asp Lys Pro Gln Thr Glu Phe Leu Met Lys
     225             230             235             240
     Tyr Cys Leu Val Thr Ser Arg Leu Gln Lys Ile Leu Ala Glu Ser Pro
                         245             250             255
     Pro Pro Ala Arg Leu Asp Ile Gln Leu Pro Ile Ile Ser Asp Asp Phe
                     260             265             270
     Lys Phe Gln Val Trp Arg Lys Met Phe Arg Ala Leu Met Pro Ala Leu
                 275             280             285
     Glu Glu Leu Thr Phe Asp Pro Ser Ser Ala His Pro Ser Leu Val Val
             290             295             300
     Ser Ser Ser Gly Arg Arg Val Glu Cys Ser Glu Gln Lys Ala Pro Pro
     305             310             315             320
     Ala Gly Glu Asp Pro Arg Gln Phe Asp Lys Ala Val Ala Val Val Ala
                         325             330             335
     His Gln Gln Leu Ser Glu Gly Glu His Tyr Trp Glu Val Asp Val Gly
                     340             345             350
     Asp Lys Pro Arg Trp Ala Leu Gly Val Ile Ala Ala Glu Ala Pro Arg
                 355             360             365
     Arg Gly Arg Leu His Ala Val Pro Ser Gln Gly Leu Trp Leu Leu Gly
             370             375             380
     Leu Arg Glu Gly Lys Ile Leu Glu Ala His Val Glu Ala Lys Glu Pro
     385             390             395             400
     Arg Ala Leu Arg Ser Pro Glu Arg Arg Pro Thr Arg Ile Gly Leu Tyr
                         405             410             415
     Leu Ser Phe Gly Asp Gly Val Leu Ser Phe Tyr Asp Ala Ser Asp Ala
                     420             425             430
     Asp Ala Leu Val Pro Leu Phe Ala Phe His Glu Arg Leu Pro Arg Pro
                 435             440             445
     Val Tyr Pro Phe Phe Asp Val Cys Trp His Asp Lys Gly Lys Asn Ala
             450             455             460
     Gln Pro Leu Leu Leu Val Gly Pro Glu Gly Ala Glu Ala
     465             470             475

<210> SEQ ID NO 2
<211> LENGTH: 1434
<212> TYPE: DNA
<213> ORGANISM: Homo sapiens
<220> FEATURE:
<221> NAME/KEY: misc_feature
<222> LOCATION: (1)..(1434)
```

<223> OTHER INFORMATION: Human MG53 cDNA

<400> SEQUENCE: 2

```
atgtcggctg cgcccggcct cctgcaccag gagctgtcct gcccgctgtg cctgcagctg      60
ttcgacgcgc ccgtgacagc cgagtgcggc cacagtttct gccgcgcctg cctaggccgc     120
gtggccgggg agcggcggc ggatggcacc gttctctgcc cctgctgcca ggcccccacg      180
cggccgcagg cactcagcac caacctgcag ctggcgcgcc tggtggaggg gctgccccag     240
gtgccgcagg gccactgcga ggagcacctg gacccgctga gcatctactg cgagcaggac     300
cgcgcgctgt gtgcggagt gtgcgcctca ctcggctcgc accgcggtca tcgcctcctg      360
cctgccgccg aggcccacgc acgcctcaag acacagctgc acagcagaa actgcagctg      420
caggaggcat gcatgcgtaa ggagaagagt gtggctgtgc tggagcatca gctggtggag     480
gtggaggaga cagtgcgtca gttccggggg gccgtggggg agcagctggg caagatgcgg     540
gtgttcctgg ctgcactgga gggctccttg gactgcgagg cagagcgtgt acggggtgag     600
gcaggggtcg ccttgcgccg ggagctgggg agcctgaact cttacctgga gcagctgcgg     660
cagatggaga aggtcctgga ggaggtggcg gacaagccgc agactgagtt cctcatgaaa     720
tactgcctgg tgaccagcag gctgcagaag atcctggcag agtctccccc acccgcccgt     780
ctggacatcc agctgccaat tatctcagat gacttcaaat tccaggtgtg gaggaagatg     840
ttccgggctc tgatgccagc gctggaggag ctgacctttg acccgagctc tgcgcacccg     900
agcctggtgg tgtcttcctc tggccgccgc gtggagtgct cggagcagaa ggcgccgccg     960
gccggggagg acccgcgcca gttcgacaag gcggtggcgg tggtggcgca ccagcagctc    1020
tccgagggcg agcactactg ggaggtggat gttggcgaca agccgcgctg ggcgctgggc    1080
gtgatcgcgc ccgaggcccc ccgccgcggg cgcctgcacg cggtgccctc gcagggcctg    1140
tggctgctgg ggctgcgcga gggcaagatc ctggaggcac acgtggaggc caaggagccg    1200
cgcgctctgc gcagccccga gaggcggccc acgcgcattg cctttacct gagcttcggc    1260
gacggcgtcc tctccttcta cgatgccagc gacgccgacg cgctcgtgcc gcttttgcc    1320
ttccacgagc gcctgcccag gcccgtgtac cccttcttcg acgtgtgctg gcacgacaag    1380
ggcaagaatg cccagccgct gctgctcgtg ggtcccgaag gcgccgaggc ctga          1434
```

<210> SEQ ID NO 3
<211> LENGTH: 477
<212> TYPE: PRT
<213> ORGANISM: Mus musculus
<220> FEATURE:
<221> NAME/KEY: misc_feature
<222> LOCATION: (1)..(477)
<223> OTHER INFORMATION: Mouse MG53

<400> SEQUENCE: 3

```
Met Ser Ala Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ile Arg Val Ala Gly Glu Pro Ala Ala Asp
        35                  40                  45

Gly Thr Val Ala Cys Pro Cys Cys Gln Ala Pro Thr Arg Pro Gln Ala
    50                  55                  60

Leu Ser Thr Asn Leu Gln Leu Ser Arg Leu Val Glu Gly Leu Ala Gln
65                  70                  75                  80
```

-continued

Val Pro Gln Gly His Cys Glu Glu His Leu Asp Pro Leu Ser Ile Tyr
                85                  90                  95

Cys Glu Gln Asp Arg Thr Leu Val Cys Gly Val Cys Ala Ser Leu Gly
            100                 105                 110

Ser His Arg Gly His Arg Leu Leu Pro Ala Ala Glu Ala Gln Ala Arg
        115                 120                 125

Leu Lys Thr Gln Leu Pro Gln Gln Lys Met Gln Leu Gln Glu Ala Cys
    130                 135                 140

Met Arg Lys Glu Lys Thr Val Ala Val Leu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Met Phe Leu Ala Ala Leu Glu Ser Ser Leu Asp Arg
            180                 185                 190

Glu Ala Glu Arg Val Arg Gly Asp Ala Gly Val Ala Leu Arg Arg Glu
        195                 200                 205

Leu Ser Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ser Pro
                245                 250                 255

Pro Pro Ala Arg Leu Asp Ile Gln Leu Pro Val Ile Ser Asp Asp Phe
            260                 265                 270

Lys Phe Gln Val Trp Lys Lys Met Phe Arg Ala Leu Met Pro Ala Leu
        275                 280                 285

Glu Glu Leu Thr Phe Asp Pro Ser Ala His Pro Ser Leu Val Val
    290                 295                 300

Ser Ser Ser Gly Arg Arg Val Glu Cys Ser Asp Gln Lys Ala Pro Pro
305                 310                 315                 320

Ala Gly Glu Asp Thr Arg Gln Phe Asp Lys Ala Val Ala Val Ala
                325                 330                 335

Gln Gln Leu Leu Ser Gln Gly Glu His Tyr Trp Glu Val Glu Val Gly
            340                 345                 350

Asp Lys Pro Arg Trp Ala Leu Gly Val Met Ala Ala Asp Ala Ser Arg
        355                 360                 365

Arg Gly Arg Leu His Ala Val Pro Ser Gln Gly Leu Trp Leu Leu Gly
    370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Pro Pro Ala Arg Ile Gly Leu Tyr
                405                 410                 415

Leu Ser Phe Ala Asp Gly Val Leu Ala Phe Tyr Asp Ala Ser Asn Pro
            420                 425                 430

Asp Val Leu Thr Pro Ile Phe Ser Phe His Glu Arg Leu Pro Gly Pro
        435                 440                 445

Val Tyr Pro Ile Phe Asp Val Cys Trp His Asp Lys Gly Lys Asn Ala
    450                 455                 460

Gln Pro Leu Leu Leu Val Gly Pro Glu Gln Glu Gln Ala
465                 470                 475

<210> SEQ ID NO 4
<211> LENGTH: 1434
<212> TYPE: DNA

<213> ORGANISM: Mus musculus
<220> FEATURE:
<221> NAME/KEY: misc_feature
<222> LOCATION: (1)..(1434)
<223> OTHER INFORMATION: Mouse MG53 cDNA

<400> SEQUENCE: 4

```
atgtcggctg cacccggcct tctgcgtcag gaactgtcct gcccactgtg cttgcagctg    60
ttcgatgcgc cagtgacggc tgagtgtggc cacagtttct gccgtgcctg cctgatccgg   120
gtggcagggg agcctgctgc ggacggcaca gttgcctgtc cctgttgtca ggcacctaca   180
cggccgcagg ctctaagcac taacctccag ttgtcacgcc ttgtggaggg tttggcgcaa   240
gtgccccaag ccactgcgga ggaacacctg gatccactga gcatctactg cgagcaggac   300
cgcacacttg tgtgtggtgt gtgtgcctcg ctcggttctc accgtggtca tcgtctcctg   360
cctgccgctg aagcccaagc acgcctcaag acacagcttc acagcagaa gatgcagctg   420
caggaggcat gcatgcgcaa ggagaagact gtagcggtgc tggagcatca gctggtggag   480
gtggaggaga cagtgcgcca gttccgggga gctgtcgggg agcagctggg gaagatgcgg   540
atgttcctgg ctgccctaga aagttctctg gaccgtgaag cagaaagggt tcggggtgat   600
gctggggttg ccttgcgtcg ggagctgtca agcctgaact cttacctaga gcaactgagg   660
cagatggaga aggtgctgga ggaggtggct gacaagccac agacagaatt cctcatgaaa   720
ttctgcctgg taaccagcag gctgcagaag atcctgtcag agtcaccacc accggcaagg   780
ctagatatcc agctgcctgt catctcagat gacttcaaat tccaggtgtg aagaagatg   840
ttccgggctc tgatgccagc gctggaggaa ctgactttg accccagctc tgcgcacccg   900
agcctggtgg tgtcctcctc tggtcgccga gtggagtgct cagaccagaa ggcgccgcca   960
gcggagaag acacgcgtca gttcgacaag gcagtagcgg tggtggcgca gcagctgctg  1020
tcacagggcg agcactattg ggaggtggag gtgggcgaca accacgctg ggccctggga  1080
gtgatggcg ctgacgcttc ccgccgtggc cggctgcacg cggtgccctc acaggggctg  1140
tggctgctgg gtctgcgcga tgcaagatc ctggaggcgc acgtggaggc caaggagccg  1200
cgggcactgc gcacccaga gaggcctccg gcgcgcattg gcctctacct aagcttcgca  1260
gatggcgtcc tggcttttcta tgatgcgagc aaccccgacg tacttacgcc aatctttct  1320
ttccacgagc gtctgcccgg gccggtgtac cccatctttg acgtgtgctg gcacgacaag  1380
ggcaagaatg cccagcccct gctgcttgtg gggccggagc aggaacaggc ctga         1434
```

<210> SEQ ID NO 5
<211> LENGTH: 477
<212> TYPE: PRT
<213> ORGANISM: Oryctolagus cuniculus
<220> FEATURE:
<221> NAME/KEY: misc_feature
<222> LOCATION: (1)..(477)
<223> OTHER INFORMATION: Rabbit MG53

<400> SEQUENCE: 5

```
Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ser Arg Val Ala Gly Glu Pro Ala Ala Asp
        35                  40                  45

Gly Thr Val Asn Cys Pro Cys Cys Gln Ala Pro Thr Arg Pro Gln Ala
    50                  55                  60
```

-continued

```
Leu Ser Thr Asn Leu Gln Leu Ala Arg Leu Val Glu Gly Leu Ala Gln
 65                  70                  75                  80

Val Pro Gln Gly His Cys Glu Glu His Leu Asp Pro Leu Ser Ile Tyr
                 85                  90                  95

Cys Glu Gln Asp Arg Val Leu Val Cys Gly Val Cys Ala Ser Leu Gly
            100                 105                 110

Ser His Arg Gly His Arg Leu Leu Pro Ala Ala Glu Ala His Ser Arg
            115                 120                 125

Leu Lys Thr Gln Leu Pro Gln Gln Lys Leu Gln Leu Gln Glu Ala Ser
130                 135                 140

Met Arg Lys Glu Lys Ser Val Ala Val Leu Glu His Gln Leu Thr Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Ser Glu Ala Gly Val Ala Leu Arg Arg Glu
            195                 200                 205

Leu Gly Gly Leu His Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
            275                 280                 285

Glu Glu Leu Thr Phe Asp Pro Ser Ala His Pro Ser Leu Val Val
290                 295                 300

Ser Pro Thr Gly Arg Arg Val Glu Cys Ser Glu Gln Lys Ala Pro Pro
305                 310                 315                 320

Ala Gly Asp Asp Ala Arg Gln Phe Asp Lys Ala Val Ala Val Val Ala
                325                 330                 335

Gln Gln Leu Leu Ser Asp Gly Glu His Tyr Trp Glu Val Glu Val Gly
            340                 345                 350

Asp Lys Pro Arg Trp Ala Leu Gly Val Met Ala Ser Glu Ala Ser Arg
            355                 360                 365

Arg Gly Arg Leu His Ala Val Pro Ser Gln Gly Leu Trp Leu Leu Gly
            370                 375                 380

Leu Arg Asp Gly Lys Thr Leu Glu Ala His Val Glu Ala Lys Glu Pro
385                 390                 395                 400

Arg Ala Leu Arg Thr Pro Glu Arg Arg Pro Thr Arg Leu Gly Leu Tyr
                405                 410                 415

Leu Ser Phe Gly Asp Gly Val Leu Ala Phe Tyr Asp Ala Ser Asp Ala
            420                 425                 430

Asp Ala Leu Glu Leu Leu Phe Ala Phe Arg Glu Arg Leu Pro Gly Pro
            435                 440                 445

Val Tyr Pro Phe Phe Asp Val Cys Trp His Asp Lys Gly Lys Asn Ala
            450                 455                 460

Gln Pro Leu Leu Leu Val Gly Pro Asp Gly Gln Glu Ala
465                 470                 475
```

<210> SEQ ID NO 6
<211> LENGTH: 1434
<212> TYPE: DNA
<213> ORGANISM: Oryctolagus cuniculus
<220> FEATURE:
<221> NAME/KEY: misc_feature
<222> LOCATION: (1)..(1434)
<223> OTHER INFORMATION: Rabbit MG53 cDNA

<400> SEQUENCE: 6

| | | | | | |
|---|---|---|---|---|---|
| atgtcggccg | cgcccggcct | cctgcaccag | gagctgtctt | gcccgctgtg | cctgcagctg | 60 |
| ttcgacgcgc | ccgtgacagc | cgagtgcggc | cacagtttct | gccgcgcctg | cctgagccgc | 120 |
| gtggcggggg | agccggcggc | cgatggcacc | gtgaactgcc | cgtgctgcca | ggcgcccacg | 180 |
| cggccgcagg | cgctcagcac | caacctgcag | ctggcgcgcc | tggtggaggg | gctggcgcag | 240 |
| gtgccgcagg | gccactgcga | ggagcacctg | gacccgctga | gcatctactg | cgagcaggac | 300 |
| cgcgttctcg | tgtgcggcgt | gtgcgcctcg | ctcggctcgc | accgcggcca | ccgcctgctg | 360 |
| cccgccgcca | aggcccactc | gcgtctcaag | acgcagctgc | cccagcagaa | gctgcagctg | 420 |
| caggaggcga | gcatgcgcaa | ggagaagagc | gtggccgtgc | tggagcacca | gctcacggag | 480 |
| gtggaggaga | cagtgcgtca | gttccggggg | gcagtggggg | agcagctggg | caagatgcgg | 540 |
| gtgttcctgg | ccgccctgga | gggctccctg | gaccgcgagg | cagaacgtgt | gcggagcgag | 600 |
| gcggggggtgg | ccttgcggcg | ggagctgggg | ggcctccact | cgtacctgga | gcagctgcgg | 660 |
| cagatggaga | aggtgttgga | ggaggtggct | gacaagccac | agaccgagtt | ccttatgaaa | 720 |
| tattgcctgt | tgaccagcag | gctgcagaag | atcctggcgg | agtcgccacc | acctgctcgt | 780 |
| ctggacatcc | agctgcccat | catttcagat | gacttcaaat | tccaggtgtg | gaggaagatg | 840 |
| ttccgggctc | tgatgccagc | gctggaggag | ctgacctttg | acccgagctc | cgcgcacccg | 900 |
| agcctcgtgg | tgtcacccac | gggccgccga | gtggagtgct | cggagcagaa | ggcgccgccc | 960 |
| gccgggacg | acgcgcgcca | gttcgacaag | gctgtggccg | tggtggcgca | gcagctgctg | 1020 |
| tccgacggcg | agcactactg | ggaggtggag | gtgggcgaca | agccgcgctg | ggcgctgggc | 1080 |
| gtgatggcct | ccgaggcgag | ccgccgtggc | cggctgcacg | ccgtgccctc | acagggtttg | 1140 |
| tggctgctgg | ggctgcgcga | cggcaagacc | ctggaggcgc | acgtggaggc | caaggagccg | 1200 |
| cgcgcgctgc | gcaccccgga | gcggcggccc | acgcgcctcg | gcctctacct | cagcttcggc | 1260 |
| gatggcgtgc | tcgccttcta | cgacgccagc | gacgccgacg | cgctcgagct | gctgtttgct | 1320 |
| ttccgcgagc | gcctgcccgg | gcccgtgtac | cccttcttcg | acgtgtgctg | gcatgacaag | 1380 |
| ggcaagaatg | cgcagccgct | gctgctcgtg | gggccggatg | ccaggaggc | ctga | 1434 |

<210> SEQ ID NO 7
<211> LENGTH: 477
<212> TYPE: PRT
<213> ORGANISM: Homo sapiens
<220> FEATURE:
<221> NAME/KEY: MUTAGEN
<222> LOCATION: (29)..(29)
<223> OTHER INFORMATION: C29L/C242A
<220> FEATURE:
<221> NAME/KEY: MUTAGEN
<222> LOCATION: (242)..(242)
<223> OTHER INFORMATION: C29L/C242A

<400> SEQUENCE: 7

Met Ser Ala Ala Pro Gly Leu Leu His Gln Glu Leu Ser Cys Pro Leu
1               5                   10                  15

```
Cys Leu Gln Leu Phe Asp Ala Pro Val Thr Ala Glu Leu His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
                100                 105                 110

Ser His Arg Gly His Arg Leu Leu Pro Ala Ala Glu Ala His Ala Arg
            115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Cys
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Ala Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Ala
                325                 330                 335

His Gln Gln Leu Ser Glu Gly Glu His Tyr Trp Glu Val Asp Val Gly
            340                 345                 350

Asp Lys Pro Arg Trp Ala Leu Gly Val Ile Ala Ala Glu Ala Pro Arg
        355                 360                 365

Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Arg Pro
```

-continued

```
                435                 440                 445
Val Tyr Pro Phe Phe Asp Val Cys Trp His Asp Lys Gly Lys Asn Ala
    450                 455                 460

Gln Pro Leu Leu Leu Val Gly Pro Glu Gly Ala Glu Ala
465                 470                 475

<210> SEQ ID NO 8
<211> LENGTH: 477
<212> TYPE: PRT
<213> ORGANISM: Didelphis sp.
<220> FEATURE:
<221> NAME/KEY: PEPTIDE
<222> LOCATION: (1)..(477)
<223> OTHER INFORMATION: Opossum MG53

<400> SEQUENCE: 8

Met Ser Gly Ala Pro Ala Leu Met Gln Gly Met Tyr Gln Asp Leu Ser
1               5                   10                  15

Cys Pro Leu Cys Leu Lys Leu Phe Asp Ala Pro Ile Thr Ala Glu Cys
                20                  25                  30

Gly His Ser Phe Cys Arg Asn Cys Leu Leu Arg Leu Ala Pro Asp Pro
            35                  40                  45

Gln Ala Gly Thr Val Leu Cys Pro Ser Cys Gln Ala Pro Thr Lys Pro
        50                  55                  60

Asp Gly Leu Asn Thr Asn Gln Gln Leu Ala Arg Leu Val Glu Ser Leu
65                  70                  75                  80

Ala Gln Val Pro Gln Gly His Cys Glu Glu His Leu Asp Pro Leu Ser
                85                  90                  95

Val Tyr Cys Glu Gln Asp Arg Ala Leu Ile Cys Gly Val Cys Ala Ser
            100                 105                 110

Leu Gly Lys His Arg Gly His Ser Val Val Thr Ala Ala Glu Ala His
        115                 120                 125

Gln Arg Met Lys Lys Gln Leu Pro Gln Arg Leu Gln Leu Gln Glu
    130                 135                 140

Ala Cys Met Arg Lys Glu Lys Thr Val Ala Leu Leu Asp Arg Gln Leu
145                 150                 155                 160

Ala Glu Val Glu Glu Thr Val Arg Gln Phe Gln Arg Ala Val Gly Glu
                165                 170                 175

Gln Leu Gly Val Met Arg Ala Phe Leu Ala Ala Leu Glu Ser Ser Leu
            180                 185                 190

Gly Lys Glu Ala Glu Arg Val Thr Gly Glu Ala Gly Thr Ala Leu Lys
        195                 200                 205

Ala Glu Arg Arg Ile Val Thr Ser Tyr Leu Asp Gln Leu Gln Gln Met
    210                 215                 220

Glu Lys Val Leu Asp Glu Val Thr Asp Gln Pro Gln Thr Glu Phe Leu
225                 230                 235                 240

Arg Lys Tyr Cys Leu Val Ile Ser Arg Leu Gln Lys Ile Leu Ala Glu
                245                 250                 255

Ser Pro Pro Ala Ala Arg Leu Asp Ile Gln Leu Pro Ile Ile Ser Asp
            260                 265                 270

Asp Phe Lys Phe Gln Val Trp Arg Lys Met Phe Arg Ala Leu Met Pro
        275                 280                 285

Gly Met Glu Val Leu Thr Phe Asp Pro Ala Ser Ala His Pro Ser Leu
    290                 295                 300

Leu Val Ser Pro Ser Gly Arg Arg Val Glu Cys Val Glu Gln Lys Ala
305                 310                 315                 320
```

```
Pro Pro Ala Gly Asp Asp Pro Gln Gln Phe Asp Lys Ala Val Ala Leu
                325                 330                 335

Val Ala Lys Gln Gln Leu Ser Glu Gly Glu His Tyr Trp Glu Val Glu
        340                 345                 350

Val Gly Asp Lys Pro Arg Trp Gly Leu Gly Leu Ile Ser Ala Asp Val
    355                 360                 365

Ser Arg Arg Gly Lys Leu His Pro Thr Pro Ser Gln Gly Phe Trp Met
370                 375                 380

Leu Gly Leu Arg Glu Gly Lys Val Tyr Glu Ala His Val Glu Ser Lys
385                 390                 395                 400

Glu Pro Lys Val Leu Lys Val Asp Gly Arg Pro Ser Arg Ile Gly Leu
                405                 410                 415

Tyr Leu Ser Phe Arg Asp Gly Val Leu Ser Phe Tyr Asp Ala Ser Asp
            420                 425                 430

Leu Asp Asn Leu Leu Pro Leu Tyr Ala Phe His Glu Arg Leu Pro Gly
        435                 440                 445

Pro Val Tyr Pro Phe Phe Asp Val Cys Trp His Asp Lys Gly Lys Asn
    450                 455                 460

Ala Gln Pro Leu Leu Leu Gly Pro Asp Gly Glu Gln
465                 470                 475

<210> SEQ ID NO 9
<211> LENGTH: 477
<212> TYPE: PRT
<213> ORGANISM: Canis sp.
<220> FEATURE:
<221> NAME/KEY: PEPTIDE
<222> LOCATION: (1)..(477)
<223> OTHER INFORMATION: Dog MG53

<400> SEQUENCE: 9

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
                20                  25                  30

Phe Cys Arg Ala Cys Leu Ser Arg Val Ala Gly Glu Pro Ala Ala Asp
            35                  40                  45

Gly Thr Val Pro Cys Pro Cys Cys Gln Ala Leu Thr Arg Pro Gln Ala
    50                  55                  60

Leu Ser Thr Asn Gln Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
130                 135                 140

Met Arg Lys Glu Lys Ser Val Ala Leu Leu Glu His Gln Leu Met Glu
145                 150                 155                 160

Val Glu Glu Met Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190
```

```
Glu Ala Glu Arg Val Arg Gly Glu Ala Gly Val Ala Leu Arg Arg Glu
            195                 200                 205

Leu Gly Ser Leu Asn Ser Tyr Leu Glu Gln Leu Arg Gln Met Glu Lys
            210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Val Ile Ser Asp Asp Phe
                260                 265                 270

Lys Phe Gln Val Trp Arg Lys Met Phe Arg Ala Leu Met Pro Val Thr
            275                 280                 285

Lys Glu Leu Thr Phe Asp Pro Ser Ser Ala His Pro Ser Leu Val Leu
            290                 295                 300

Ser Pro Ser Gly Arg Arg Val Glu Cys Ser Asp Gln Lys Ala Pro Pro
305                 310                 315                 320

Ala Gly Glu Asp Pro Cys Gln Phe Asp Lys Ala Val Ala Val Val Ala
                325                 330                 335

Gln Gln Val Leu Ser Asp Gly Glu His Tyr Trp Glu Val Gln Val Gly
                340                 345                 350

Glu Lys Pro Arg Trp Ala Leu Gly Val Ile Ala Ala Gln Ala Ser Arg
            355                 360                 365

Arg Gly Arg Leu His Ala Val Pro Ser Gln Gly Leu Trp Leu Leu Gly
            370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Arg Pro Thr Arg Ile Gly Ile Tyr
                405                 410                 415

Leu Ser Phe Gly Asp Gly Val Leu Ser Phe Tyr Asp Ala Ser Asp Pro
                420                 425                 430

Asp Ala Leu Glu Leu Leu Phe Ala Phe His Glu Arg Leu Pro Gly Pro
            435                 440                 445

Val Tyr Pro Phe Phe Asp Val Cys Trp His Asp Lys Gly Lys Asn Ala
450                 455                 460

Gln Pro Leu Leu Leu Val Gly Pro Asp Gly Glu Glu Ala
465                 470                 475

<210> SEQ ID NO 10
<211> LENGTH: 477
<212> TYPE: PRT
<213> ORGANISM: Pan troglodytes
<220> FEATURE:
<221> NAME/KEY: PEPTIDE
<222> LOCATION: (1)..(477)
<223> OTHER INFORMATION: Chimpanzee MG53

<400> SEQUENCE: 10

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
```

```
            65                  70                  75                  80
Val Pro Gln Gly His Cys Glu His Leu Asp Pro Leu Ser Ile Tyr
                    85                  90                  95
Cys Glu Gln Asp Arg Ala Leu Val Cys Gly Val Cys Ala Ser Leu Gly
                100                 105                 110
Ser His Arg Gly His Arg Leu Leu Pro Ala Ala Glu Ala His Ala Arg
                115                 120                 125
Leu Lys Thr Gln Leu Pro Gln Gln Lys Leu Gln Leu Gln Glu Ala Cys
            130                 135                 140
Met Arg Lys Glu Lys Ser Val Ala Val Leu Glu His Gln Leu Val Glu
145                 150                 155                 160
Val Glu Glu Thr Val Arg Gln Phe Arg Gly Ala Val Gly Glu Gln Leu
                    165                 170                 175
Gly Lys Met Arg Val Phe Leu Ala Ala Leu Glu Gly Ser Leu Asp Arg
                180                 185                 190
Glu Ala Glu Arg Val Arg Gly Glu Ala Gly Val Ala Leu Arg Arg Glu
                195                 200                 205
Leu Gly Ser Leu Asn Ser Tyr Leu Glu Gln Leu Arg Gln Met Glu Lys
            210                 215                 220
Val Leu Glu Glu Val Ala Asp Lys Pro Gln Thr Glu Phe Leu Met Lys
225                 230                 235                 240
Tyr Cys Leu Val Thr Ser Arg Leu Gln Lys Ile Leu Ala Glu Ser Pro
                    245                 250                 255
Pro Pro Ala Arg Leu Asp Ile Gln Leu Pro Ile Ile Ser Asp Asp Phe
                260                 265                 270
Lys Phe Gln Val Trp Arg Lys Met Phe Arg Ala Leu Met Pro Ala Leu
            275                 280                 285
Glu Glu Leu Thr Phe Asp Pro Ser Ser Ala His Pro Ser Leu Val Val
            290                 295                 300
Ser Ser Ser Gly Arg Arg Val Glu Cys Ser Glu Gln Lys Ala Pro Pro
305                 310                 315                 320
Ala Gly Glu Asp Pro Arg Gln Phe Asp Lys Ala Val Ala Val Ala
                325                 330                 335
His Gln Gln Leu Ser Glu Gly Glu His Tyr Trp Glu Val Asp Val Gly
                340                 345                 350
Asp Lys Pro Arg Trp Ala Leu Gly Val Ile Ala Ala Glu Ala Pro Arg
            355                 360                 365
Arg Gly Arg Leu His Ala Val Pro Ser Gln Gly Leu Trp Leu Leu Gly
            370                 375                 380
Leu Arg Glu Gly Lys Ile Leu Glu Ala His Val Glu Ala Lys Glu Pro
385                 390                 395                 400
Arg Ala Leu Arg Ser Pro Glu Arg Arg Pro Thr Arg Ile Gly Leu Tyr
                    405                 410                 415
Leu Ser Phe Gly Asp Gly Val Leu Ser Phe Tyr Asp Ala Ser Asp Ala
                420                 425                 430
Asp Ala Leu Val Pro Leu Phe Ala Phe His Glu Arg Leu Pro Arg Pro
            435                 440                 445
Val Tyr Pro Phe Phe Asp Val Cys Trp His Asp Lys Gly Lys Asn Ala
            450                 455                 460
Gln Pro Leu Leu Leu Val Gly Pro Glu Gly Ala Glu Ala
465                 470                 475

<210> SEQ ID NO 11
```

<211> LENGTH: 477
<212> TYPE: PRT
<213> ORGANISM: Macaca mulatta
<220> FEATURE:
<221> NAME/KEY: PEPTIDE
<222> LOCATION: (1)..(477)
<223> OTHER INFORMATION: Rhesus Monkey MG53

<400> SEQUENCE: 11

Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Gly Arg Val Ala Gly Glu Pro Ala Ala Asp
        35                  40                  45

Gly Thr Val Leu Cys Pro Cys Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Leu Gln Leu Gln Glu Ala Cys
    130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Val Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
                245                 250                 255

Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Leu
        275                 280                 285

Glu Glu Leu Thr Phe Asp Pro Ser Ser Ala His Pro Ser Leu Val Val
    290                 295                 300

Ser Ser Ser Gly Arg Arg Val Glu Cys Ser Glu Gln Lys Ala Pro Pro
305                 310                 315                 320

Ala Gly Glu Asp Pro Arg Gln Phe Asp Lys Ala Val Ala Val Val Ala
                325                 330                 335

His Gln Gln Leu Ser Glu Gly Glu His Tyr Trp Glu Val Glu Val Gly
            340                 345                 350

Asp Lys Pro Arg Trp Ala Leu Gly Val Ile Ala Ala Glu Gly Pro Arg
        355                 360                 365

-continued

```
Arg Gly Arg Leu His Ala Val Pro Ser Gln Gly Leu Trp Leu Leu Gly
    370                 375                 380

Leu Arg Glu Gly Lys Ile Leu Glu Ala His Val Glu Ala Lys Glu Pro
385                 390                 395                 400

Arg Ala Leu Arg Ser Pro Glu Arg Arg Pro Thr Arg Ile Gly Leu Tyr
                405                 410                 415

Leu Ser Phe Gly Asp Gly Val Leu Ser Phe Tyr Asp Ala Ser Asp Ala
            420                 425                 430

Asp Ala Leu Val Pro Leu Phe Ala Phe His Glu Arg Leu Pro Gly Pro
        435                 440                 445

Val Tyr Pro Phe Phe Asp Val Cys Trp His Asp Lys Gly Lys Asn Ser
    450                 455                 460

Gln Pro Leu Leu Leu Val Gly Ser Glu Gly Ala Glu Ala
465                 470                 475
```

<210> SEQ ID NO 12
<211> LENGTH: 482
<212> TYPE: PRT
<213> ORGANISM: Bos sp.
<220> FEATURE:
<221> NAME/KEY: PEPTIDE
<222> LOCATION: (1)..(482)
<223> OTHER INFORMATION: Bovine MG53

<400> SEQUENCE: 12

```
Met Ser Ala Ala Pro Gly Leu Leu His Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ser Arg Val Ala Gly Glu Pro Ala Ala Asp
        35                  40                  45

Gly Thr Val Leu Cys Pro Ser Cys Gln Ala Pro Thr Arg Pro Gln Ala
    50                  55                  60

Leu Ser Thr Asn Leu Gln Leu Ala Arg Leu Val Glu Gly Leu Ala Gln
65                  70                  75                  80

Val Pro Gln Gly His Cys Glu Glu His Leu Asp Pro Leu Ser Ile Tyr
                85                  90                  95

Cys Glu Gln Asp Arg Ala Leu Val Cys Gly Val Cys Ala Ser Leu Gly
            100                 105                 110

Ser His Arg Gly His Arg Leu Leu Pro Ala Ala Glu Ala His Ala Arg
        115                 120                 125

Leu Lys Thr Gln Leu Pro Gln Gln Lys Met Gln Leu Gln Glu Ala Cys
    130                 135                 140

Met Arg Lys Glu Lys Ser Val Ala Leu Leu Glu His Gln Leu Leu Glu
145                 150                 155                 160

Val Glu Glu Thr Val Arg Gln Phe Arg Gly Ala Val Gly Glu Gln Leu
                165                 170                 175

Gly Lys Met Arg Leu Phe Leu Ala Ala Leu Glu Gly Ser Leu Asp Arg
            180                 185                 190

Glu Ala Glu Arg Val Arg Gly Glu Ala Gly Val Ala Leu Arg Arg Glu
        195                 200                 205

Leu Gly Ser Leu Asn Ser Tyr Leu Glu Gln Leu Arg Gln Met Glu Lys
    210                 215                 220

Val Leu Glu Glu Val Ala Asp Lys Pro Gln Thr Glu Phe Leu Met Lys
225                 230                 235                 240

Tyr Cys Leu Val Thr Ser Arg Leu Gln Lys Ile Leu Ala Glu Ser Pro
```

```
                     245                 250                 255
Pro Pro Ala Arg Leu Asp Ile Gln Leu Pro Ile Ile Ser Asp Asp Phe
            260                 265                 270

Lys Phe Gln Val Trp Arg Lys Met Phe Arg Ala Leu Met Pro Ala Arg
            275                 280                 285

Gln Glu Leu Thr Phe Asp Pro Ser Thr Ala His Pro Ser Leu Val Leu
            290                 295                 300

Ser Asn Ser Gly Arg Cys Val Glu Cys Ser Glu Gln Lys Ala Pro Pro
305                 310                 315                 320

Ala Gly Glu Asp Pro Arg Gln Phe Asp Lys Ala Val Ala Val Val Thr
                325                 330                 335

His Gln Leu Leu Ser Glu Gly Glu His Tyr Trp Glu Val Glu Val Gly
            340                 345                 350

Asp Lys Pro Arg Trp Ala Leu Gly Val Ile Gly Ala Gln Ala Gly Arg
            355                 360                 365

Arg Gly Arg Leu His Ala Val Pro Ser Gln Gly Leu Trp Leu Leu Gly
            370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Arg Pro Thr Arg Ile Gly Ile Tyr
                405                 410                 415

Leu Ser Phe Gly Asp Gly Val Leu Ser Phe Tyr Asp Ala Ser Asp Pro
            420                 425                 430

Asp Ala Leu Glu Leu Leu Phe Ala Phe His Glu Arg Leu Pro Gly Pro
            435                 440                 445

Val Tyr Pro Phe Phe Asp Val Cys Trp His Asp Lys Gly Lys Asn Ala
            450                 455                 460

Gln Pro Leu Leu Leu Val Gly Pro Glu Val Ser Gly Gly Ser Gly Ser
465                 470                 475                 480

Glu Ala

<210> SEQ ID NO 13
<211> LENGTH: 477
<212> TYPE: PRT
<213> ORGANISM: Rattus sp.
<220> FEATURE:
<221> NAME/KEY: PEPTIDE
<222> LOCATION: (1)..(477)
<223> OTHER INFORMATION: Rat MG53

<400> SEQUENCE: 13

Met Ser Thr Ala Pro Gly Leu Leu Arg Gln Glu Leu Ser Cys Pro Leu
1               5                   10                  15

Cys Leu Gln Leu Phe Asp Ala Pro Val Thr Ala Glu Cys Gly His Ser
            20                  25                  30

Phe Cys Arg Ala Cys Leu Ile Arg Val Ala Gly Glu Pro Ala Asp Asp
        35                  40                  45

Gly Thr Val Ala Cys Pro Cys Cys Gln Ala Ser Thr Arg Pro Gln Ala
    50                  55                  60

Leu Ser Thr Asn Leu Gln Leu Ala Arg Leu Val Glu Gly Leu Ala Gln
65              70                  75                  80

Val Pro Gln Gly His Cys Glu His Leu Asp Pro Leu Ser Ile Tyr
            85                  90                  95

Cys Glu Gln Asp Arg Thr Leu Val Cys Gly Val Cys Ala Ser Leu Gly
            100                 105                 110
```

-continued

Ser His Arg Gly His Arg Leu Leu Pro Ala Ala Glu Ala His Ala Arg
115                 120                 125

Leu Lys Thr Gln Leu Pro Gln Gln Lys Ala Gln Leu Gln Glu Ala Cys
130                 135                 140

Met Arg Lys Glu Lys Ser Val Ala Val Leu Glu His Gln Leu Val Glu
145                 150                 155                 160

Val Glu Glu Thr Val Arg Gln Phe Arg Gly Ala Val Gly Glu Gln Leu
                165                 170                 175

Gly Lys Met Arg Met Phe Leu Ala Ala Leu Glu Ser Ser Leu Asp Arg
            180                 185                 190

Glu Ala Glu Arg Val Arg Gly Glu Ala Gly Val Ala Leu Arg Arg Glu
            195                 200                 205

Leu Ser Ser Leu Asn Ser Tyr Leu Glu Gln Leu Arg Gln Met Glu Lys
210                 215                 220

Val Leu Glu Glu Val Ala Asp Lys Pro Gln Thr Glu Phe Leu Met Lys
225                 230                 235                 240

Phe Cys Leu Val Thr Ser Arg Leu Gln Lys Ile Leu Ser Glu Ser Pro
                245                 250                 255

Pro Pro Ala Arg Leu Asp Ile Gln Leu Pro Val Ile Ser Asp Asp Phe
            260                 265                 270

Lys Phe Gln Val Trp Lys Lys Met Phe Arg Ala Leu Met Pro Glu Leu
            275                 280                 285

Glu Glu Leu Thr Phe Asp Pro Ser Ser Ala His Pro Ser Leu Val Val
            290                 295                 300

Ser Ala Ser Gly Arg Arg Val Glu Cys Ser Glu Gln Lys Ala Pro Pro
305                 310                 315                 320

Ala Gly Glu Asp Thr Cys Gln Phe Asp Lys Thr Val Ala Val Ala
                325                 330                 335

Lys Gln Leu Leu Ser Gln Gly Glu His Tyr Trp Glu Val Glu Val Gly
            340                 345                 350

Asp Lys Pro Arg Trp Ala Leu Gly Val Met Ala Ala Asp Ala Ser Arg
            355                 360                 365

Arg Gly Arg Leu His Ala Val Pro Ser Gln Gly Leu Trp Leu Leu Gly
370                 375                 380

Leu Arg Asp Gly Lys Ile Leu Glu Ala His Val Glu Ala Lys Glu Pro
385                 390                 395                 400

Arg Ala Leu Arg Thr Pro Glu Arg Pro Ala Arg Ile Gly Leu Tyr
                405                 410                 415

Leu Ser Phe Ala Asp Gly Val Leu Thr Phe Tyr Asp Ala Ser Asn Thr
            420                 425                 430

Asp Ala Leu Thr Pro Leu Phe Ser Phe His Glu Arg Leu Pro Gly Pro
            435                 440                 445

Val Tyr Pro Met Phe Asp Val Cys Trp His Asp Lys Gly Lys Asn Ser
450                 455                 460

Gln Pro Leu Leu Leu Val Gly Pro Asp Ser Glu Gln Ala
465                 470                 475

<210> SEQ ID NO 14
<211> LENGTH: 477
<212> TYPE: PRT
<213> ORGANISM: Xenopus laevis
<220> FEATURE:
<221> NAME/KEY: PEPTIDE
<222> LOCATION: (1)..(477)
<223> OTHER INFORMATION: Xenopus laevis

```
<400> SEQUENCE: 14

Met Ser Thr Pro Gln Leu Met Gln Gly Met Gln Lys Asp Leu Thr Cys
1               5                   10                  15

Gln Leu Cys Leu Glu Leu Phe Arg Ala Pro Val Thr Pro Glu Cys Gly
            20                  25                  30

His Thr Phe Cys Gln Gly Cys Leu Thr Gly Val Pro Lys Asn Gln Asp
        35                  40                  45

Gln Asn Gly Ser Thr Pro Cys Pro Thr Cys Gln Ser Pro Ser Arg Pro
    50                  55                  60

Glu Thr Leu Gln Ile Asn Arg Gln Leu Glu His Leu Val Gln Ser Phe
65                  70                  75                  80

Lys Gln Val Pro Gln Gly His Cys Leu Glu His Met Asp Pro Leu Ser
                85                  90                  95

Val Tyr Cys Glu Gln Asp Lys Glu Leu Ile Cys Gly Val Cys Ala Ser
            100                 105                 110

Leu Gly Lys His Lys Gly His Asn Ile Ile Thr Ala Ser Glu Ala Phe
        115                 120                 125

Ala Lys Leu Lys Arg Gln Leu Pro Gln Gln Val Ile Leu Gln Glu
    130                 135                 140

Ala Arg Leu Lys Lys Glu Lys Thr Val Ala Val Leu Asp Arg Gln Val
145                 150                 155                 160

Ala Glu Val Gln Asp Thr Val Ser Arg Phe Lys Gly Asn Val Lys His
                165                 170                 175

Gln Leu Asn Ala Met Arg Ser Tyr Leu Asn Ile Met Glu Ala Ser Leu
            180                 185                 190

Gly Lys Glu Ala Asp Lys Ala Glu Ser Ala Ala Thr Glu Ala Leu Leu
        195                 200                 205

Val Glu Arg Lys Thr Met Gly His Tyr Leu Asp Gln Leu Arg Gln Met
210                 215                 220

Glu Gly Val Leu Lys Asp Val Glu Gly Gln Glu Gln Thr Glu Phe Leu
225                 230                 235                 240

Arg Lys Tyr Cys Val Val Ala Ala Arg Leu Asn Lys Ile Leu Ser Glu
                245                 250                 255

Ser Pro Pro Gly Arg Leu Asp Ile Gln Leu Pro Ile Ile Ser Asp
            260                 265                 270

Glu Phe Lys Phe Gln Val Trp Arg Lys Met Phe Arg Ala Leu Met Pro
        275                 280                 285

Ala Leu Glu Asn Met Thr Phe Asp Pro Asp Thr Ala Gln Gln Tyr Leu
    290                 295                 300

Val Val Ser Ser Glu Gly Lys Ser Val Glu Cys Ala Asp Gln Lys Gln
305                 310                 315                 320

Ser Val Ser Asp Glu Pro Asn Arg Phe Asp Lys Ser Asn Cys Leu Val
                325                 330                 335

Ser Lys Gln Ser Phe Thr Glu Gly His Tyr Trp Glu Val Ile Val
            340                 345                 350

Glu Asp Lys Pro Arg Trp Ala Leu Gly Ile Ile Ser Glu Thr Ala Asn
        355                 360                 365

Arg Lys Gly Lys Leu His Ala Thr Pro Ser Asn Gly Phe Trp Ile Ile
    370                 375                 380

Gly Cys Lys Glu Gly Lys Val Tyr Glu Ala His Thr Glu Gln Lys Glu
385                 390                 395                 400

Pro Arg Val Leu Arg Val Glu Gly Arg Pro Glu Lys Ile Gly Val Tyr
                405                 410                 415
```

```
Leu Ser Phe Ser Asp Gly Val Ser Phe Asp Ser Asp Glu
            420             425             430

Asp Asn Leu Lys Leu Leu Tyr Thr Phe Asn Glu Arg Phe Ser Gly Arg
            435             440             445

Leu His Pro Phe Phe Asp Val Cys Trp His Asp Lys Gly Lys Asn Ser
450             455             460

Gln Pro Leu Lys Ile Phe Tyr Pro Pro Ala Glu Gln Leu
465             470             475

<210> SEQ ID NO 15
<211> LENGTH: 477
<212> TYPE: PRT
<213> ORGANISM: Xenopus sp.
<220> FEATURE:
<221> NAME/KEY: PEPTIDE
<222> LOCATION: (1)..(477)
<223> OTHER INFORMATION: Xenopus tropicalis MG53

<400> SEQUENCE: 15

Met Ser Thr Pro Gln Leu Met Gln Gly Met Gln Lys Asp Leu Thr Cys
1               5                   10                  15

Pro Leu Cys Leu Glu Leu Phe Arg Ala Pro Val Thr Pro Glu Cys Gly
            20                  25                  30

His Thr Phe Cys Gln Gly Cys Leu Thr Gly Ala Pro Lys Asn Gln Asp
        35                  40                  45

Gln Asn Gly Ser Thr Pro Cys Pro Thr Cys Gln Thr Pro Ser Arg Pro
    50                  55                  60

Glu Thr Leu Gln Ile Asn Arg Gln Leu Glu His Leu Val Gln Ser Phe
65                  70                  75                  80

Lys Gln Val Pro Lys Gly His Cys Leu Glu His Leu Asp Pro Leu Ser
                85                  90                  95

Val Tyr Cys Glu Gln Asp Lys Glu Leu Ile Cys Gly Val Cys Ala Ser
            100                 105                 110

Leu Gly Lys His Lys Gly His Asn Ile Ile Thr Ala Ala Glu Ala Tyr
        115                 120                 125

Ala Lys Leu Lys Arg Gln Leu Pro Gln Gln Val Ile Leu Gln Glu
    130                 135                 140

Ala Arg Leu Lys Lys Glu Lys Thr Val Ala Val Leu Asp Arg Gln Val
145                 150                 155                 160

Ala Glu Val Gln Asp Thr Val Ser Arg Phe Lys Gly Asn Val Lys His
                165                 170                 175

Gln Leu Asn Ala Met Arg Ser Tyr Leu Ser Ile Met Glu Ala Ser Leu
            180                 185                 190

Ser Lys Glu Ala Asp Asn Ala Glu His Thr Ala Thr Gly Ala Leu Leu
        195                 200                 205

Val Glu Arg Lys Thr Met Gly His Tyr Leu Asp Gln Leu Arg Gln Met
    210                 215                 220

Asp Gly Val Leu Lys Asp Val Glu Ser Gln Glu Gln Thr Glu Phe Leu
225                 230                 235                 240

Arg Lys Tyr Cys Val Val Ala Ala Arg Leu Asn Lys Ile Leu Ala Glu
                245                 250                 255

Ser Pro Pro Gly Arg Leu Asp Ile Gln Leu Pro Ile Ile Ser Asp
            260                 265                 270

Glu Phe Lys Phe Gln Val Trp Arg Lys Met Phe Arg Ala Leu Met Pro
        275                 280                 285
```

```
Ala Leu Glu Asn Leu Thr Phe Asp Pro Asp Thr Ala Gln Gln Asn Leu
    290                 295                 300

Val Val Phe Ser Asp Gly Lys Ser Val Glu Cys Ser Glu Gln Lys Gln
305                 310                 315                 320

Ser Val Ser Asp Glu Pro Asn Arg Phe Asp Lys Ser Asn Cys Leu Val
            325                 330                 335

Ser Lys Glu Ser Phe Thr Glu Gly Glu His Tyr Trp Glu Val Leu Val
            340                 345                 350

Glu Asp Lys Pro Arg Trp Ala Leu Gly Val Ile Ser Glu Thr Ala Asn
            355                 360                 365

Arg Lys Gly Lys Leu His Ala Ser Pro Ser Asn Gly Phe Trp Leu Ile
    370                 375                 380

Gly Cys Lys Glu Gly Lys Val Tyr Glu Ala His Thr Glu Gln Lys Glu
385                 390                 395                 400

Pro Arg Val Leu Arg Val Glu Gly Arg Pro Glu Lys Ile Gly Ile Tyr
                405                 410                 415

Leu Ser Phe Ser Asp Gly Val Val Ser Phe Phe Asp Ser Ser Asp Glu
            420                 425                 430

Asp Asn Ile Lys Leu Leu Tyr Thr Phe Asn Glu Arg Phe Ser Gly Arg
            435                 440                 445

Leu His Pro Phe Phe Asp Val Cys Trp His Asp Lys Gly Lys Asn Ala
    450                 455                 460

Gln Pro Leu Lys Ile Phe Tyr Pro Pro Ala Glu Gln Leu
465                 470                 475

<210> SEQ ID NO 16
<211> LENGTH: 101
<212> TYPE: PRT
<213> ORGANISM: Human immunodeficiency virus type 1
<220> FEATURE:
<221> NAME/KEY: PEPTIDE
<222> LOCATION: (1)..(101)
<223> OTHER INFORMATION: HIV-1 TAT protein

<400> SEQUENCE: 16

Met Glu Pro Val Asp Pro Asn Leu Glu Pro Trp Lys His Pro Gly Ser
1               5                   10                  15

Gln Pro Pro Thr Ala Cys Ser Lys Cys Tyr Cys Lys Lys Cys Cys Trp
                20                  25                  30

His Cys Gln Leu Cys Phe Leu Lys Gly Leu Gly Ile Ser Tyr Gly
            35                  40                  45

Arg Lys Lys Arg Lys His Arg Arg Gly Thr Pro Gln Ser Ser Lys Asp
    50                  55                  60

His Gln Asn Pro Ile Pro Glu Gln Pro Leu Pro Ile Ile Arg Gly Asn
65                  70                  75                  80

Gln Thr Gly Pro Lys Glu Gln Lys Lys Thr Val Ala Ser Lys Ala Glu
                85                  90                  95

Arg Asp Leu Cys Ala
            100
```

COMPOSITIONS AND METHODS TO MODULATE CELL MEMBRANE RESEALING

CROSS-REFERENCE TO RELATED APPLICATIONS

Under 35 U.S.C. §119(e) this application claims the benefit of U.S. Provisional Applications Nos. 61/005,410 filed Dec. 4, 2007; entitled: Method to Modulate Cell Membrane Resealing.

STATEMENT REGARDING FEDERALLY SPONSORED RESEARCH

The U.S. Government has certain rights in this invention pursuant to the following grants: RO1-HL0691000 awarded to Dr. Jianjie Ma by the United States National Institutes of Health (NIH).

INCORPORATION BY REFERENCE

In compliance with 37 C.F.R. §1.52(e)(5), the sequence information contained in electronic file name: Ma_2008utility_ST25.txt; size 57 KB; created on: Dec. 2, 2008; using Patent-In 3.5, and Checker 4.4.0 is hereby incorporated herein by reference in its entirety.

FIELD OF THE INVENTION

This invention relates to polypeptide compositions and methods of use thereof for the modulation of cell membrane repair.

BACKGROUND

To maintain cellular homeostasis, eukaryotic cells must conserve the integrity of their plasma membrane through active recycling and repair in response to various sources of damage. For example, in response to external damage and internal degeneration, the cells of the body must repair the membrane surrounding the each individual cell in order to maintain their function and the health of the organism.

Repair of damage to the plasma membrane is an active and dynamic process that requires several steps, including participation of molecular sensor(s) that can detect acute injury to the plasma membrane, nucleation of intracellular vesicles at the injury site and vesicle fusion to enable membrane patch formation. It has been demonstrated that entry of extracellular calcium is involved in the fusion of intracellular vesicles to the plasma membrane, however, the molecular machinery involved in sensing the damaged membrane signal and the nucleation process for repair-patch formation have not been fully resolved.

Defects in the ability of the cell to repair external membranes have been linked to a broad spectrum of diseases and pathological conditions, for example, neurodegenerative diseases (e.g., Parkinson's Disease, BSE, and Alzheimer's), heart attacks, heart failure, muscular dystrophy, bed sores, diabetic ulcers, oxidative damage, and tissue damage such as sinusitis that occurs as side effect from the administration of chemotherapeutic agents. Also, the muscle weakness and atrophy associated with various diseases, as well as the normal aging process, has been linked to altered membrane repair. In order for these cells to repair their membranes in response to acute damage they make use of small packets of membrane that are inside of the cell, referred to as vesicles. These vesicles are normally found within the cell, but upon damage to the cell membrane, these vesicles move to the damage site and form a patch to maintain the cell integrity. Without this essential function, the cell can die and the cumulative effect of this cellular injury can eventually result in dysfunction of the tissue or organ.

Accordingly, there exists an ongoing need for the development of pharmaceutical modulators of the cell membrane repair process for the treatment of conditions related to acute and chronic cellular and tissue damage.

SUMMARY

The present invention relates to the surprising and unexpected discovery of proteins and processes involved in the repair of cell membrane damage. The invention generally relates to nucleic acids, and polypeptides encoded from nucleic acids of the invention, which, alone or in combination with other components, can modulate the process of cell membrane resealing in a broad range of cell and tissue types. The invention also relates to compositions, for example, polypeptides, nucleic acids encoding cytoplasmic, nuclear, membrane bound, and secreted polypeptides; as well as vectors, host cells, antibodies, recombinant proteins, pseudopeptides, fusion proteins, chemical compounds, and methods for producing the same.

In certain aspects, the present invention also relates to compositions useful as therapeutics for treating and prevention of diseases and disorders related to cellular and/or tissue damage. Therapeutic compositions of the invention comprise MG53 polypeptides, and nucleic acids encoding MG53 polypeptides, for example, the protein of SEQ ID NO. 1 and MG53 polypeptide mutants, homologs, fragments, truncations, pseudopeptides, peptide analogs, and peptidomimetics (herein, "MG53 polypeptides"), as well as compounds that can modulate the activity of MG53 or intermolecular interactions of MG53 with other proteins, for example, CSN6, kinesin, caveolin-3 (SEQ ID NO. 8), periaxin, and myelin-basic-protein. As described herein, MG53 mediates the repair of damage to cellular membranes, and therefore, the targeting and modulating MG53 gene expression, polypeptide synthesis, activity or protein-protein interactions represent a novel therapeutic intervention for tissue repair.

In an additional aspect, the invention relates to the discovery of polypeptide compositions comprising amino acid components or domains that can facilitate the repair of cell membranes. For example, embodiments of this aspect of the invention include isolated or recombinant polypeptides comprising certain amino acid components including a RING finger zinc-binding domain, a B-box zinc-binding domain, a Leucine zipper coiled-coil domain, a phospholipid binding domain, a redox sensitive amino acid, an E3-ligase domain, and a SPRY domain, wherein the components are covalently joined contiguously in a single polypeptide, and wherein the polypeptide facilitates cell membrane repair.

In further aspects, the invention relates to compositions comprising a polypeptide of the invention in combination with an agent that modulates, synergistically, the membrane repair activity of the polypeptides of the invention. In certain embodiments, the modulating agents include, for example, phosphotidylserine; zinc, for example, in the form of a zinc salt, zinc carrier or zinc conjugate; *notoginsing*; and an oxidizing agent.

In certain additional aspects the invention relates to compositions and methods related to the treatment of tissue damage. In certain exemplary embodiments, the invention encompasses, for example, the administration of an effective amount of a therapeutic composition of the invention for the prevention and/or treatment of cell membrane damage; wound healing; ameliorating surgical trauma, treatment and/or prevention of age-related deficiencies in tissue repair that occur as a natural side-effect of the aging process; treatment and/or prevention of injury to any type of muscle tissue, such as those occurring in subjects suffering from cardiovascular diseases and/or sports-related injuries; the treatment and/or prevention of muscular dystrophy, cardiac ischemia, heart failure, aging degeneration, neurodegeneration, sepsis, bacterial infection, gingivitis, gum recession, periodontal disease, wrinkle protection, dermal abrasion, UV damage, nitrogen mustard (chemical blistering agents), ulcers, COPD, wound healing, geriatric medicine, anti-inflammatory or any combination thereof; as well as the repair and regeneration of body tissues through cosmetic or personal care use.

In addition, the invention relates to nucleic acids, including interfering nucleic acids, and polypeptides encoding MG53 interacting proteins, for example, CSN6, kinesin, caveolin-3 (SEQ ID NO. 8), periaxin, and myelin-basic-protein, mutants, truncations, fragments, homologs, pseudopeptides and peptidomimetics, as well as compounds that can modulate their activity or their intermolecular interactions with MG53. Therefore, in additional aspects, the present invention encompasses methods for the targeting of CSN6, kinesin, caveolin-3 (SEQ ID NO. 8), periaxin, and myelin-basic-protein gene expression, activity, and/or intermolecular interactions for the treatment and/or prevention of a disease or disorder in a subject, for example, for the promotion of tissue repair as described herein.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

and no Evans blue staining (right). In contrast, and mg53−/− mice display a Evans blue infiltration into myocytes, indicating that there are significant defects in membrane integrity in the mg53−/− heart.

Figure 7:
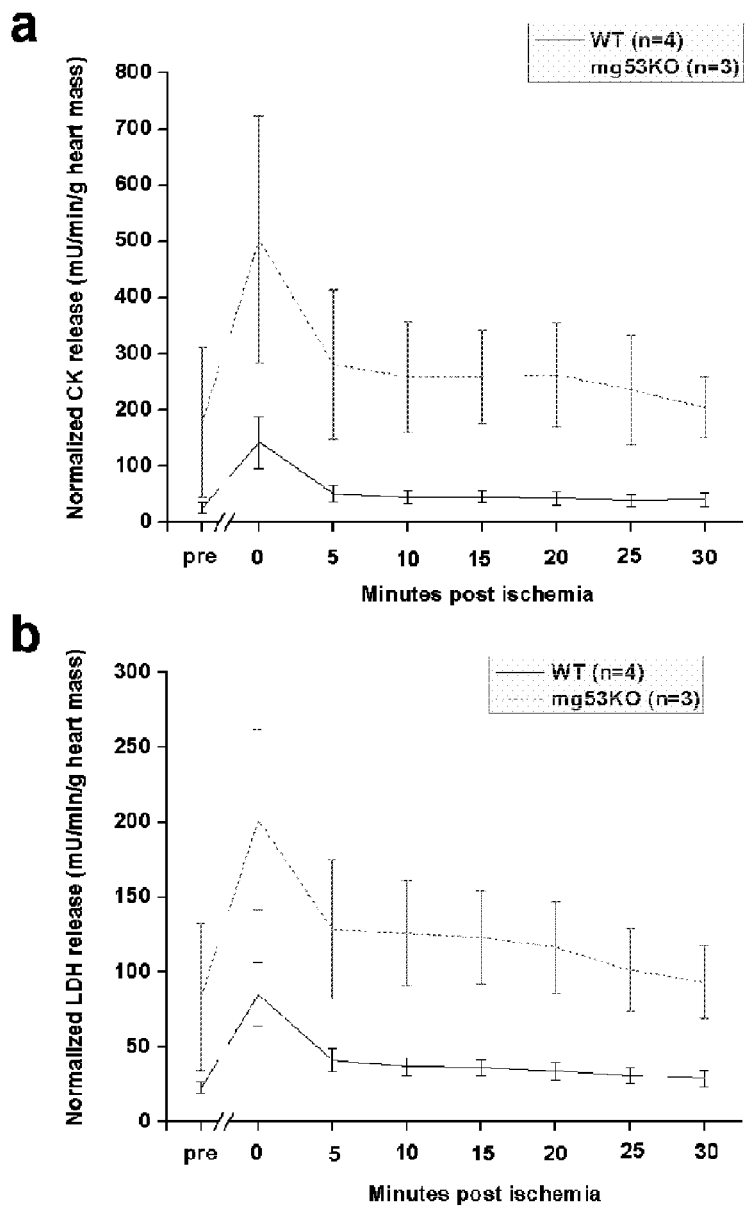

FIG. 7. Loss of MG53 increases susceptibility to cardiac ischemia reperfusion injury. Hearts from wild type (WT) and mg53−/− mice were isolated and perfused on a Langendorff apparatus. Global ischemia was induced for 30 minutes by cessation of perfusate flow. The damage produced in the heart following restoration of perfusate flow (time 0) was measured by enzymatic assays for (a) creatine kinase (CK) or (b) lactate dehydrogenase (LDH). Hearts from mg53−/− mice (dashed lines) show more damage than WT (solid lines). Data is presented as mean±S.D. for each listed time point.

Figure 8:
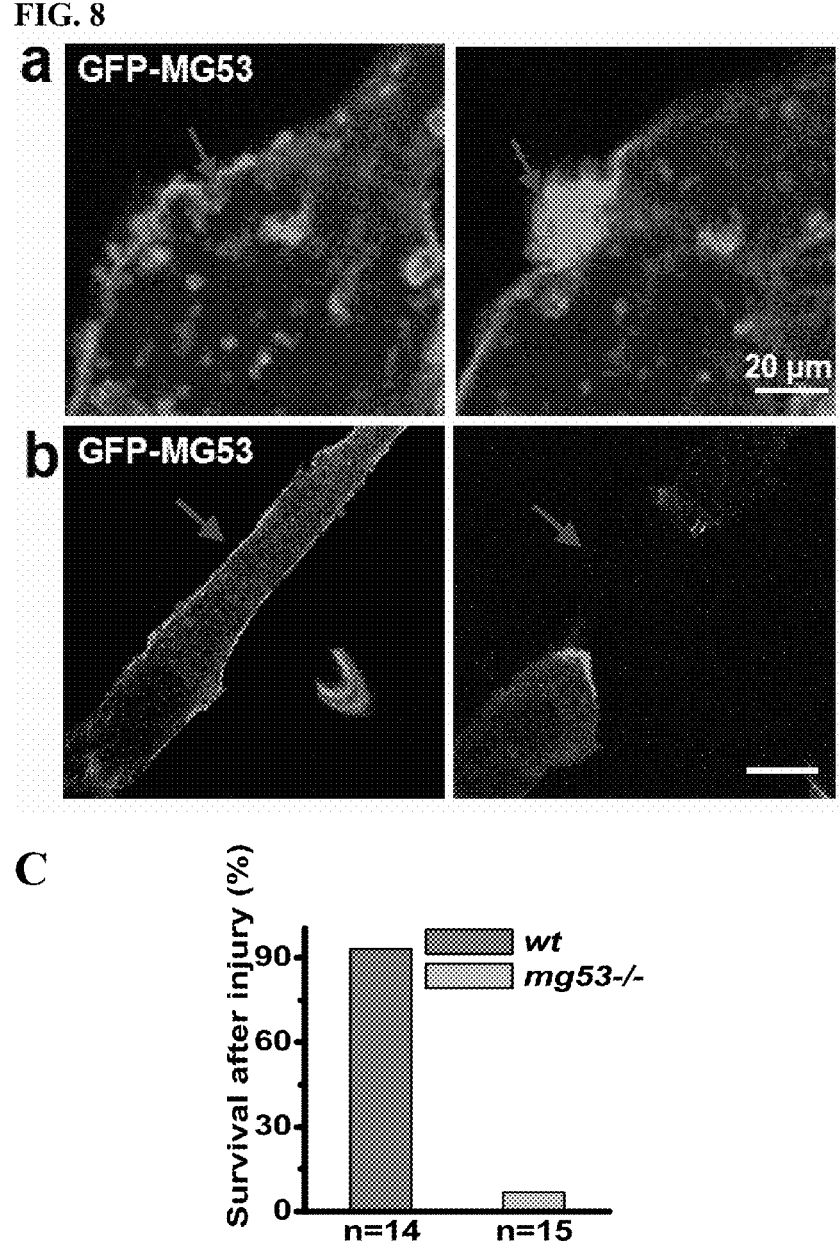

FIG. 8. MG53 containing vesicles form a patch in the plasma membrane following physical insult. a) Damage of a C2C12 myoblast membrane using a micropipette leads to rapid accumulation of GFP-MG53 at the injury site (arrow). Images were representative of n=40 separate cells. b) Recovery of a mature C2C12 myotube in response to a severe damage, e.g. separation of the cell membrane, is associated with recruitment of GFP-MG53 toward the healing site (n=28). c) Comparison of survival rates of wild type and mg53−/− primary skeletal myotubes. This data illustrates that MG53 is required for membrane resealing in striated muscle cells.

Figure 9:
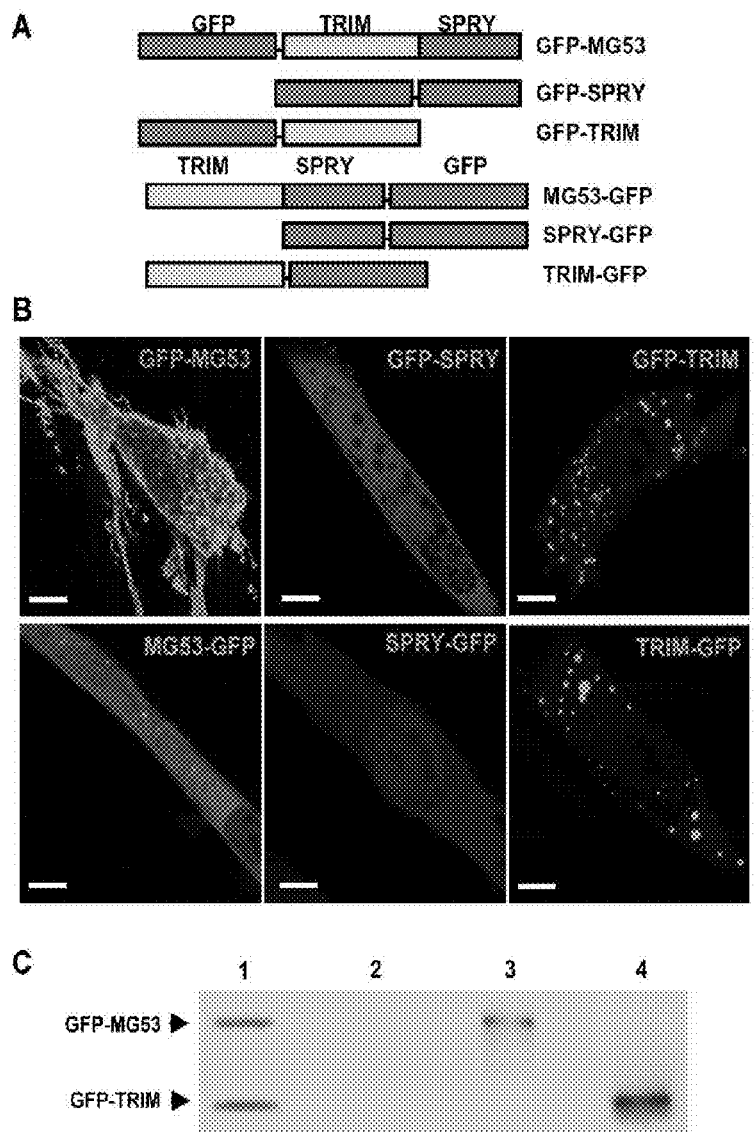

FIG. 9. Role of TRIM and SPRY domains in targeting of MG53 to the cell surface membrane of muscle cells. A. Scheme of the MG53 deletion fusion protein constructs with GFP fused to the N-terminus or C-terminus. With reference to SEQ ID NO. 1, "TRIM" represents a.a. 1-287 and "SPRY" represents a.a. 288-477 and includes both the PRY and SPRY motifs. B. Representative confocal images showing intracellular localization of each deletion construct in C2C12 cells. Scale bar is 5 µm. C. MG53 interacts with caveolin-3 through the TRIM motif. Cell lysate from CHO cells co-transfected with GFP-MG53 or GFP-TRIM and pcDNA-Cav-3 was subjected to IP with anti-caveolin-3 (mouse monoclonal antibody). (Lane 1, mixed cell lysate as positive control; Lane 2, normal mouse IgG as negative control; lane 3, lysate from cells overexpressing GFP-MG53; Lane 4, lysate from cells overexpressing GFP-TRIM).

Figure 10:
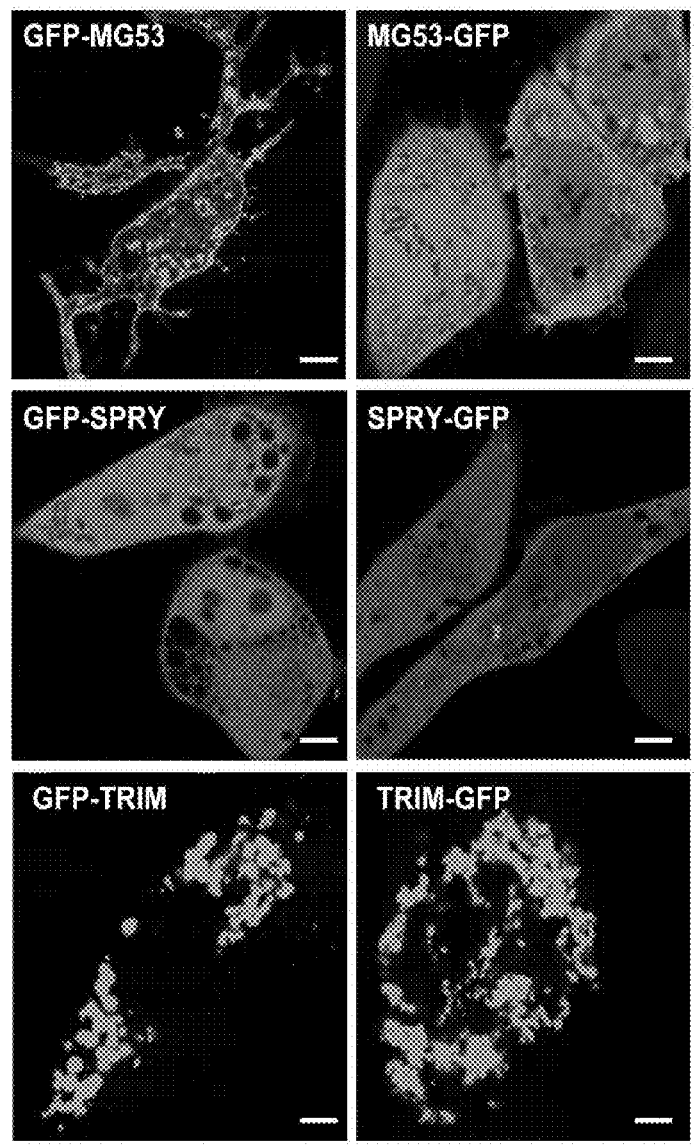

FIG. 10. Role of TRIM and SPRY domains in targeting of MG53 to the cell surface membrane in non-muscle CHO cells. Representative confocal images showing that GFP-MG53 exhibits intracellular vesicle, membrane targeting and budding, however MG53-GFP is mainly soluble in nature (upper panel); SPRY-GFP and GFP-SPRY are cytosolic (middle panel); TRIM-GFP and GFP-TRIM are mainly intracellular vesicle, and do not target to plasma membrane (lower panel). "TRIM" represents a.a. 1-287 and "SPRY" represents a.a. 288-477 and includes both the PRY and SPRY motifs. Scale bar is 5 µm.

Figure 11:
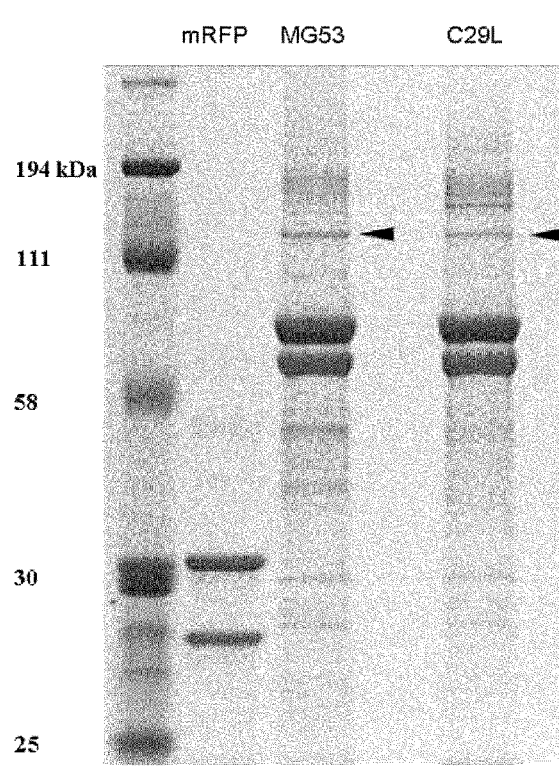

FIG. 11. MG53 can interact with Kinesin family member 11 (Kif11). (a) Cell lysates were isolated from HEK293 cells stably expressing FLAG-tagged versions of either RFP (mRFP), RFP-MG53 (MG53) or C29L mutant RFP-MG53 (C29L). Extracts were co-immunoprecipitated with anti-FLAG antibody and then run on a SDS-PAGE gel. Coommassie staining revealed specific bands that would co-IP by this approach. One prominent band was for Kif11 (arrowhead). (b) Mass spectroscopy was used to identify particular bands from these gels. This representative mass spectroscopy tracing shows that MG53 can pull down Kif11 from cell lysates.

Figure 12:
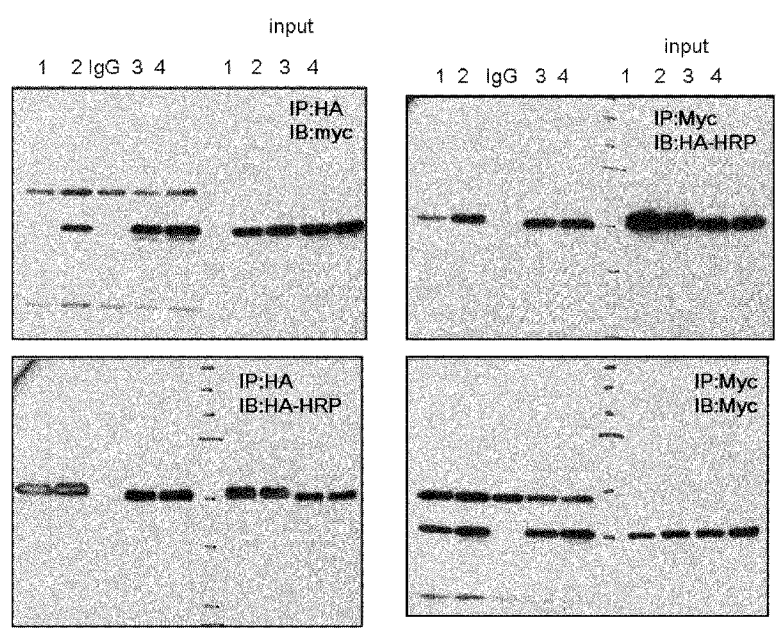

FIG. 12. MG53 can interact with COP9 complex homolog subunit 6 (CSN6). HEK293 cells were transiently transfected with HA-tagged human MG53 and myc-tagged CSN6 and then used for co-immunoprecipitation (IP) using antibodies against the recombinant tags. The presence of the protein following pull down was confirmed using Western immunoblots (IB). MG53 can pull down CSN6 and that CSN6 can also pull down MG53. This provides evidence that these two proteins can interact within the cell. Lanes 1=HA-hMG53+hCSN6+DMSO, Lanes 2=HA-hMG53+hCSN6+MG132, Lanes 3=HA-mMG53+hCSN6+DMSO, Lanes 4=HA-mMG53+hCSN6+MG132.

FIG. 13. MG53 can interact with myelin basic protein or periaxin. (a) Schematic diagrams of methods for biochemical isolation of vesicle fractions from either wild type (WT) or mg53−/− (KO) skeletal muscle. (b) Fractions isolated with methods presented in a were run on with 15% (left) of gradient (right) SDS-PAGE gels. Brilliant Blue (CBB) staining revealed specific bands that we differentially present in WT or KO muscle. Two prominent bands were identified as myelin basic protein or periaxin (arrows) by mass spectroscopy.

Figure 14:
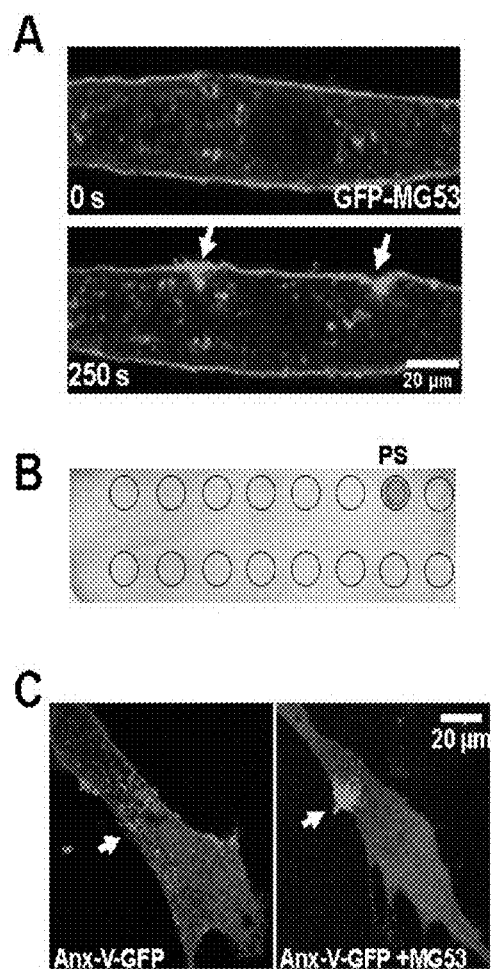
Figure 14:
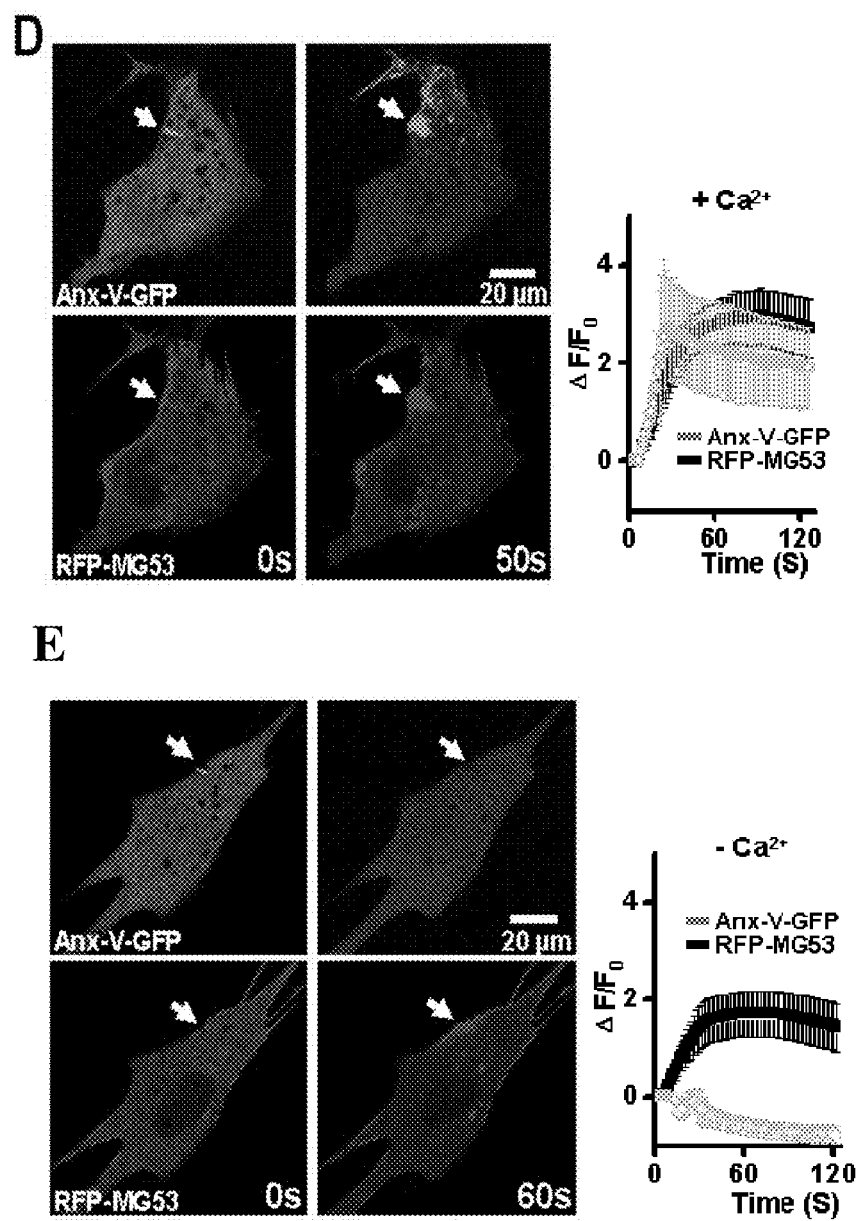

FIG. 14. MG53 interacts with cellular membranes through an association with phosphatidylserine to mediate vesicular trafficking. (A) When GFP-MG53 is expressed in these mg53(−/−) myotubes, the protein will properly localize to the plasma membrane and intracellular vesicles (top). $PIP_2$-Strip lipid dot blot analysis reveals recombinant MG53 (1 µg/ml) specifically binds phosphatidylserine (PS) and not other membrane lipids, including sphingosine-1-P, phosphatidic acid, phosphotidylcholine, phosphatidylethanolamine and various phosphainositol metabolites (B). Using Annexin-V-GFP, we observed rapid labeling of Annexin-V-GFP at the C2C12 myoblast injury site. Annexin-V-GFP (a molecule with well defined ability to bind PS) transfected into C2C12 myoblasts displays minimal translocation following cell wounding with a microelectrode (left), while co-expression of Annexin-V-GFP with RFP-MG53 (right) results in accelerated accumulation of Annexin-V-GFP (C). The accumulation of Annexin-V-GFP was accelerated by co-expression of RFP-MG53 (0.93±0.21 $\Delta F/F_0$ control; 2.9±0.63 $\Delta F/F_0$+MG53). Entry of extracellular $Ca^{2+}$ through the damaged plasma membrane allowed Annexin-V binding to PS, leading to its transition from a soluble pattern before cell injury to distinct localization to plasma membrane and intracellular vesicles (D). Removal of $Ca^{2+}$ from the extracellular solution disrupted the labeling of PS by Annexin-V-GFP at the injury site, translocation of RFP-MG53 to the injury site was maintained (E).

Figure 15:
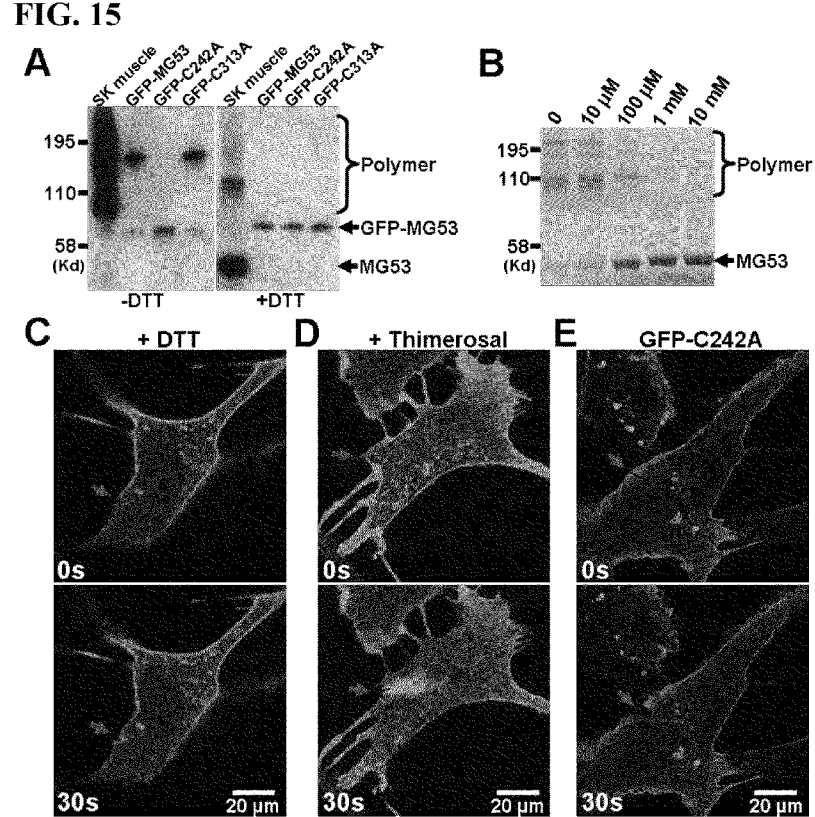

FIG. 15. Acute disruption of the plasma membrane leads to exposure of the cell interior to an external oxidized environment. (A and B) MG53 exists primarily as monomers in a reduced environment generated by the addition of dithiothreitol (DTT). (C) inclusion of 5 mM DTT in the extracellular solution produced drastic effects on the MG53-mediated membrane repair process in C2C12 cells. (D) Thimerosal oxidizes sulfhydryl groups at cysteine residues. (E) multiple conserved cysteine residues were mutated into alanines—membrane targeting is maintained, but completely disrupts ability to facilitate the membrane repair process; i.e., no accumulation of C242A was observed at the injury site.

FIG. 16. (A) Under a reduced extracellular environment (+DTT), translocation of GFP-MG53 toward the injury site was largely disrupted. The addition of an oxidizing agent (Thimerosal) into the extracellular solution results in an increased translocation of GFP-MG53 to injury sites on the cell membrane. These experiments were conducted in C2C12 cells. (B) MG53 with a C242A mutation (GFP-C242A) cannot translocate to injury sites on the plasma membrane. Since a different conserved cysteine mutant, C313A, maintained oligomerization pattern under oxidized conditions and displayed similar translocation and membrane-repair function as the wild type GFP-MG53. Thus, the oxidation of Cys242 likely induces oligomerization of MG53, providing a nucleation site for repairsome formation at injury sites. These experiments were conducted with C2C12 cells. (C) Modulation of the extracellular redox state can affect the resealing of isolated muscle fiber membranes as the addition of DTT to the extracellular solution prevents membrane resealing, as measured by an increase in entry of FM-143 dye applied outside of the cell.

Figure 17:
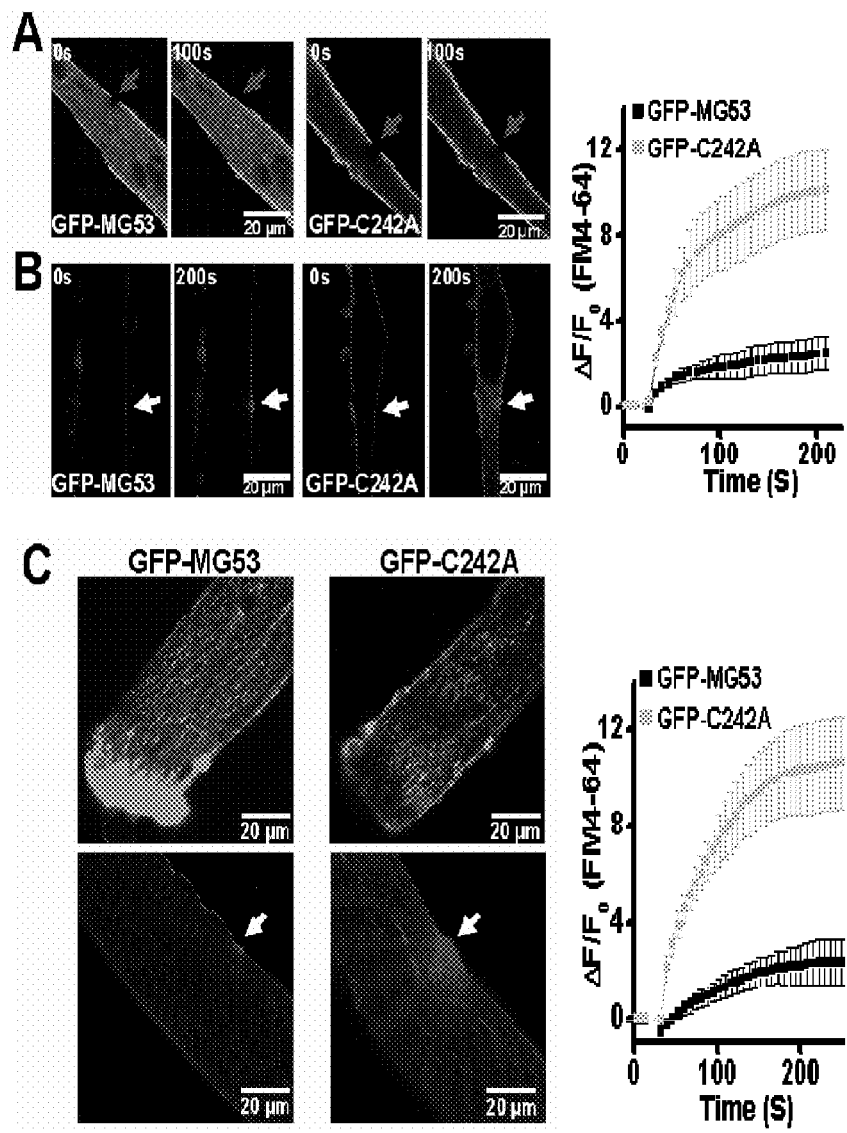

FIG. 17. MG53-mediated repairsome formation and restoration of acute sarcolemma membrane damage. (A) Entry of FM4-64, a red-shifted variant of FM1-43, was used as an index of membrane repair capacity in mg53−/− myotubes transfected with GFP-MG53 and GFP-C242A. Following UV-bleaching of the green fluorescence, rapid translocation of GFP-MG53 took place at the injury site, whereas GFP-C242A remained static due to its defective oligomerization properties. Significantly less entry of FM4-64 was observed in cells transfected with GFP-MG53 compared with GFP-C242A, suggesting that the mutant was not able to restore membrane integrity following injury (B). Oligomerization of MG53 appears to be a step in repairsome formation, as the GFP-C242A mutant expressed in wt skeletal muscle displayed a dominant negative function over the native MG53 (C). Compared with GFP-MG53, overexpression of GFP-C242A in adult wt muscle fibers inhibited sarcolemmal membrane repair function (C).

FIG. 18. Ubiquitination, in vitro, catalyzed by MG53. A recombinant maltose-binding protein (MBP) fusion protein for MG53 (MBP-MG53) was incubated with ATP, ubiquitin, E1 and E2 enzymes, and subjected to immunoblotting with the anti-MBP antibody. High molecular-mass ladders derived from ubiquitination were observed when MBP-MG53 was incubated with Ubc4 or UbcH5 as E2 (a). The intrinsic E3-ligase activity of MG53 was significantly reduced in C29L mutant (b). (c) Western blot demonstrated that the full-length GFP-MG53 and GFP-C29L proteins were present in the differentiated C2C12 myotubes, thus the C29L mutant is stable and it is unlikely that degradation of these fusion proteins contributes to the different subcellular distribution of GFP-C29L.

GFP-C29L displays predominantly a cytosolic pattern in C2C12 myotubes (d, left). Western blot demonstrated that the full-length GFP-MG53 and GFP-C29L proteins were present in the differentiated C2C12 myotubes (c), thus it is unlikely that degradation of these fusion proteins contributes to the different subcellular distribution of GFP-C29L and GFP-MG53 observed in (d). Similar phenomena were observed with transient expression of these fusion proteins into primary cultured skeletal myotubes derived from the mg53−/− neonates, where targeting of GFP-MG53 to sarcolemmal membrane and intracellular vesicles were attenuated for the GFP-C29L mutant (d, right). Following acute membrane damage, rapid accumulation of GFP-MG53 is observed in C2C12 myoblasts, whereas GFP-C29L appeared to be immobile and ineffective in repair of membrane injury (e, left). Similar defects with GFP-C29L were also observed in C2C12 myotubes (e, middle). Moreover, while GFP-MG53 could translocate to the plasma membrane following injury in primary cultured mg53−/− myotubes, GFP-C29L expressed in these cells remained generally unresponsive to acute cell injury (e, right).

Figure 19:
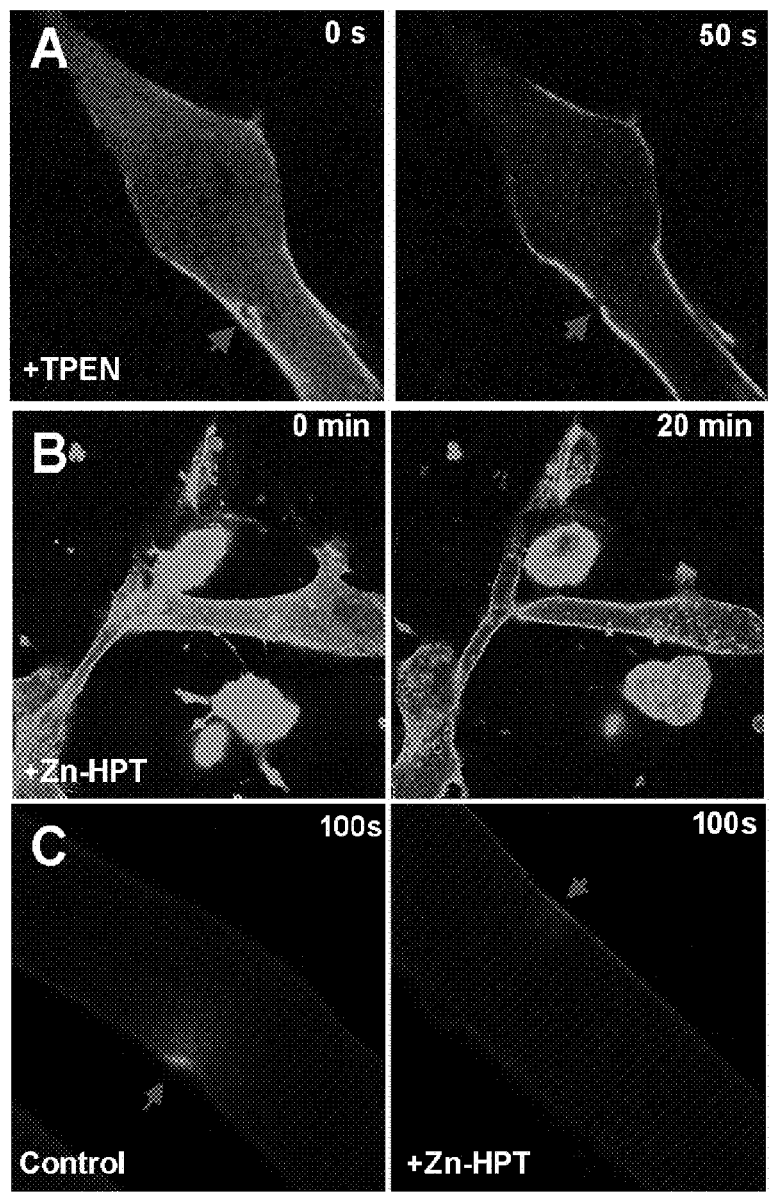

FIG. 19. Effect of removing zinc (Zn) from the extracellular solution before wounding C2C12 myoblasts expressing GFP-MG53. Chelating Zn with N,N,N,N-tetrakis(2-pyridylmethyl)ethylenediamine (TPEN) could prevent the translocation of GFP-MG53 to the site of microelectrode penetration (A), indicating that Zn was necessary for MG53 function. Addition of a Zn ionophore, Zn-1-hydroxypyridine-2-thine (Zn-HPT), could induce the translocation of GFP-MG53 in C2C12 cells (B). Wild type FDB muscle fibers: +Zn-HPT reduces the amount of FM-1-43 dye that can enter the muscle fiber following injury induced by a UV laser (C).

FIG. 20. Protective effect of zinc on membrane repair is lost in mg53−/− skeletal muscle. (a) individual flexor digitorum brevis (FDB) muscle fibers were isolated from wild type (WT) mice (3-6 months). A strong UV laser was applied to the FDB fiber that caused local damage to the muscle (arrow). Entry of FM1-43 fluorescent dye (2.5 µM) was used as an indicator for the measurement of membrane repair capacity. The images were taken 200 s following UV irradiation (control). Application of 2 µM zinc-ionophore (1-hydroxypyridine-2-thione) (+Zn-HPT) led to increased membrane repair capacity as reflected by the decreased amount of FM1-43 dye entry following UV-damage. Addition of 40 µM TPEN (Tetrakis-2-pyridylmethylenediamine), a specific buffer for zinc ions, led to compromised membrane repair capacity, as reflected by the significant increase in FM1-43 dye entry following UV-damage (+TPEN). (b) FDB muscle fibers isolated from the mg53−/− mice (3-6 months) exhibited defective membrane repair function, as shown by the elevated amount of FM1-43 dye entry following identical treatment of UV-damage (control). (c) with Ca-EDTA (100 µM), a reagent that buffers zinc without altering extracellular Ca concentration, also caused compromised membrane repair capacity in WT muscle (left). Treatment with Ca-EDTA did not produce any significant changes in membrane repair capacity in mg53−/− muscle. (d) Schematic diagram of zinc-binding motifs in MG53. The amino-terminus of MG53 contains two putative zinc-binding motifs: one located at the RING motif (a.a. 1-56, human cDNA), and the other located at the B-box motif (a.a. 86-117, human cDNA). The specific amino acids that participate in zinc-binding are indicated.

FIG. 21. Extracellular zinc entry facilitates MG53-mediated vesicle translocation to acute membrane injury sites. a) GFP-MG53 fusion protein was expressed in C2C12 myoblast cells. GFP-MG53 displayed localization at the intracellular vesicles and the plasma membrane under resting condition (left). Acute injury of the cell generated by penetration of a microelectrode (arrow, right panel). b) Incubation of the C2C12 cell with 40 µM Ca-EDTA. c) Addition of 20 µM TPEN to the extracellular solution. d) C2C12 cells transiently transfected with GFP-MG53 were incubated with 20 µM Zn-HPT. Under control condition (0 min), prolonged incubation with Zn-HPT (15 min). e) Summary data with Ca-EDTA and TPEN on GFP-MG53 mediated membrane repair in C2C12 myoblast cells.

Figure 22:
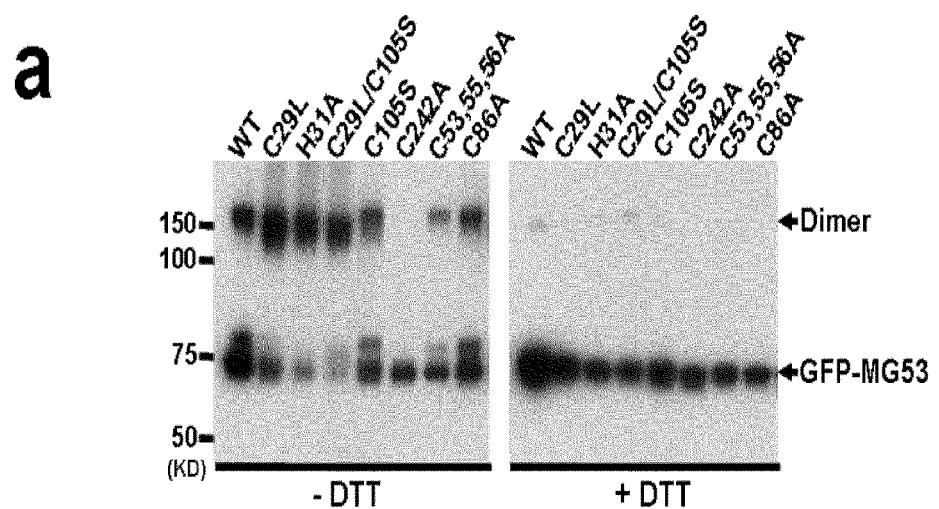

FIG. 22. Zn-binding to RING and B-box motifs of MG53. a) site-specific mutations in the RING and B-box motifs of MG53 transiently expressed in C2C12 myoblast cells. 24 hours after transfection, the cells were harvested and the expression of the various GFP-MG53 mutants was assayed by Western blot with specific antibody against MG53; in the absence of DTT (left panel). Oligomeric patterns are marked "dimer." With the addition of 10 mM DTT, all mutant constructs displayed monomeric forms of ~75 kD (predicted molecular size of GFP-MG53).

FIG. 23. MG53 can bind Zn through a RING motif. (a) MG53 contains a canonical TRIM domain that contains a Zn binding motif (Ring) and a Bbox motif. (b) Bacterial culture was lysed by sonication, centrifuged and bound to Amylose resin in column buffer containing 10 uM zinc for overnight at 4 degrees. The resin was then washed by zinc free column buffer followed by 50 ml of zinc free column buffer with 0.3 mM maltose. Protein levels and stability were confirmed by SDS-PAGE gel as shown. Lane 1 (Marker), Lane 2 (mMG53), Lane 3 (mC29L-MG53 mutant), Lane 4 (mC29L/C105S double mutant DM clone1) Lane 5 (mC29L/C105S double mutant DM clone2), Lane 6 (10 mg/ml BSA), Lane 7 (5 mg/ml BSA), Lane 8 (2.5 mg/ml BSA), Lane 9 (1 mg/ml BSA). (c) The proteins on beads were first tested for the presence of free zinc in the solution (from 0.01 to 0.1 uM or ND depending on the preparation). The beads (aliquot) were stained with a zinc-specific probe TSQ and fluorescence was observed under the fluorescent microscope and relative fluorescence intensity taken. Then the proteins were denatured at 56 C for 5 mM, vortexed, centrifuged, and the measurements were taken again from the solution. The assay uses TSQ (Mol Probe) and an atomic standard solution of zinc (Sigma) for calibration. Chart indicates the amount of Zn binding to recombinant wild type (WT) MG53, C29L mutant (C29L) and double mutant (DM). Both mutants are located in the Ring motif of the TRIM domain. Data presented as mean±S.D. *$P<0.05$, **$P<0.001$ compared to wt; n=4~5.

Figure 24:
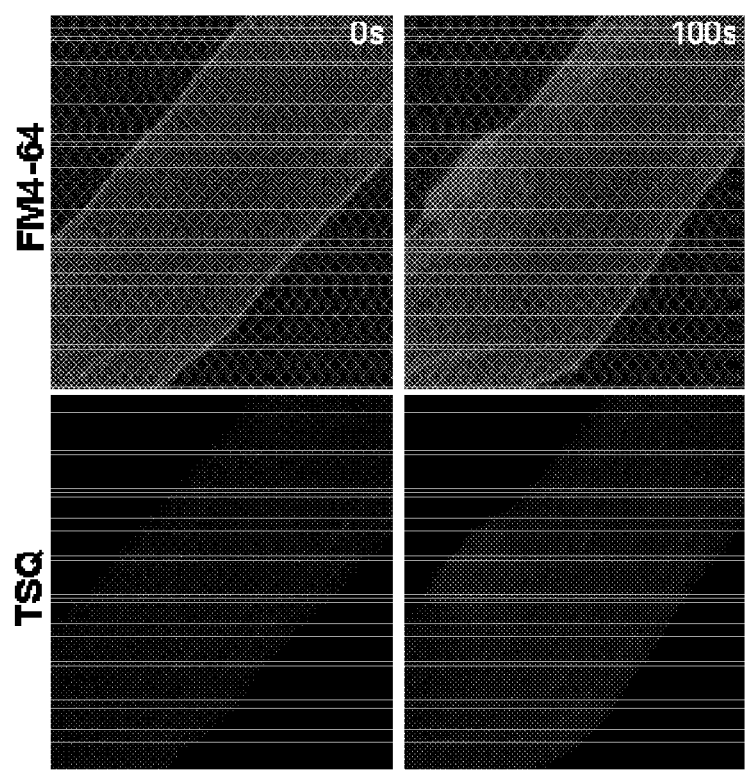

FIG. 24. FDB muscle fibers isolated from the wild type mice were loaded with 2 μM TSQ, a specific fluorescent indicator for zinc in the intracellular solution (lower panels). A strong UV-laser was used to cause local damage to the FDB muscle fiber, as reflected by the accumulation of FM4-64 fluorescent day at the local injury site (top panels). Notice that significant elevation of TSQ fluorescence (and therefore more zinc) was observed at the acute injury site.

Figure 25:
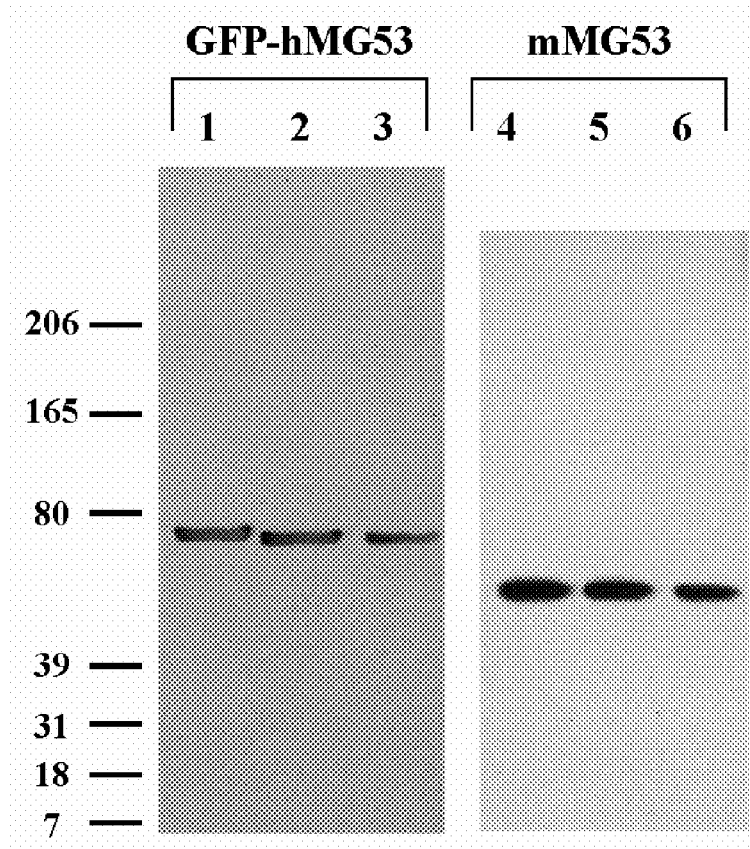

FIG. 25. Monoclonal antibody against hMG53 isolated from hybridoma (mAb 4A3F6F2) is highly effective at detecting human (and mouse) MG53 protein on a Western blot.

Figure 26:
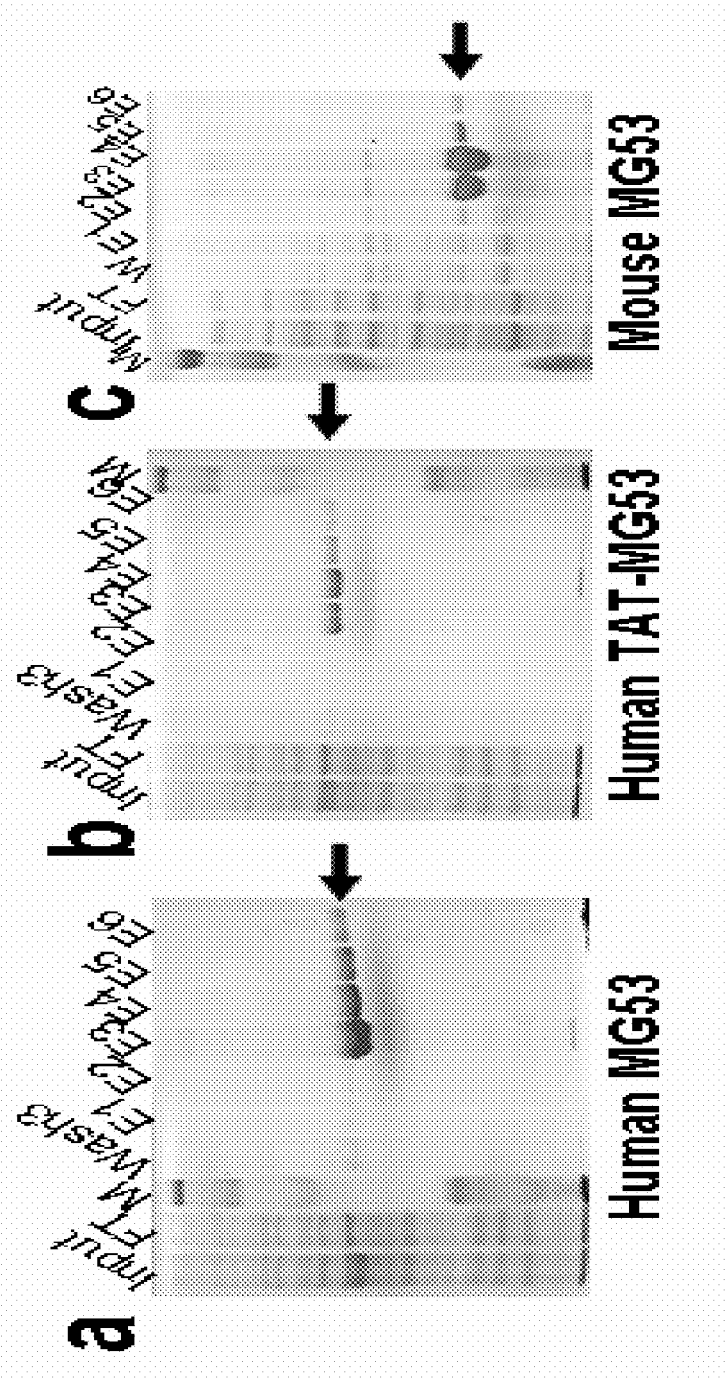

FIG. 26. Recombinant expression of MG53. (a) Coomassie blue stained gel of recombinant human MG53 protein (arrow) fractions isolated from Sf9 insect cells with a Ni-NTA column. Input=cell extract, FT=flow through, M=marker, E=elution number. (b) Coomassie blue stained gel of recombinant human TAT-MG53 (arrow) isolated from Sf9 insect cells. (c) Coomassie blue stained gel of recombinant mouse TAT-MG53 (arrow) isolated from *E. coli* fermentation.

Figure 27:
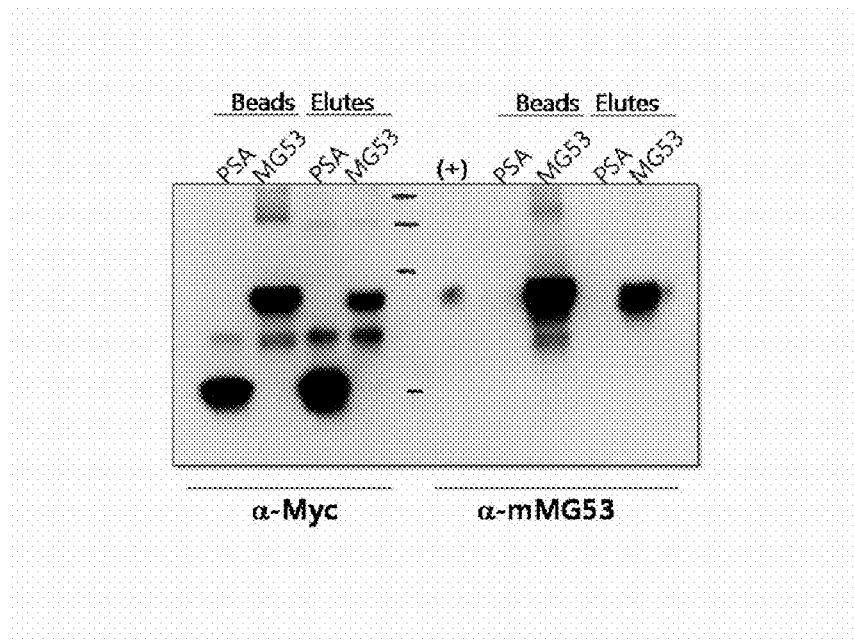

FIG. 27. Illustrates that a signal-peptide at the amino-terminus of hMG53 allows export of the recombinant MG53 as a secretory protein. Western blot shows that abundant MG53 protein could be purified from conditioned media with CHO cells that are transiently transfected with the engineered hMG53 cDNA.

Figure 28:
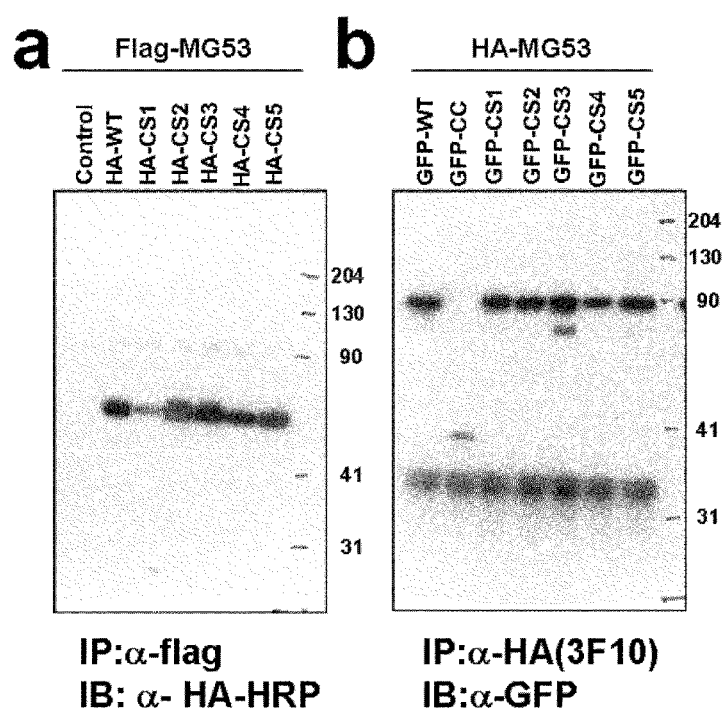

FIG. 28. Co-immuno-precipitation (Co-IP) experiments in HEK293 cells transfected with a Flag-MG53 fusion protein construct and a series of HA-MG53 fusion protein mutants. (a) Co-IP was performed with an anti-Flag antibody on whole cell extracts followed by Western blot with an anti-HA antibody. (b) Co-IP experiments show that formation of MG53 dimers requires the presence of the coiled-coil domain.

Figure 29:
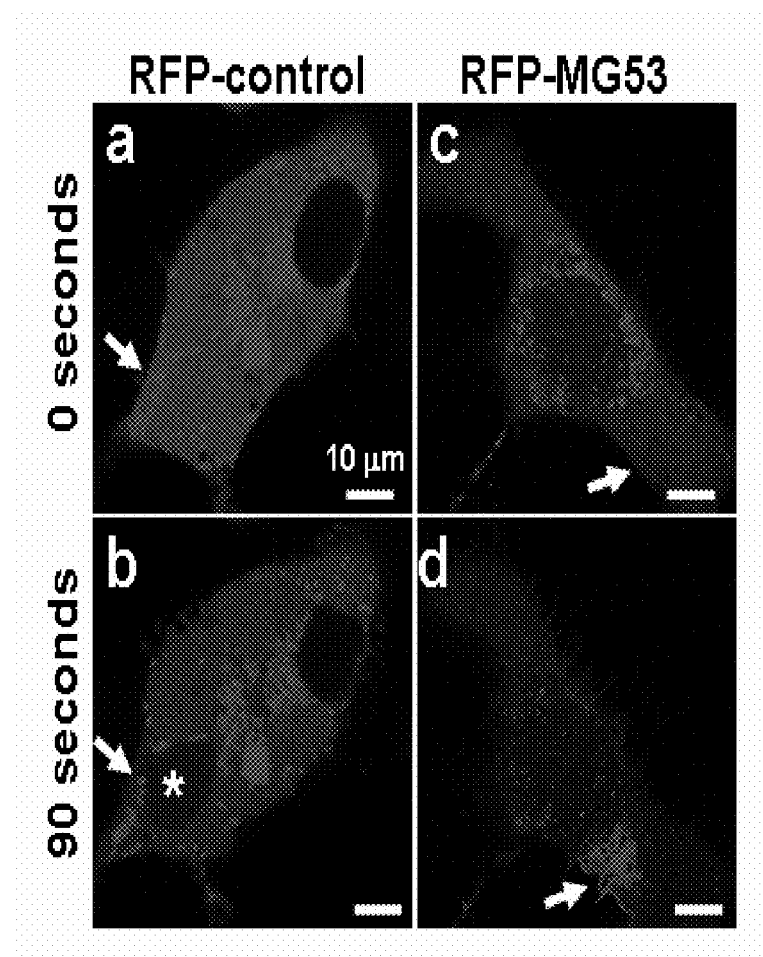

FIG. 29. Stable HEK293 (Human Embryonic Kidney) cell lines expressing RFP-MG53. (a) Cell lines that stably express an RFP (red fluorescent protein) control protein that shows a cytosolic expression pattern. (b) Injury of HEK293 cells expressing RFP only with a microelectrode results in no translocation of RFP to the injury site (arrow). Some bleaching of RFP fluorescence occurs from excessive entry of extracellular buffer (*). (c) HEK293 cells that are stably expressing RFP-MG53 show localization to intracellular vesicles. (d) Injury of HEK293 cells expressing RFP-MG53 results in massive translocation of MG53 to the injury site (arrow) in less than 90 seconds.

FIG. 30. GFP-MG53 expressed in C2C12 cells, followed by perfusion with an alcohol extract from *notoginseng*. Application of *notoginsing* can rapidly induce MG53 translocation to the plasma membrane within 2 min after perfusion.

Figure 31:
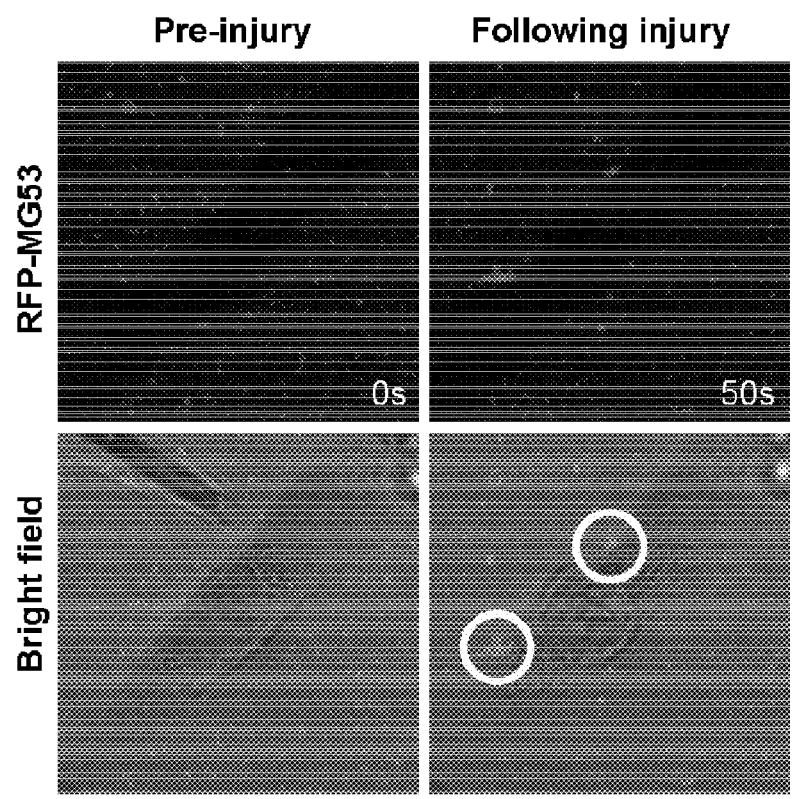

FIG. 31. Therapeutic use of recombinant MG53 as a tissue repair reagent. RFP-MG53 (a MG53 fusion protein that contains a red fluorescent protein) was expressed in HEK293 cells, isolated, and applied to the external media surrounding C2C12 myoblasts in culture. Cells were mechanically wounded with a microelectrode while the localization of the fusion protein was observed by confocal microscopy. RFP-MG53 can be observed to translocate to such sites of membrane damage (circles).

Figure 32:
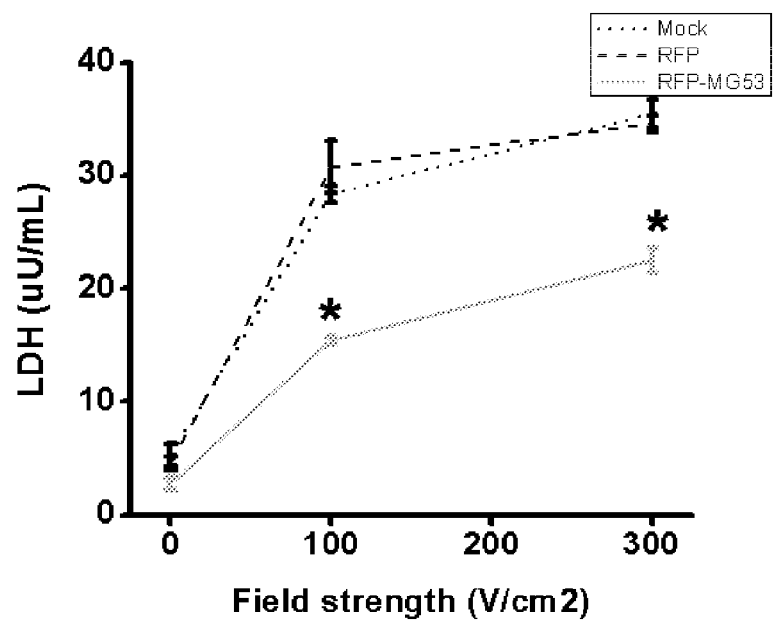

FIG. 32. Genetic overexpression of MG53 prevents membrane damage. Human embryonic kidney (HEK293) cells were transfected with RFP-MG53 or RFP and then electroporated with fields of varying strength. The amount of membrane damage was measured by assessing the amount of lactate dehydrogenase (LDH) that leaks into the extracellular media out of holes in the plasma membrane produced by electroporation. The more damage that occurs to the membrane, the higher the reading on the LDH assay will be.

Figure 33:
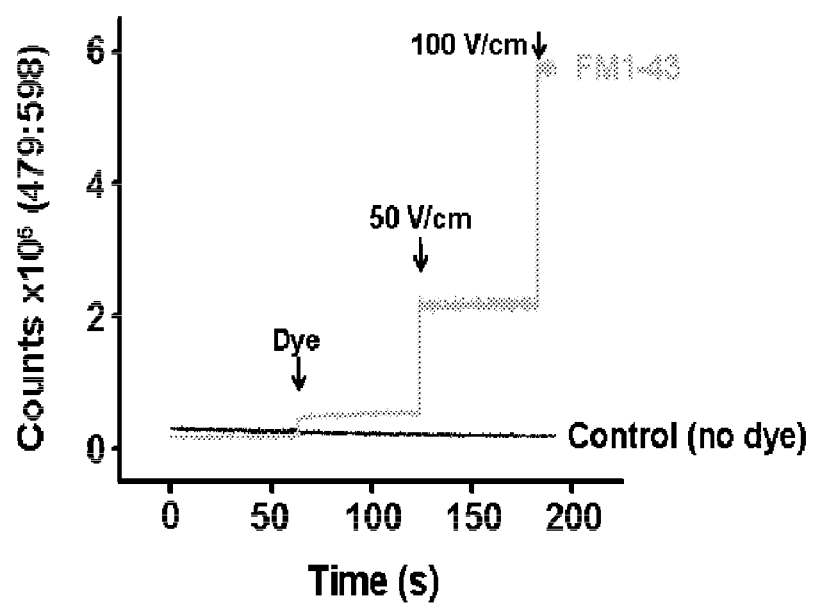

FIG. 33. Fluorescent dye entry used to measure membrane damage following electroporation. Human embryonic palatal mesenchymal (HEPM) cells (1×10^6) were placed in a spinning cuvette of a PTI fluorescence system. FM1-43 day was added outside of the cells and displayed minimal fluorescence with an excitation of 479 nm and an emission of 598 nm. When cells were electroporated with a field strength of 50 V/cm or 100 V/cm there was a dose dependent increase in fluorescence detected. Electroporation does not produce auto-fluorescence in cells where the dye is not present (control).

Figure 34:
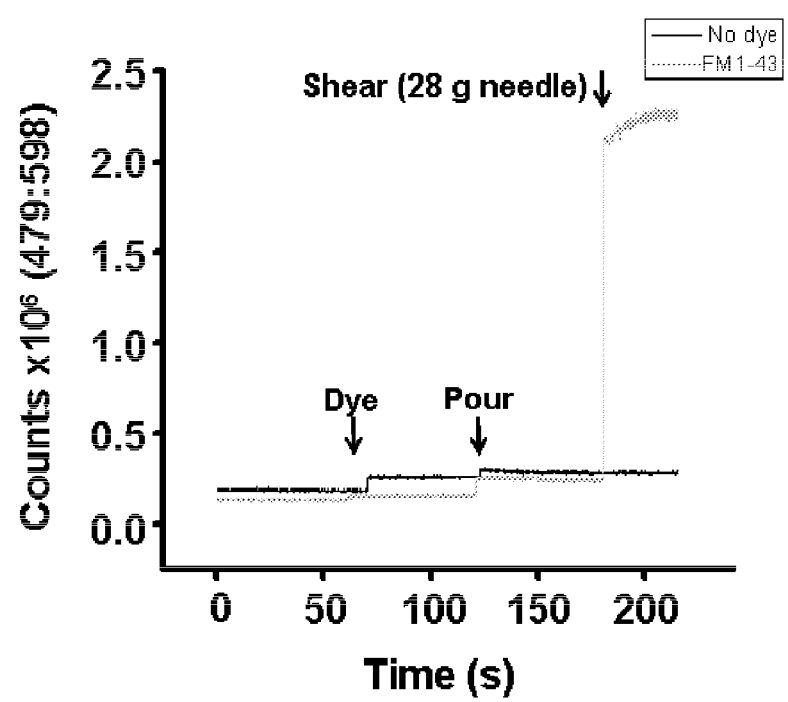

FIG. 34. Fluorescent dye entry used to measure membrane damage following mechanical damage. Human embryonic palatal mesenchymal (HEPM) cells (1×10^6) were placed in a spinning cuvette of a PTI fluorescence system. FM1-43 day was added outside of the cells and displayed minimal fluorescence with an excitation of 479 nm and an emission of 598 nm. Cells were removed from the cuvette (Pour) sheared with a 28 gauge needle (Shear), leading to an increase in FM1-43 fluorescence. Mechanical shear stress does not produce auto-fluorescence in cells where the dye is not present as a control (No dye).

Figure 35:
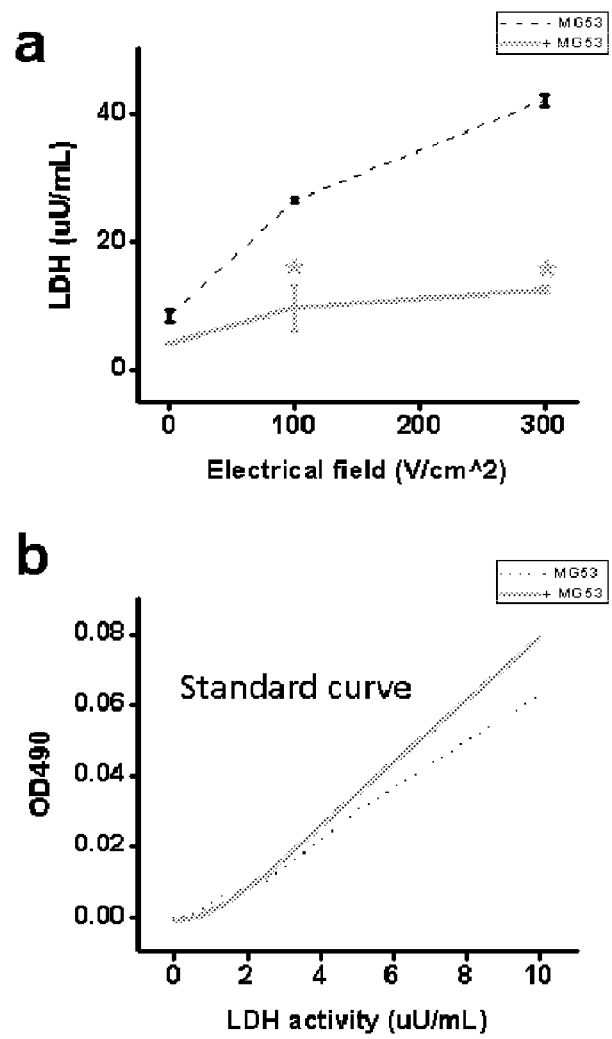

FIG. 35. Recombinant MG53 protects kidney cells from cell membrane damage. (a) HEK293 cells (8×10^4) were treated with 10 ug/mL recombinant human MG53 or vehicle control and then electroporated at various field strengths. Extracellular recombinant MG53 can prevent damage from electroporation. (b) MG53 or a vehicle control was added to recombinant LDH to generate standard curves for LDH activity.

Figure 36:
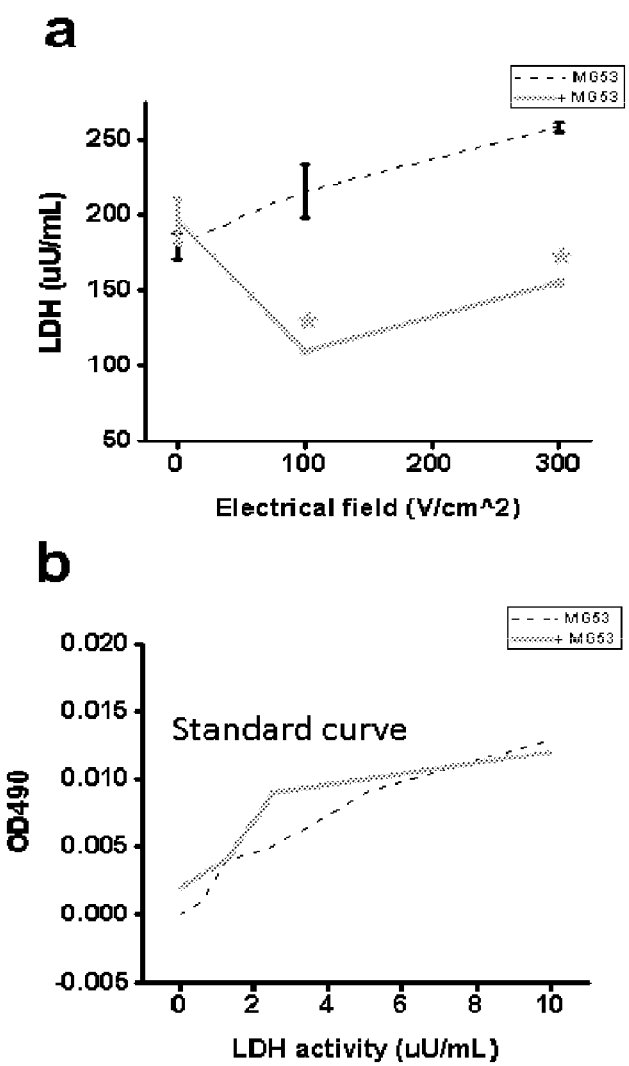

FIG. 36. Recombinant MG53 protects gum lining cells from cell membrane damage. (a) HEPM cells (5×10^4) were treated with 10 ug/mL recombinant human MG53 or vehicle control and then electroporated at various field strengths. Extracellular recombinant MG53 can prevent damage from electroporation. (b) MG53 or a vehicle control was added to recombinant LDH to generate standard curves for LDH activity.

Figure 37:
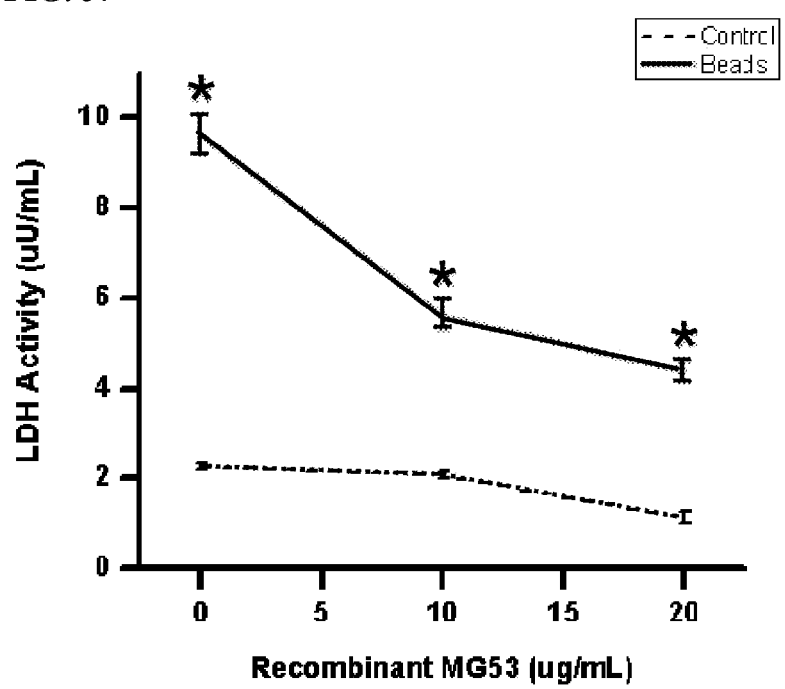

FIG. 37. Recombinant MG53 protects kidney cells from mechanical cell membrane damage. HEK293 cells (8×10^4) were treated with glass microbeads to induce mechanical damage. Different doses of recombinant human MG53 or vehicle control was applied to the samples when glass beads were added to the media. Cells were rotated on an orbital shaker and then the supernatant was analyzed for LDH levels.

Figure 38:
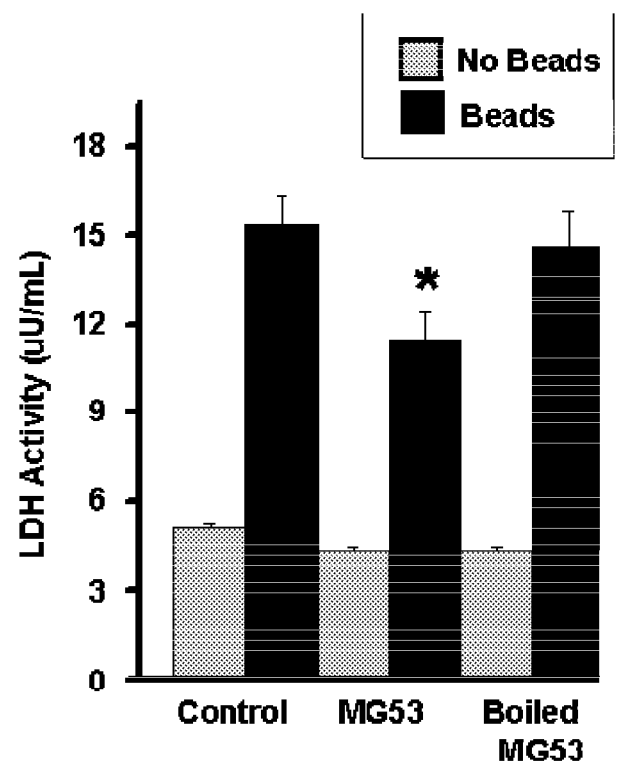

FIG. 38. Effects of MG53 are specific to the function of the protein. MG53 proved to be effective at resealing damage in Hela cervical epithelial cells that was produced due to exposure to glass beads. When the recombinant protein is boiled the protein can no longer facilitate membrane resealing.

Figure 39:
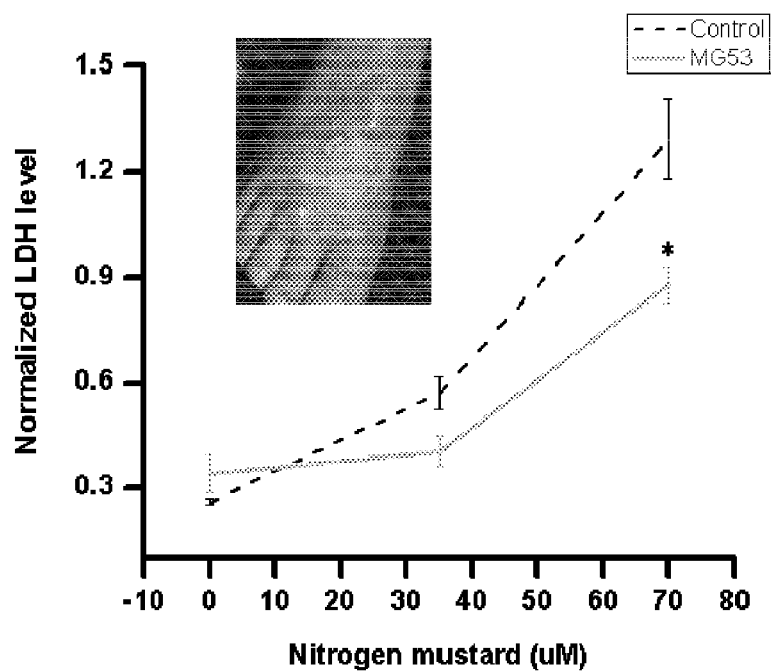

FIG. 39. Membrane damage to human keratinocytes induced by nitrogen mustard prevented by MG53. Various doses of nitrogen mustard, a skin blistering agent, can produce LDH release from primary human keratinocytes. Inset picture illustrates the effects of exposure to a skin blistering agent.

Figure 40:
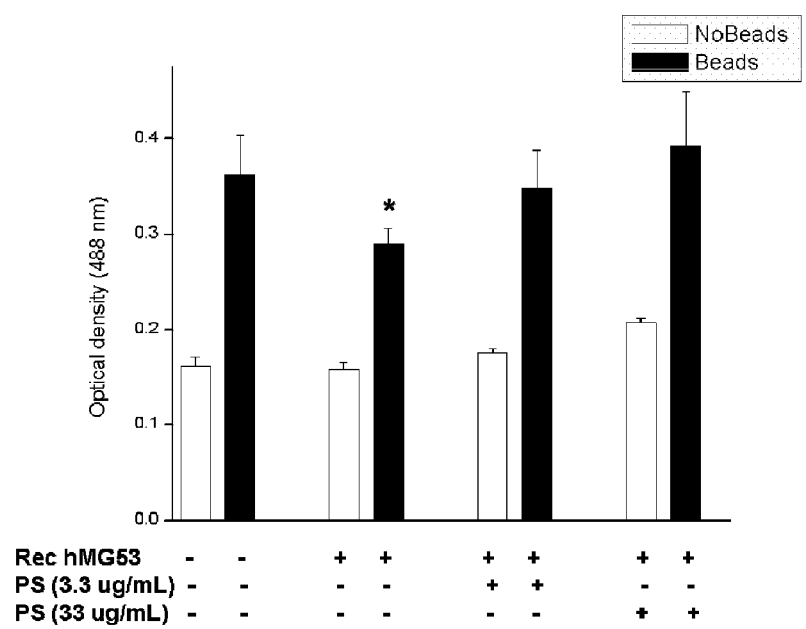

FIG. 40. Externally applied recombinant MG53 requires phosphatidylserine (PS) binding to reseal damaged membranes. HEK293 cells were treated with recombinant human MG53 or vehicle and them damaged by shaking in the presence of glass microbeads (black bars). Membrane damage is measured by LDH release from cells that is recorded by colormetric assay recorded at 488 nm. Simultaneous treatment of cells with phosphatidylserine (PS) can prevent resealing of plasma membrane. * $p<0.05$ FIG. 41. Competition with another phosphatidylserine (PS) binding protein. HEK293 cells were treated with recombinant human MG53 or vehicle and them damaged by shaking in the presence of glass microbeads (black bars). Membrane damage is measured by LDH release from cells that is recorded by colormetric assay recorded at 488 nm. Simultaneous treatment of cells with an excess (5:1) of a phosphatidylserine (PS) binding protein, and Annexin V. * $p<0.05$ FIG. 42. Expression of MG53 in human embryonic palatal mesenchymal (HEPM) dental cells. GFP-MG53 localizes properly in these cell types, it also effectively translocates to the plasma membrane following membrane damage by either physical penetration of a microelectrode or treatment with saponin detergent.

Figure 43:
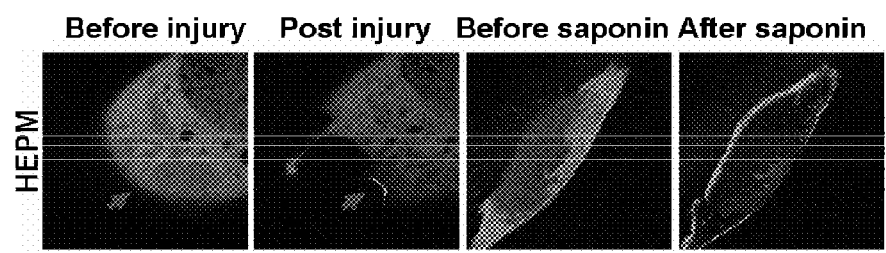

FIG. 43. Expression of MG53 in human embryonic palatal mesenchymal (HEPM) dental cells. GFP-MG53 localizes properly in these cell types, it also effectively translocates to the plasma membrane following membrane damage by either physical penetration of a microelectrode or treatment with saponin detergent.

Figure 44:
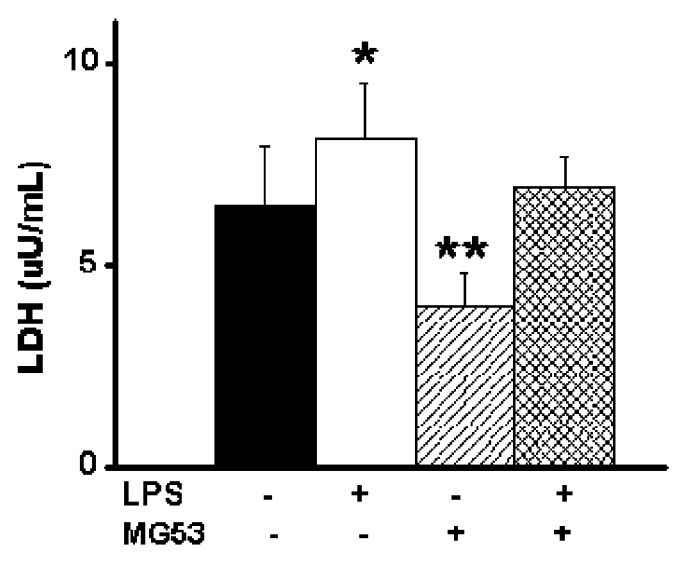

FIG. 44. Lipopolysaccarides induce membrane damage in HEPM cells prevented by exposure to MG53. When HEPM cells are treated with LPS (1 mg/mL) for 24 hours LDH release can be observed, suggesting that membrane damage has occurred. Application of MG53 can prevent the normal levels of LDH release from the HEPM cells, while co-incubation with LPS and MG53 shows normal release of LDH from cells.

Figure 45:
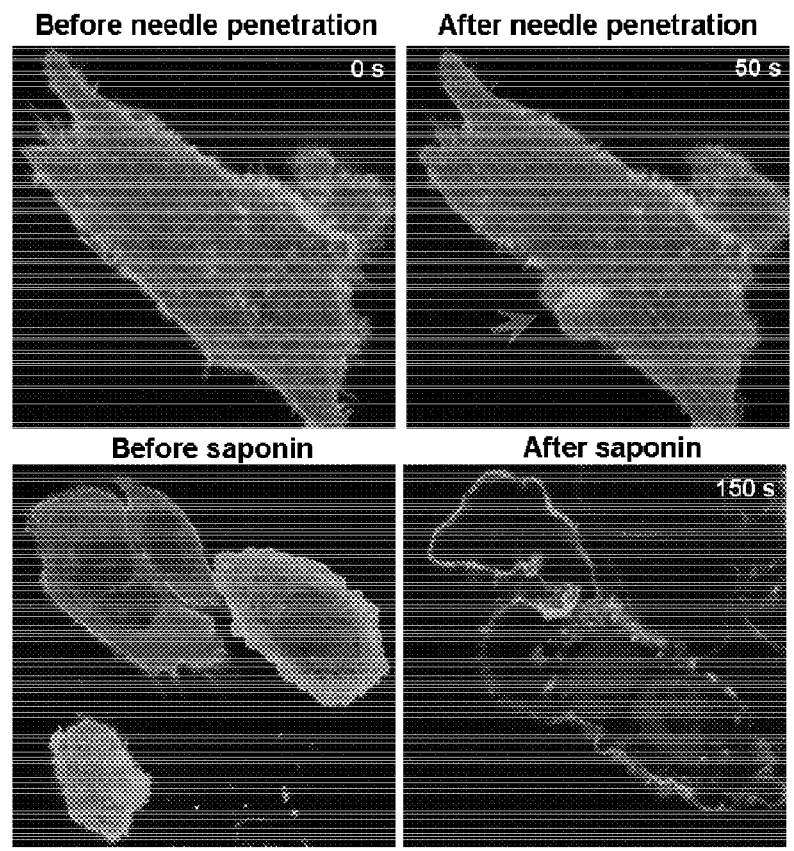

FIG. 45. MG53 translocates to membrane repair sites in gastric cells. Human gastric adenocarcinoma (AGS) cells were transfected with GFP-MG53 and then subjected to mechanical membrane damage by microelectrode needle penetration (top) or treatment with 0.005% saponin to permeabilize the membrane (bottom). Translocation of GFP-MG53 to the injury site (arrow) was monitored by live cell confocal microscopy.

Figure 46:
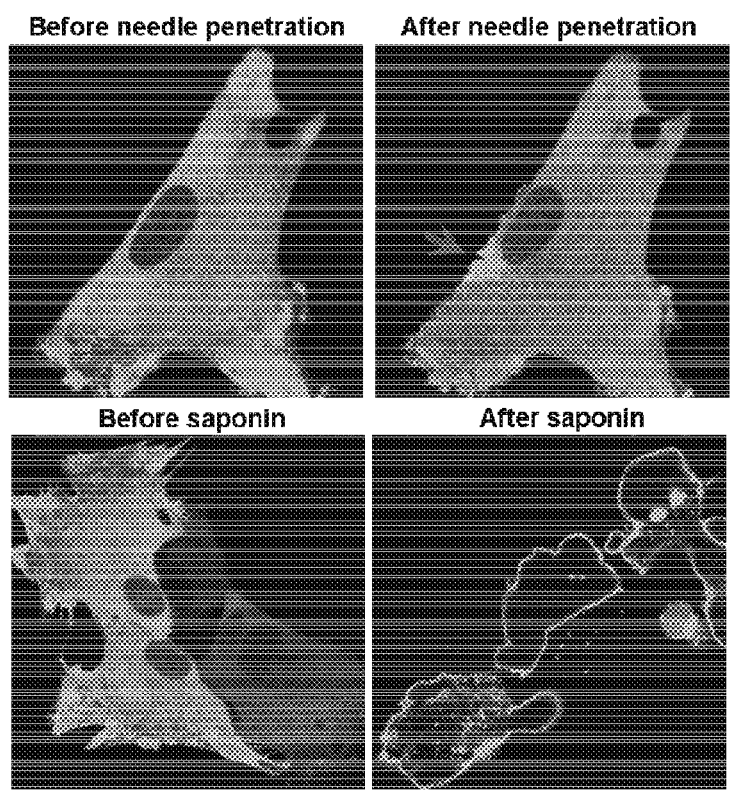

FIG. 46. MG53 translocates to membrane repair sites in neural cells. Mouse primary astrocytes were transfected with GFP-MG53 and then subjected to mechanical membrane damage by microelectrode needle penetration (top) or treatment with 0.005% saponin to permeabilize the membrane (bottom). Translocation of GFP-MG53 to the injury site (arrow) was monitored by live cell confocal microscopy.

Figure 47:
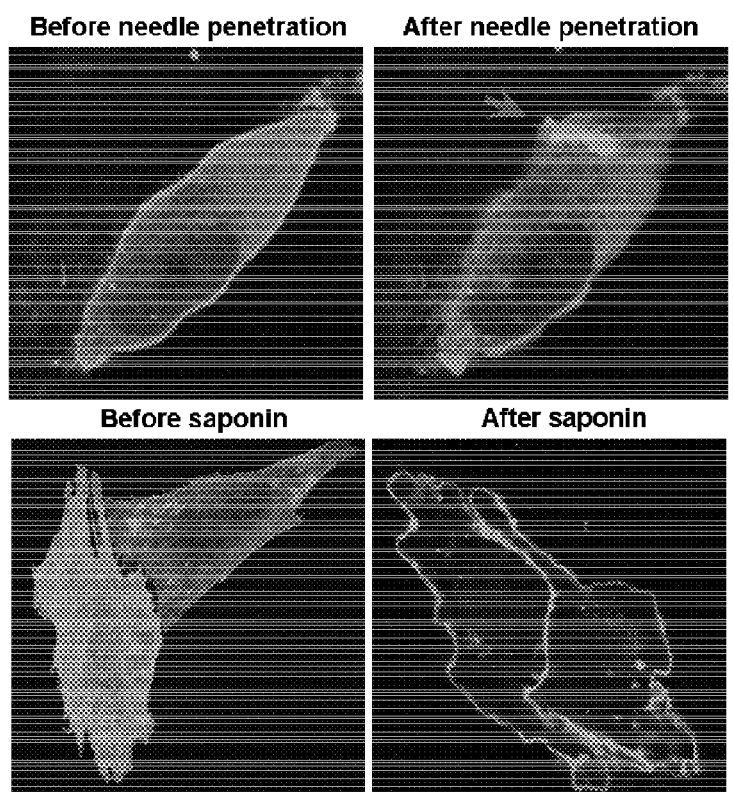

FIG. 47. MG53 translocates to membrane repair sites in airway epithelial cells. Human C38 airway epithelial cells were transfected with GFP-MG53 and then subjected to mechanical membrane damage by microelectrode needle penetration (top) or treatment with 0.005% saponin to permeabilize the membrane (bottom). Translocation of GFP-MG53 to the injury site (arrow) was monitored by live cell confocal microscopy.

Figure 48:
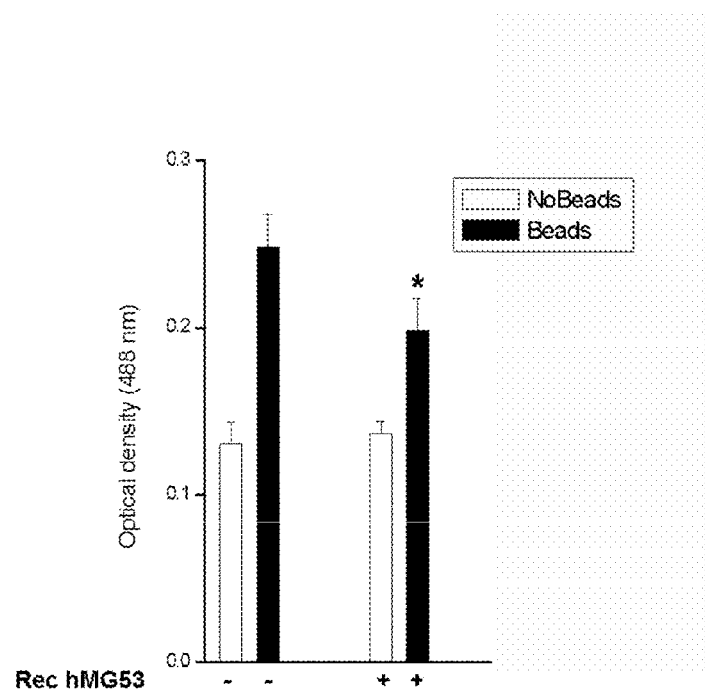

FIG. 48. External MG53 reseals membrane damage in airway epithelial cells. Human IB3 airway epithelial cells were treated with external recombinant human MG53 or vehicle control and then exposed to mechanical membrane damage by glass beads. Membrane damage is measured by LDH release from cells that is recorded by colormetric assay recorded at 488 nm. * $p<0.05$ FIG. 49. MG53 translocates to membrane repair sites in immune cells. Mouse leukaemic monocyte macrophage (RAW 264.7) cells were transfected with GFP-MG53 and then subjected to mechanical membrane damage by microelectrode needle penetration (top) or treatment with 0.005% saponin to permeabilize the membrane (bottom). Translocation of GFP-MG53 to the injury site (arrow) was monitored by live cell confocal microscopy.

Figure 50:
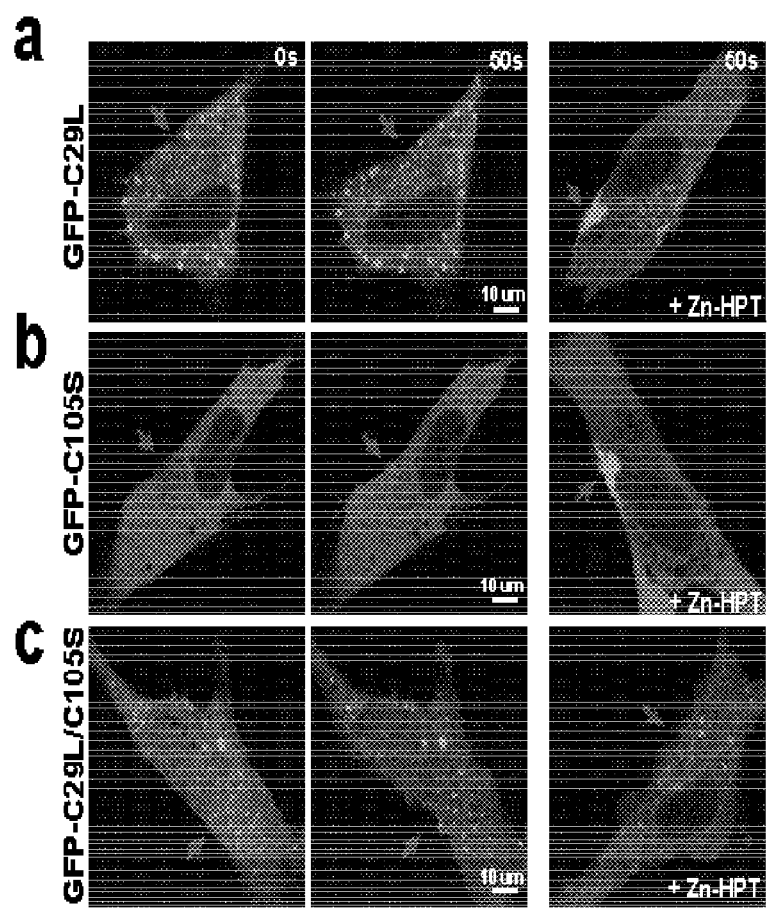

FIG. 50. a) GFP-C29L mutant expressed in C2C12 cells (left panel) displayed defective movement toward the acute injury site (middle panel), in an extracellular solution that contain nominal free zinc. Addition of 2 μM Zn-HPT, which serves as ionphore for zinc entry across the plasma membrane, could partially rescue the movement of GFP-C29L toward the acute injury site (right panel). The image presented in the right panel was obtained from a separate C2C12 cell, 50 s after penetration with a microelectrode with 2 μM Zn-HPT present in the extracellular solution. b) GFP-C105S mutant expressed in C2C12 cells (left panel) could not move to the acute injury site following microelectrode penetration (middle panel), in an extracellular solution that contain nominal free zinc. c) GFP-C29L/C105S double mutant expressed in C2C12 cells (left panel) is completely defective in repair of acute membrane damage, under conditions with nominal free zinc (middle panel) or following addition of 2 μM Zn-HPT (right panel).

Figure 51:
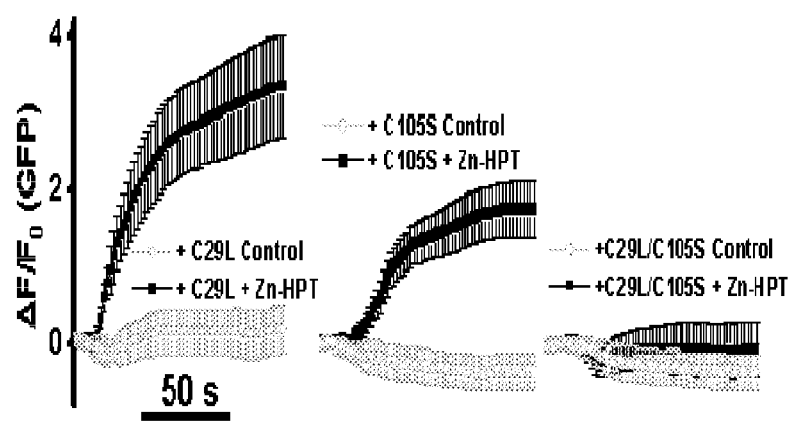

FIG. 51. Summary data for the dependence of C29L, C105S, and C29L/C105S on zinc entry in repair of acute membrane damage in C2C12 cells. Data with other mutants of MG53 are summarized in Table 1.

Figure 52:
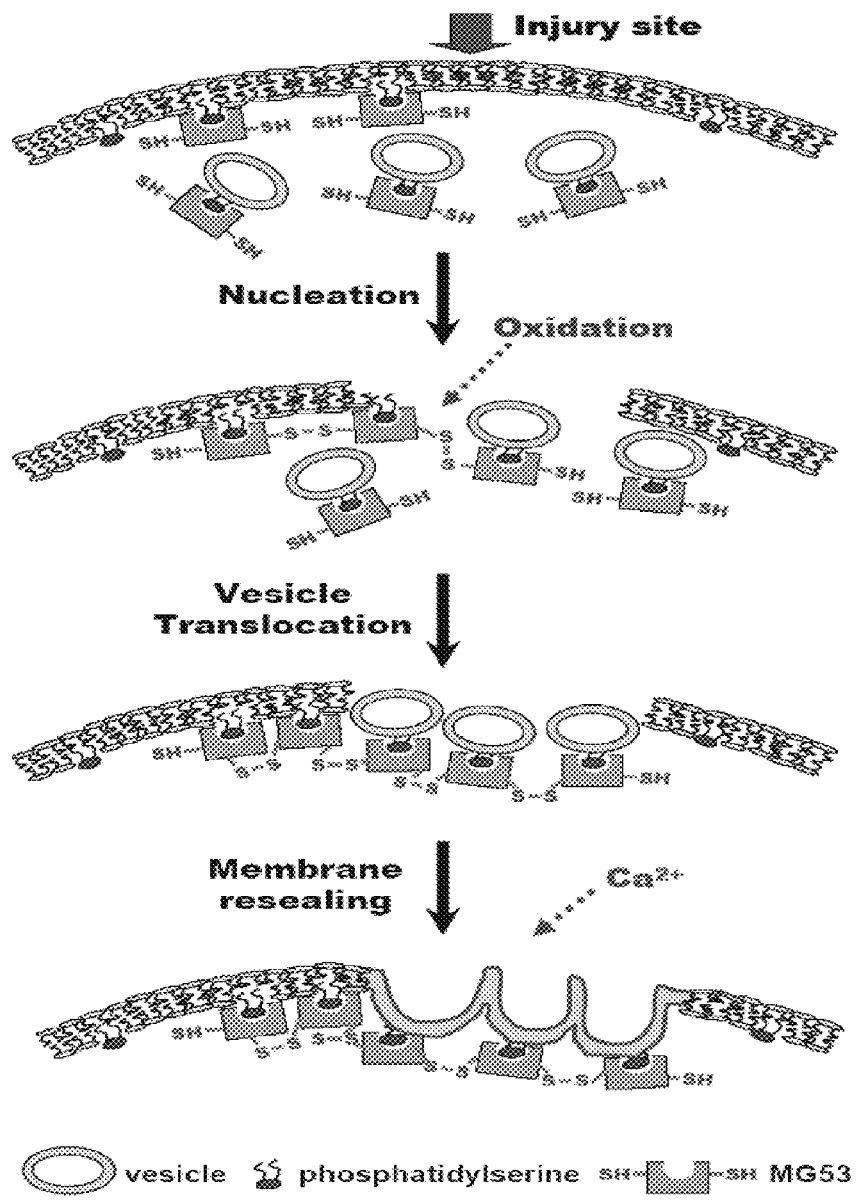

FIG. 52. Illustration demonstrating the inventors' current hypothesis on the mechanism of membrane repair mediated by MG53. While not being limited to any particular theory, experimental evidence indicates that MG53 is likely localized to the inner surface of the plasma membrane due to its association with phosphatidylserine-containing vesicles. Under normal conditions MG53 is likely monomeric and sequestered proximal to the membrane surface due to associations with caveolin-3. Following damage to the cellular membrane MG53, which is normally in its reduced form, is exposed to a localized oxidative environment which triggers the formation of disulfide cross-bridges and intermolecular MG53 oligomerization. The oligomerization of MG53 brings phosphatidylserine-containing vesicles together at the damage site.

DETAILED DESCRIPTION

The present specification incorporates herein by reference WO 2008/054561; Cai et al., MG53 nucleates assembly of cell membrane repair machinery. *Nature Cell Biol.*, 11(1): p 56-64 (January 2009); and Cai et al., MG53 regulates membrane budding and exocytosis in muscle cells. Journal of Biological Chemistry., published online Nov. 24, 2008, in their entirety for all purposes.

The invention is related, in part, to the surprising and unexpected discovery of recombinant nucleic acid sequences and related polypeptides (See, SEQ ID NOs.: 1-15), which are capable of facilitating the repair of cell membranes. In particular, the inventors discovered that vesicular fusion during acute membrane repair is driven by mitsugumin53 (MG53) (SEQ ID NOs. 1-15), a novel muscle-specific tri-partite motif (TRIM) family protein. MG53 expression facilitates intracellular vesicle trafficking to and fusion with the plasma membrane.

Dynamic membrane repair is essential not only for long-term maintenance of cellular integrity but also for recovery from acute cell injury. Repair of the cell membrane requires intracellular vesicular trafficking that is associated with accumulation of vesicles at the plasma membrane. Acute injury of the cellular membrane leads to recruitment of MG53-containing vesicles to patch the membrane at the injury site. Cells that are null for MG53 display defects in membrane repair in response to multiple stresses, including laser-induced injury, muscle damage induced by exercise, and compromised recovery of muscle contractile function after fatigue. Thus, MG53 is a key component of the vesicular trafficking events that underlie the acute repair and remodeling of cellular membranes.

The biopolymer compositions encompassed by the invention are collectively and interchangeably referred to herein as "MG53 nucleic acids" or "MG53 polynucleotides" or "nucleic acids encoding membrane repair polypeptides" or "membrane repair protein nucleic acids," and the corresponding encoded polypeptides are referred to as "MG53 polypeptides" or "MG53 proteins" or "membrane repair polypeptides." Unless indicated otherwise, "MG53" is used generally to refer to any MG53 related and/or MG53-derived biopolymers as explicitly, implicitly, or inherently described herein. Also, as used herein, "membrane repair polypeptides" and "polypeptides facilitating membrane repair" are used interchangeably to refer to the polypeptides of the invention and their biological activity.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In the case of conflict, the present specification, including definitions, will control. In addition, the materials, methods, and examples are illustrative only and not intended to be limiting.

In response to external damage and internal degeneration, the cells of the body must repair the membrane surrounding the each individual cell in order to maintain their function and the health of the organism. Defects in the ability of the cell to repair external membranes have been linked to many diseases, such as neurodegenerative diseases (Parkinson's Disease), heart attacks, heart failure and muscular dystrophy. In addition, the muscle weakness and atrophy associated with various diseases, as well as the normal aging process, has been linked to altered membrane repair. Moreover, membrane damage occurs in many other pathologic states outside of chronic disease. Skin aging due to UV exposure, minor cuts, dermal abrasion, surgical incisions and ulcers in both diabetic and otherwise healthy patients all involve some component of damage to cellular membranes. In order for these cells to repair their membranes in response to acute damage they make use of small packets of membrane that are inside of the cell, referred to as vesicles. These vesicles are normally found within the cell, but upon damage to the cell membrane, these vesicles move to the damage site and form a patch to maintain the cell integrity. Without this essential function, the cell can die and the cumulative effect of this cellular injury can eventually result in dysfunction of the tissue or organ. It is contemplated that the present invention provides compositions and methods for treating and/or preventing the detrimental effects of cell damage.

As described above, in certain aspects the present invention relates to nucleic acids, and the polypeptides encoded from nucleic acids of the invention, which, alone or in combination with other components, can modulate the process of cell membrane resealing in a broad range of cell and tissue types. The invention also relates to compositions, for example, polypeptides, nucleic acids encoding cytoplasmic, nuclear, membrane bound, and secreted polypeptides; as well as vectors, host cells, antibodies, recombinant proteins, pseudopeptides, fusion proteins, chemical compounds, and methods for producing the same.

For example, in certain aspects, the invention encompasses an isolated or recombinant nucleic acid encoding a polypeptide, which comprises a combination of amino acid and/or peptide components (i.e., structural components or amino acid domains), which when combined together, result in a polypeptide having membrane repair activity as described herein. In one embodiment of this aspect of the invention, the components comprise a RING finger zinc-binding domain, a B-box domain, a Leucine zipper coiled-coil domain, a phospholipid binding domain, a redox sensitive amino acid, an E3-ligase domain, and a SPRY domain, wherein the components are covalently joined contiguously in a single polypeptide, and wherein the polypeptide facilitates cell membrane repair. The nucleic acids encoding the respective amino acid or peptide domains can be cloned from any desired parental gene and combined into a single contiguous using standard molecular biological techniques. In additional embodiments, the invention encompasses novel membrane repair polypeptides formed by expressing genes or cDNA constructs formed by combining nucleotides encoding amino acid or peptide components from other members of the TRIM family, for example (be accession number) TRIM1 (NM_012216, NM_052817); TRIM2 (AF220018); TRIM3 (AF045239); TRIM4 (AF220023); TRIM5 (AF220025); TRIM6 (AF220030); TRIM7 (AF220032); TRIM8 (AF281046); TRIM9 (AF220036); TRIM10 (Y07829); TRIM11 (AF220125); TRIM13 (AF220127, NM_001007278); TRIM14 (NM_014788, NM_033221); TRIM15 (NM_033229); TRIM16 (AF096870); TRIM17 (AF156271); TRIM18 (AF230976, AF230977); TRIM19 (NM_033244, NM_033250, NM_033240, NM_033239, NM_033247, NM_002675, NM_033246, NM_033249, NM_033238); TRIM20 (NM_000243); TRIM21 (NM_003141); TRIM22 (NM_006074); TRIM23 (NM_033227, NM_001656, NM_033228); TRIM24 (NM_003852, NM_015905);

TRIM25 (NM_005082), TRIM26 (NM_003449); TRIM27 (AF230394, AF230393); TRIM28 (NM_005762); TRIM29 (AF230388); TRIM31 (AF230386); TRIM32 (NM_012210); TRIM33 (AF220136); TRIM34 (NM_130390, NM_001003827, NM_130389, NM_001003819); TRIM35 (AB029021); TRIM36 (AJ272269); TRIM37 (AB020705); TRIM38 (U90547); TRIM39 (NM_021253, NM_172016); TRIM40 (AF489517); TRIM41 (NM_033549, NM_201627); TRIM42 (AF521868); TRIM43 (NM_138800); TRIM44 (NM_017583); TRIM45 (NM_025188); TRIM46 (NM_025058); TRIM47 (AY026763); TRIM 48 (AF521869); TRIM49 (NM_020358); TRIM50 (AY081948); TRIM51 (NM_032681); TRIM52 (NM_032765); TRIM53 (XR_016180); TRIM54 (NM_032546, NM_187841); TRIM55 (NM_184087, NM_184085, NM_184086, NM_033058); TRIM56 (NM_030961); TRIM57 (i.e., TRIM59); TRIM58 (NM_015431); TRIM59 (NM_173084); TRIM60 (NM_152620); TRIM61 (XM_373038); TRIM62 (NM_018207); TRIM63 (NM_032588); TRIM64 (XM_061890); TRIM65 (NM_173547); TRIM66 (XM_001716253); TRIM67 (NM_001004342); TRIM68 (NM_018073); TRIM69 (AF302088); TRIM70 (DQ232882, NM_001037330); TRIM71 (NM_001039111); TRIM72 (i.e., MG53; NM_001008274); TRIM73 (AF498998); TRIM74 (NM_198853); TRIM75 (XM_939332).

In another embodiment, the invention comprises an isolated or recombinant polypeptide encoded by nucleic acids of the invention, having a RING finger zinc-binding domain, a B-box domain, a Leucine zipper coiled-coil domain, a phospholipid binding domain, a redox sensitive amino acid, an E3-ligase domain, a SPRY domain, and optionally a calcium binding domain, wherein the components are covalently joined contiguously in a single polypeptide, and wherein the polypeptide facilitates cell membrane repair.

The present description highlights the important amino acid structural components or features for creating polypeptides able to facilitate membrane repair (i.e., a RING finger zinc-binding domain, a B-box domain, Leucine zipper coiled-coil domain, a phospholipid binding domain, redox sensitive amino acid, E3-ligase domain, SPRY domain). It is important to note that although RING finger zinc-binding domains, a B-box domains, Leucine zipper coiled-coil domains, a phospholipid binding domains, redox sensitive amino acids, E3-ligase domains, SPRY domains, and calcium binding domains may vary between evolutionarily related proteins as well as unrelated proteins, as indicated above, there exists a number of genes belonging to the TRIM family, which includes MG53, which contain one or all of the above structural components or domains. As those of skill in the art would appreciate, these domains may be readily cloned from the gene or cDNA of a TRIM family member, and grafted or cloned into the framework of another TRIM family gene (i.e., MG53) using well known techniques in molecular biology in order to create novel proteins. Also, because it is generally recognized that evolutionarily conserved amino acid sequences will function similarly, it is within the abilities of those skilled in the art to generate additional proteins in accordance with the instant teachings, and to assess the ability of the recombinant proteins to facilitate membrane repair without undue experimentation. As such, recombinant proteins assembled from the domains of the TRIM family members, for example, those identified above, is expressly contemplated as being within the scope of the invention:

In another embodiment, the invention encompasses an isolated or recombinant nucleic acid encoding an MG53 polypeptide as set forth in SEQ ID NOs.: 1, 3, 5, 7, 8, 9-15, and/or a homolog, or fragment thereof, wherein the polypeptide facilitates cell membrane repair.

In an additional aspect, the invention relates to compositions comprising a polypeptide of the invention in combination with at least one other agent, which is capable of modulating membrane. In certain embodiment, the agent acts synergistically, via direct or indirect interaction with the polypeptide of the invention, to facilitate cell membrane repair. For example, as demonstrated herein, agents such as phosphotidylserine, zinc, oxidizing agents, and plant extracts can modulate the membrane repair activity of the polypeptides of the invention. (See Examples). Therefore, in additional embodiments, any of the membrane repair polypeptide-containing compositions encompassed by the invention may also comprise, in combination, an effective amount of at least one of a phospholipid; a zinc containing agent; an oxidizing agent; a plant extract or a combination thereof. In certain embodiments the phospholipid is phosphytidylserine. In additional embodiments, the zinc containing agent is a zinc ionophore, for example, Zn-1-hydroxypyridine-2-thine (Zn-HPT). In other embodiments, the oxidizing agent is thimerosal. In additional embodiments, the plant extract is *notoginsing* extract.

In certain additional aspects, the invention relates to a composition comprising an isolated or recombinant polypeptide of the invention in combination with a pharmaceutically acceptable carrier. In additional embodiments, the composition may further comprise, in combination, an effective amount of at least one of a phospholipid; a zinc containing agent; an oxidizing agent; a plant extract or a combination thereof. In certain embodiments the phospholipid is phosphytidylserine. In additional embodiments, the zinc containing agent is a zinc ionophore, for example, Zn-1-hydroxypyridine-2-thine (Zn-HPT). In other embodiments, the oxidizing agent is thimerosal. In additional embodiments, the plant extract is *notoginsing* extract.

The present invention also relates to the surprising and unexpected finding that polypeptides of the invention can patch the membrane in many different cell types and tissues. Without being bound by any particular theory, it is believed that the repair mechanism is mediated by the formation of polypeptide oligomers, e.g., dimers, through the coiled-coil domain in the protein, which contains a leucine zipper protein-protein interaction motif.

One of the most surprising discoveries is that the membrane repair activity of the polypeptides of the invention have only a minor dependence on the entry of extracellular calcium following acute membrane damage. This is in contrast with the current paradigm in the field that extracellular calcium entry is the sole signal for cellular membrane repair. The current results indicate that rather than calcium entry, the membrane repair activity of polypeptides of the invention, for example, MG53, is primarily induced by entry of the oxidative extracellular milieu into the reduced environment in the cellular compartment. This mechanism allows for the membrane repair polypeptides to act as a sensor of cellular redox state and oligomerize to form homologous complexes at the plasma membrane by interaction with specific lipid components of the cell membrane. For example, as described in detail herein, zinc (Zn) is required for MG53-mediated membrane resealing, and the presence of additional Zn can improve the activity of MG53; an extract from the plant *notoginseng* can also improve the function of MG53 in membrane resealing; and MG53 requires its endogenous E3-ligase activity to produce membrane repair following acute damage.

Additional aspects of the invention related to the surprising discovery that extracellular application or administration of membrane repair polypeptides, for example, MG53 can also facilitate membrane resealing, suggesting that coupling with cell penetrating peptides, for example, HIV-TAT protein (See WO 2008/054561, which is incorporated herein by reference), may not be necessary for recombinant MG53 to function as an effective therapeutic. As such, certain embodiments of this aspect comprise therapeutic compositions comprising membrane repair polypeptides of the invention, for example, MG53, in combination with a pharmaceutically acceptable carrier, wherein the therapeutic composition is administered systemically, and wherein the systemically administered composition is effective in facilitating membrane repair.

In certain additional embodiments, the therapeutic compositions of the invention further comprise, in combination with a membrane repair polypeptide of the invention, one or more additional ingredients, including a phospholipid; a zinc containing agent; an oxidizing agent; a plant extract or a combination thereof, which have a synergistic effect on the membrane repair of the polypeptides of the invention. In additional embodiments, the therapeutic of the invention may comprise one or more biologically active ingredients such as, Analgesics, Antacids, Antianxiety Drugs, Antiarrhythmics, Antibacterials, Antibiotics, Anticoagulants and Thrombolytics, Anticonvulsants, Antidepressants, Antidiarrheals, Antiemetics, Antifungals, Antihistamines, Antihypertensives, Anti-Inflammatories, Antineoplastics, Antipsychotics, Antipyretics, Antivirals, Barbiturates, Beta-Blockers, Bronchodilators, Cold Cures, Corticosteroids, Cough Suppressants, Cytotoxics, Decongestants, Diuretics, Expectorants, Hormones, Hypoglycemics (Oral), Immunosuppressives, Laxatives, Muscle Relaxants, Sedatives, Sex Hormones, Sleeping Drugs, Tranquilizer, Vitamins or a combination thereof.

In additional aspects, the invention relates to methods of administering to an individual an effective amount of a nucleic acid encoding a membrane repair polypeptide, for example, MG53, homologs, fragments, and derivatives thereof, for the treatment and/or prevention of cell membrane damage of a cell in vitro, in vivo or ex vivo. As demonstrated herein, the membrane repair polypeptides of the invention are capable of facilitating membrane repair in a wide variety of cell and tissue types, and can provide an effective therapeutic approach against a number of disorders that involve compromised membrane permeability. In certain embodiments, the cell comprises, for example, fibroblast cells, epithelial cells of various origins (ovary, kidney, etc.), neuronal cells, keratinocytes, dental cells, gastric cells, immune cells, skeletal muscle, and cardiac muscle cells. The ability to facilitate cell membrane repair in practically any cell and tissue type is easily determined according to the present teachings. Moreover, the skilled artisan would recognize that such embodiments are in the possession of the inventors, and the ability to assay for repair activity is well within the skill of the ordinary artisan in view of the present teachings and would not require undue experimentation.

In an additional aspect, the invention relates to methods of treating and/or preventing a disease or pathological condition related to cell or tissue damage comprising administering to an individual an effective amount of a composition comprising a nucleic acid encoding a membrane repair polypeptide, for example, MG53, homolog, fragment or derivative thereof or a membrane repair polypeptide, in combination with a pharmaceutically acceptable carrier, wherein the composition is effective in treating and/or preventing cell or tissue damage. In certain embodiments, the disease or pathological condition related to cell or tissue damage includes muscular dystrophy, cardiac ischemia, heart failure, aging degeneration, neurodegeneration, sepsis, bacterial infection, gingivitis, gum recession, periodontal disease, wrinkle protection, dermal abrasion, UV damage, nitrogen mustard (chemical blistering agents), ulcers, COPD, wound healing, geriatric medicine, anti-inflammatory or any combination thereof.

In any of the methods described herein, the nucleic acids or polypeptides of the invention may be delivered or administered in any pharmaceutically acceptable form, and in any pharmaceutically acceptable route as described in further detail below. For example, compositions comprising nucleic acids and/or polypeptides of the invention can be delivered systemically or administered directly to a cell or tissue for the treatment and/or prevention of cell membrane damage. In certain additional embodiments, the nucleic acids and/or polypeptides of the invention comprise a carrier moiety that improves bioavailability, increases the drug half-life, targets the therapeutic to a particular cell or tissue type or combination thereof.

In an additional aspect, the invention relates to an isolated or recombinant membrane repair polypeptide complex. As presented in detail below, MG53 polypeptides demonstrate the ability to interact (e.g., bind non-covalently) and form complexes with a number other cellular proteins. In an embodiment of this aspect the invention comprises an isolated or recombinant membrane repair polypeptide, for example, MG53, homologs, fragments, and derivatives thereof, in combination with at least one of CSN6, kinesin, caveolin-3, periaxin, and myelin-basic-protein, wherein the combination forms a protein complex, and wherein the complex is capable of facilitating cell membrane repair. The invention further comprises a method of treating or preventing cell damage comprising administering to a cell an effective amount of an isolated or recombinant membrane repair polypeptide in a protein complex with at least one of CSN6, kinesin, caveolin-3, periaxin, and myelin-basic-protein, wherein the complex is capable of facilitating cell membrane repair. In still an additional embodiment, the invention includes a method of treating or preventing disease or pathological condition related to cell or tissue damage comprising administering to an individual an effective amount of isolated or recombinant membrane repair polypeptide, for example, MG53, in a protein complex with at least one of CSN6, kinesin, caveolin-3, periaxin, and myelin-basic-protein, wherein the complex is capable of ameliorating the effects of the disease or pathological condition.

Method of modulating the activity of MG53 comprising modulating the expression level or activity or both of at least one of CSN6, kinesin, caveolin-3, periaxin, myelin-basic-protein or a combination thereof.

In still additional aspects, the invention relates to methods of screening for compounds that modulate cell membrane repair by contacting at least one of MG53, CSN6, kinesin, caveolin-3, periaxin, myelin-basic-protein or a combination thereof, with a test compound; and measuring the binding of the test compound, and/or the activity of CSN6, kinesin, caveolin-3, periaxin, myelin-basic-protein, and/or the measuring the effects on cell membrane repair.

As described in detail below, and as would be readily appreciated by those skilled in the art, the recombinant membrane repair polypeptides can be produced in prokaryotic cells or eukaryotic cells, for example, mammalian cells and then secreted into the extracellular solution through protein engineering, an approach that should produce large quantities of functional protein.

In certain aspects, the present invention also relates to compositions useful as therapeutics for treating and prevention of diseases and disorders related to cellular and/or tissue damage. Therapeutic compositions of the invention comprise membrane repair polypeptides, for example, MG53 polypeptides, and nucleic acids encoding MG53 polypeptides, for example, the protein of SEQ ID NO. 1 and MG53 polypeptide mutants, homologs, fragments, truncations, pseudopeptides, peptide analogs, and peptidomimetics (herein, "MG53 polypeptides"), as well as compounds that can modulate the activity of MG53 or intermolecular interactions of MG53 with other proteins, for example, CSN6, kinesin, caveolin-3 (SEQ ID NO. 8), periaxin, and myelin-basic-protein. As described herein, MG53 mediates the repair of damage to cellular membranes, and therefore, the targeting and modulating MG53 gene expression, polypeptide synthesis, activity or protein-protein interactions represent a novel therapeutic intervention for tissue repair.

In an additional aspect, the invention relates to the discovery of polypeptide compositions comprising amino acid components or domains that can facilitate the repair of cell membranes. For example, embodiments of this aspect of the invention include isolated or recombinant polypeptides comprising certain amino acid components including a RING finger zinc-binding domain, a B-box zinc-binding domain, a Leucine zipper coiled-coil domain, a phospholipid binding domain, a redox sensitive amino acid, an E3-ligase domain, a SPRY domain, and a calcium binding domain, wherein the components are covalently joined contiguously in a single polypeptide, and wherein the polypeptide facilitates cell membrane repair, in combination with an agent that modulates, synergistically, the membrane repair activity of the polypeptides of the invention. In certain embodiments, the modulating agents include a phospholipid, for example, phosphotidylserine; zinc, for example, in the form of a zinc salt, zinc carrier or zinc conjugate; *notoginsing*; an oxidizing agent or a combination thereof.

In certain additional aspects the invention relates to compositions and methods related to the treatment of tissue damage. In certain exemplary embodiments, the invention encompasses, for example, the administration of an effective amount of a therapeutic composition of the invention for the prevention and/or treatment of cell membrane damage; wound healing; ameliorating surgical trauma, treatment and/or prevention of age-related deficiencies in tissue repair that occur as a natural side-effect of the aging process; treatment and/or prevention of injury to any type of muscle tissue, such as those occurring in subjects suffering from cardiovascular diseases and/or sports-related injuries; the treatment and/or prevention of muscular dystrophy, cardiac ischemia, heart failure, aging degeneration, neurodegeneration, sepsis, bacterial infection, gingivitis, gum recession, periodontal disease, wrinkle protection, dermal abrasion, UV damage, nitrogen mustard (chemical blistering agents), ulcers, COPD, wound healing, geriatric medicine, anti-inflammatory or any combination thereof; as well as the repair and regeneration of body tissues through cosmetic or personal care use.

In addition, the invention relates to nucleic acids, including interfering nucleic acids, and polypeptides encoding MG53 interacting proteins, for example, CSN6, kinesin, caveolin-3 (SEQ ID NO. 8), periaxin, and myelin-basic-protein, mutants, truncations, fragments, homologs, pseudopeptides and peptidomimetics, as well as compounds that can modulate their activity or their intermolecular interactions with MG53. Therefore, in additional aspects, the present invention encompasses methods for the modulation of CSN6, kinesin, caveolin-3 (SEQ ID NO. 8), periaxin, and myelin-basic-protein gene expression, activity, and/or intermolecular interactions for the treatment and/or prevention of a disease or disorder in a subject, for example, for the promotion of tissue repair as described herein. In any of the embodiments described herein, therapeutic compositions can be administered in any suitable pharmaceutical form as described herein or as commonly known in the art.

In an aspect, the invention provides an isolated nucleic acid encoding membrane repair polypeptide molecules, for example, MG53 nucleic acid molecules, and nucleic acids encoding membrane repair polypeptides having at least 30%, 40%, 50%, 60%, 70%, 80%, 90% or 100% identity to the nucleic acids disclosed in SEQ ID NOS: 2, 4, and 6. In certain embodiments, the isolated nucleic acid molecules of the invention will hybridize under stringent conditions to a nucleic acid sequence complementary to a nucleic acid molecule that includes a protein-coding sequence of a membrane repair nucleic acid sequence. The invention also includes an isolated nucleic acid that encodes a membrane repair polypeptide, for example, an MG53 polypeptide, or a fragment, homolog, analog, fusion protein, pseudopeptide, peptidomimetic or derivative thereof. For example, the nucleic acid can encode a polypeptide at least 30%, 40%, 50%, 60%, 70%, 80%, 90% or 100% identity to a polypeptide comprising the amino acid sequences of SEQ ID NOS: 1, 3, 5, 7, 8, and 9-15. The nucleic acid can be, for example, a genomic DNA fragment or a cDNA molecule that includes the nucleic acid sequence of any of SEQ ID NOS: 2, 4, and 6.

Also included in the invention is an oligonucleotide, e.g., an oligonucleotide which includes at least 6 contiguous nucleotides of a membrane repair nucleic acid, for example, a MG53 nucleic acid (e.g., SEQ ID NOS: 2, 4, and 6) or a complement of said oligonucleotide.

Also included in the invention are substantially purified membrane repair polypeptides, for example, MG53 polypeptides (SEQ ID NOS: 1, 3, 5, 7, 8, and 9-15). In certain embodiments, the membrane repair polypeptides, e.g., MG53 polypeptides, include an amino acid sequence that is substantially identical to the amino acid sequence of a human MG53 polypeptide (SEQ ID NO.:1).

The invention also features antibodies that immunoselectively-bind to membrane repair polypeptides, for example, MG53, polypeptides, or fragments, homologs, analogs, pseudopeptides, peptidomimetics or derivatives thereof.

In another aspect, the invention includes pharmaceutical compositions that include therapeutically- or prophylactically-effective amounts of a therapeutic and a pharmaceutically-acceptable carrier. The therapeutic can be a nucleic acid, e.g., a MG53 nucleic acid, for example, a peptide nucleic acid, a cDNA, or RNA, such as for example, a small inhibitory RNA; a membrane repair polypeptide for example, MG53; or an antibody specific for a MG53 polypeptide. In a further aspect, the invention includes, in one or more containers, a therapeutically- or prophylactically-effective amount of this pharmaceutical composition.

In a further aspect, the invention includes a method of producing a polypeptide by culturing a cell that includes an endogenous or exogenously expressed nucleic acid encoding a membrane repair polypeptide, for example a MG53 nucleic acid, under conditions allowing for expression of the polypeptide encoded by the DNA. If desired, the polypeptide can then be recovered.

In still another aspect, the invention includes a method of producing a polypeptide by culturing a cell that contains an endogenous nucleic acid encoding a membrane repair polypeptide, for example a MG53 nucleic acid, disposed upstream or downstream of an exogenous promoter. In certain embodiments, the exogenous promoter is incorporated into a host cell's genome through homologous recombination, strand break or mismatch repair mechanisms.

In another aspect, the invention includes a method of detecting the presence of a membrane repair polypeptide, for example, an MG53 polypeptide, in a sample. In the method, a sample is contacted with a compound that selectively binds to the polypeptide under conditions allowing for formation of a complex between the polypeptide and the compound. The complex is detected, if present, thereby identifying the membrane repair polypeptide, for example, an MG53 polypeptide, within the sample.

The invention also includes methods to identify specific cell or tissue types based on their expression of a nucleic acid encoding a membrane repair polypeptide, for example a MG53 nucleic acid, membrane repair polypeptide or a related fusion polypeptide, thereof. For example, in certain embodiments the invention includes fusion proteins comprising a "tag" or indicator portion and a membrane repair polypeptide, for example, MG53, portion. In certain aspects the tag or indicator portion can be a peptide adapted for purification purposes, for example, FLAG tag, 6×His tag, Maltose-Binding Protein (MBP) tag, or the like. In other aspects, the tag peptide comprises a peptide adapted for providing a signal such as an antibody epitope or a fluorescent peptide. Still other aspects include the fusion of the MG53 with a peptide that is adapted for mediating subcellular localization or translocation across a cellular membrane, for example, a TAT fusion protein from the HIV virus To facilitate cell penetration or a modified cellular localization tag to couple MG53 to particular cellular organelles.

Also included in the invention is a method of detecting the presence of a nucleic acid molecule of the invention in a sample by contacting the sample with a nucleic acid probe or primer, and detecting whether the nucleic acid probe or primer bound to a nucleic acid encoding a membrane repair polypeptide, for example, an MG53 nucleic acid molecule in the sample.

In a further aspect, the invention provides a method for modulating the activity of a membrane repair polypeptide, for example, an MG53 polypeptide, by contacting a cell sample that includes the MG53 polypeptide with a compound that binds to the MG53 polypeptide in an amount sufficient to modulate the activity of said polypeptide. The compound can be, e.g., a small molecule, such as a nucleic acid, peptide, polypeptide, peptidomimetic, carbohydrate, lipid or other organic (carbon containing) or inorganic molecule, as further described herein.

Also within the scope of the invention is the use of a therapeutic of the invention in the manufacture of a medicament for treating or preventing disorders or syndromes including, e.g., cardiovascular disease, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, hypercoagulation, hemophilia, ulcers, wounds, lesions, cuts, abrasions, oxidative damage, age-related tissue degeneration, surgically related lesions, burns, muscle weakness, muscle atrophy, connective tissue disorders, idiopathic thrombocytopenic purpura, heart failure, secondary pathologies caused by heart failure and hypertension, hypotension, angina pectoris, myocardial infarction, tuberous sclerosis, scleroderma, transplantation, autoimmune disease, lupus erythematosus, viral/bacterial/parasitic infections, multiple sclerosis, autoimmune disease, allergies, immunodeficiencies, graft versus host disease, asthma, emphysema, ARDS, inflammation and modulation of the immune response, viral pathogenesis, aging-related disorders, Th1 inflammatory diseases such as rheumatoid arthritis, multiple sclerosis, inflammatory bowel diseases, AIDS, wound repair, heart attacks, heart failure, muscular dystrophy, bed sores, diabetic ulcers, oxidative damage, and tissue damage such as sinusitis or mucositis, wrinkles, eczema or dermatitis, dry skin, obesity, diabetes, endocrine disorders, anorexia, bulimia, renal artery stenosis, interstitial nephritis, glomerulonephritis, polycystic kidney disease, systemic, renal tubular acidosis, IgA nephropathy, nephrological diseases, hypercalcemia, Lesch-Nyhan syndrome, Von Hippel-Lindau (VHL) syndrome, trauma, regeneration (in vitro and in vivo), Hirschsprung's disease, Crohn's Disease, appendicitis, endometriosis, laryngitis, psoriasis, actinic keratosis, acne, hair growth/loss, allopecia, pigmentation disorders, myasthenia gravis, alpha-mannosidosis, beta-mannosidosis, other storage disorders, peroxisomal disorders such as zellweger syndrome, infantile refsum disease, rhizomelic chondrodysplasia (chondrodysplasia punctata, rhizomelic), and hyperpipecolic acidemia, osteoporosis, muscle disorders, urinary retention, Albright Hereditary Ostoeodystrophy, ulcers, Alzheimer's disease, stroke, Parkinson's disease, Huntington's disease, cerebral palsy, epilepsy, Lesch-Nyhan syndrome, multiple sclerosis, ataxia-telangiectasia, behavioral disorders, addiction, anxiety, pain, neuroprotection, Stroke, Aphakia, neurodegenerative disorders, neurologic disorders, developmental defects, conditions associated with the role of GRK2 in brain and in the regulation of chemokine receptors, encephalomyelitis, anxiety, schizophrenia, manic depression, delirium, dementia, severe mental retardation and dyskinesias, Gilles de la Tourette syndrome, leukodystrophies, cancers, breast cancer, CNS cancer, colon cancer, gastric cancer, lung cancer, melanoma, ovarian cancer, pancreatic cancer, kidney cancer, colon cancer, prostate cancer, neuroblastoma, and cervical cancer, Neoplasm; adenocarcinoma, lymphoma; uterus cancer, benign prostatic hypertrophy, fertility, control of growth and development/differentiation related functions such as but not limited maturation, lactation and puberty, reproductive malfunction, and/or other pathologies and disorders of the like.

The therapeutic composition of the invention comprises, in certain embodiments, for example, a nucleic acid encoding a membrane repair polypeptide, an MG53 nucleic acid; a nucleic acid that binds a nucleic acid encoding a membrane repair polypeptide; an MG53 encoding nucleic acid; an MG53 polypeptide, peptide analog, pseudopeptide or peptidomimetic based thereon; a small molecule modulator of a membrane repair polypeptide, MG53 or a membrane repair polypeptide or MG53 protein-protein interaction; or a MG53-specific antibody or biologically-active derivatives or fragments thereof. As described herein, MG53 mediates the repair of damage to cellular membranes. Therefore, targeting the expression and/or activity of these nucleic acids, polypeptides, and homologs thereof will allow for a novel treatment of various acute and chronic diseases and conditions related to tissue repair.

In certain other aspects, the invention includes methods for the treatment of or amelioration of tissue damage and/or disorders related to tissue damage comprising administering an effective amount of the composition of the invention to a subject in need thereof. In certain embodiments, the invention comprises methods for treating tissue damage or wounds, for example, cuts, abrasions, lesions, ulcers, burns, bed sores, gum diseases, mucositis, and the like, comprising administering an effective amount of the therapeutic composition of the invention to a subject in need thereof.

In still other embodiments, the invention comprises therapeutic compositions useful as a surgical adjuvant. In any of the embodiments described herein, the surgical adjuvant composition of the invention can be used or applied as a stand alone therapeutic directly to the surgical site or it can be integrally associated with a surgical or medical implement, for example, the therapeutic of the invention may be conjugated to a polymer-based stent, tube or other implantable device, such that the therapeutic diffuses to the site of action in a controlled manner to accelerate healing and/or to minimize trauma from an invasive surgical procedure. In another embodiment, the therapeutic composition of the invention is applied as, for example, a film or coating to the medical implement such that the therapeutic diffuses into the blood stream or surrounding tissues and/or wears away, and is thereby delivered directly to the site of tissue damage; minimizing or ameliorating the amount of cellular damage that occurs due to the use of the surgical implement.

In still other embodiments, the invention comprises methods for the treatment and/or prevention of deficiencies in tissue repair that occur as a natural side-effect of the aging process (e.g., skin rejuvenation, receding gums, bone degeneration, arthritis, Alzheimers, Parkinsons, and the like). In certain aspects of this embodiment, the invention comprises administering an effective amount of a therapeutic composition of the invention to a subject suffering from age-related deficiencies in tissue repair capacity, tissue integrity, and/or tissue elasticity. In certain embodiments, the age-related deficiency is at least one of wrinkles, crows feet, facial lines, pot marks, scars, fibroids, sun spots, and the like, or combinations thereof.

Furthermore, due to the muscle-specific nature of the expression of the endogenous MG53 gene, the invention encompasses methods for the treatment and/or prevention of any type of muscle or vascular cell/tissue injury, for example, tissue injury that occurs as a result of cardiovascular disease, for example, myocardial infarction; or rigorous physical activity, for example, sports-related injuries, comprising administering an effective amount of the therapeutic of the invention to a subject in need thereof.

In still other embodiments, the invention comprises a cosmetic composition useful for the repair, regeneration, or restoration of body tissues comprising the therapeutic of the invention and a cosmetically suitable carrier or excipient. In one aspect of this embodiment, the invention encompasses a method of enhancing the appearance of skin comprising administering an effective amount of the therapeutic composition of the invention in a cosmetic to a subject.

In any aspect of the invention, the therapeutic composition of the invention can be in any pharmaceutically acceptable form and administered by any pharmaceutically acceptable route, for example, the therapeutic composition can be administered as an oral dosage, either single daily dose or unitary dosage form, for the treatment of a muscle damage due to a myocardial infarction, sclerotic lesion, or muscle tear due to sports-related activity to promote the regeneration and repair of the damaged muscle tissue. Such pharmaceutically acceptable carriers and excipients and methods of administration will be readily apparent to those of skill in the art, and include compositions and methods as described in the USP-NF 2008 (United States Pharmacopeia/National Formulary), which is incorporated herein by reference in its entirety.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The active compounds will generally be formulated for parenteral administration, e.g., formulated for injection via the intravenous, intraarthricular, intrathecal, intramuscular, sub-cutaneous, intra-lesional, or even intraperitoneal routes. The preparation of an aqueous composition that contains a cancer marker antibody, conjugate, inhibitor or other agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

In addition, the invention relates to nucleic acids, including interfering nucleic acids, and polypeptides encoding membrane repair interacting proteins and/or MG53 interacting proteins, and homologs thereof; pseudopeptides and peptidomimetics; as well as compounds that can modulate the activity of membrane repair polypeptides or MG53 or their intermolecular interactions.

For example, the compositions of the present invention will have efficacy for treatment of patients suffering from the diseases and disorders disclosed above and/or other pathologies and disorders of the like. The polypeptides can be used as immunogens to produce antibodies specific for the invention, and as vaccines. They can also be used to screen for potential agonist and antagonist compounds. In addition, a cDNA encoding membrane repair polypeptides of the invention, for example, MG53, may be useful in gene therapy when administered to a subject in need thereof. By way of non-limiting example, the compositions of the present invention will have efficacy for treatment of patients suffering from the diseases and disorders disclosed above and/or other pathologies and disorders of the like.

The invention further includes a method for screening for a modulator of disorders or syndromes including, e.g., the diseases and disorders disclosed above and/or other pathologies and disorders of the like. The method includes contacting a test compound with a membrane repair polypeptide, for example, an MG53 polypeptide, and determining if the test compound binds to said membrane repair polypeptide or MG53 polypeptide. Binding of the test compound to the membrane repair polypeptide or MG53 polypeptide indicates the test compound is a modulator of activity, or of latency or predisposition to the aforementioned disorders or syndromes.

Also within the scope of the invention is a method for screening for a modulator of activity, or of latency or predisposition to disorders or syndromes including, e.g., the diseases and disorders disclosed above and/or other pathologies and disorders of the like by administering a test compound to a test animal at increased risk for the aforementioned disorders or syndromes. The test animal expresses a recombinant polypeptide encoded by a nucleic acid of the invention. Expression or activity of a polypeptide of the invention is then measured in the test animal, as is expression or activity of the protein in a control animal which recombinantly-expresses the polypeptide of the invention and is not at increased risk for the disorder or syndrome. Next, the expression of polypeptides of the invention in both the test animal and the control animal is compared. A change in the activity of the polypeptide in the test animal relative to the control animal indicates the test compound is a modulator of latency of the disorder or syndrome.

In yet another aspect, the invention includes a method for determining the presence of or predisposition to a disease associated with altered levels of a membrane repair polypeptide or nucleic acid encoding the same, for example, an MG53 polypeptide, a MG53 nucleic acid, or both, in a subject (e.g., a human subject). The method includes measuring the amount of the membrane repair polypeptide in a test sample from the subject and comparing the amount of the polypeptide in the test sample to the amount of the membrane repair polypeptide present in a control sample. An alteration in the level of the membrane repair polypeptide in the test sample as compared to the control sample indicates the presence of or predisposition to a disease in the subject. Preferably, the predisposition includes, e.g., the diseases and disorders disclosed above and/or other pathologies and disorders of the like. Also, the expression levels of the new polypeptides of the invention can be used in a method to screen for various disorders as well as to determine the stage of particular disorders.

In a further aspect, the invention includes a method of treating or preventing a pathological condition associated with a disorder in a mammal by administering to the subject a membrane repair polypeptide, a nucleic acid encoding a membrane repair polypeptide, or a membrane repair polypeptide-specific antibody to a subject (e.g., a human subject), in an amount sufficient to alleviate or prevent the pathological condition. In preferred embodiments, the disorder, includes, e.g., the diseases and disorders disclosed above and/or other pathologies and disorders of the like.

In yet another aspect, the invention can be used in a method to identity the cellular receptors and downstream effectors of the invention by any one of a number of techniques commonly employed in the art. These include but are not limited to the two-hybrid system, affinity purification, co-precipitation with antibodies or other specific-interacting molecules.

As used herein, the term "membrane repair polypeptide antagonist" or "MG53 antagonist" or "antagonist of a membrane repair polypeptide" or "antagonist of MG53" is used generally to refer to an agent capable of direct or indirect inhibition of a membrane repair polypeptide, for example, MG53, expression, translation, and/or activity. Also, as used herein "membrane repair polypeptide receptor" or "MG53 receptor" relates generally to any protein or fragment thereof capable of undergoing binding to a MG53 protein.

In certain aspects, the modulation of membrane repair polypeptide, for example, MG53, activity is accomplished by, for example, the use of or modulation of membrane repair polypeptide, for example, MG53, binding partners, i.e., factors that bind to membrane repair polypeptide, for example, MG53, and neutralize its biological activities, such as neutralizing anti-MG53, membrane repair polypeptide, for example, MG53, receptors (for example, or caveolin-3), membrane repair polypeptide, for example, MG53, receptor fragments, and membrane repair polypeptide, for example, MG53, receptor analogs; the use of membrane repair polypeptide, for example, MG53, receptor antagonists, such as anti-caveolin-3 antibodies, pseudopeptides, peptide analogs or peptidomimetics that bind and disrupt the membrane repair polypeptide-receptor interaction; small molecules that inhibit membrane repair polypeptide activity or intermolecular interactions, or alter the normal configuration of a membrane repair polypeptide, or inhibit productive membrane repair polypeptide/membrane repair polypeptide-receptor binding; or the use of nucleotide sequences derived from membrane repair polypeptide gene and/or membrane repair polypeptide receptor gene, including coding, non-coding, and/or regulatory sequences to prevent or reduce membrane repair polypeptide expression by, for example, antisense, ribozyme, and/or triple helix approaches.

In another aspect, the present invention features a nucleic acid molecule, such as a decoy RNA, dsRNA, siRNA, shRNA, micro RNA, aptamers, antisense nucleic acid molecules, which down regulates expression of a sequence encoding a membrane repair polypeptides, MG53 proteins, membrane repair polypeptide binding proteins, MG53 binding proteins, membrane repair polypeptide receptors and/or MG53 receptor, for example, caveolin-3. In an embodiment, a nucleic acid molecule of the invention is adapted to treat and/or prevent tissue damage and promote tissue repair. In another embodiment, a nucleic acid molecule of the invention has an endonuclease activity or is a component of a nuclease complex, and cleaves RNA having a membrane repair polypeptide nucleic acid sequence or a membrane repair polypeptide receptor nucleic acid sequence.

In one embodiment, a nucleic acid molecule of the invention comprises between 12 and 100 bases complementary to RNA having a membrane repair or a membrane repair-receptor nucleic acid sequence. In another embodiment, a nucleic acid molecule of the invention comprises between 14 and 24 bases complementary to RNA having a membrane repair or a membrane repair-receptor nucleic acid sequence. In any embodiment described herein, the nucleic acid molecule can be synthesized chemically according to methods well known in the art.

In another aspect the present invention provides a kit comprising a suitable container, the active agent capable of inhibiting membrane repair polypeptide activity, expression or binding in a pharmaceutically acceptable form disposed therein, and instructions for its use.

In another aspect, the invention relates to a method for diagnosing or monitoring disorder or disease or progression comprising detecting for the presence of a nucleotide polymorphism in the membrane repair gene, for example, MG53 gene, associated with the disease, through the detection of the expression level of a membrane repair or a membrane repair receptor gene or protein or both.

Polymorphisms have been identified that correlate with disease severity. (See, Zhong et al., Simultaneous detection of microsatellite repeats and SNPs in the macrophage migration inhibitory factor gene by thin-film biosensor chips and application to rural field studies. *Nucleic Acids Res.* 2005 Aug. 2; 33(13):e121; Donn et al., A functional promoter haplotype of macrophage migration inhibitory factor is linked and associated with juvenile idiopathic arthritis. *Arthritis Rheum.* 2004 May; 50(5):1604-10; all of which are incorporated herein by reference in their entirety for all purposes.). As used herein, "membrane repair polypeptide" or "membrane repair polypeptide receptor gene" or "MG53 or MG53 receptor gene" or "MG53 or MG53 receptor gene" includes the 5' UTR, 3' UTR, promoter sequences, enhancer sequences, intronic and exonic DNA of the gene as well as the mRNA or cDNA sequence.

As one of ordinary skill will comprehend, the MG53 or MG53 receptor gene polymorphisms associated with tissue repair disorders, and hence useful as diagnostic markers according to the methods of the invention may appear in any of the previously named nucleic acid regions. Techniques for the identification and monitoring of polymorphisms are known in the art and are discussed in detail in U.S. Pat. No. 6,905,827 to Wohlgemuth, which is incorporated herein by reference in its entirety for all purposes.

Certain aspects of the invention encompass methods of detecting gene expression or polymorphisms with one or more DNA molecules wherein the one or more DNA molecules has a nucleotide sequence which detects expression of a gene corresponding to the oligonucleotides depicted in the Sequence Listing. In one format, the oligonucleotide detects expression of a gene that is differentially expressed. The gene expression system may be a candidate library, a diagnostic agent, a diagnostic oligonucleotide set or a diagnostic probe set. The DNA molecules may be genomic DNA, RNA, protein nucleic acid (PNA), cDNA or synthetic oligonucleotides. Following the procedures taught herein, one can identify sequences of interest for analyzing gene expression or polymorphisms. Such sequences may be predictive of a disease state.

Diagnostic Oligonucleotides of the Invention

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

In certain aspects, the invention relates to diagnostic oligonucleotides and diagnostic oligonucleotide set(s), for which a correlation exists between the health status of an individual, and the individual's expression of RNA or protein products corresponding to the nucleotide sequence. In some instances, only one oligonucleotide is necessary for such detection. Members of a diagnostic oligonucleotide set may be identified by any means capable of detecting expression or a polymorphism of RNA or protein products, including but not limited to differential expression screening, PCR, RT-PCR, SAGE analysis, high-throughput sequencing, microarrays, liquid or other arrays, protein-based methods (e.g., western blotting, proteomics, mass-spectrometry, and other methods described herein), and data mining methods, as further described herein.

In the context of the invention, nucleic acids and/or proteins are manipulated according to well known molecular biology techniques. Detailed protocols for numerous such procedures are described in, e.g., in Ausubel et al. Current Protocols in Molecular Biology (supplemented through 2000) John Wiley & Sons, New York ("Ausubel"); Sambrook et al. Molecular Cloning—A Laboratory Manual (2nd Ed.), Vol. 1-3, Cold Spring Harbor Laboratory, Cold Spring Harbor, N.Y., 1989 ("Sambrook"), and Berger and Kimmel Guide to Molecular Cloning Techniques, Methods in Enzymology volume 152 Academic Press, Inc., San Diego, Calif. ("Berger").

The description below of the various aspects and embodiments is provided with reference to the exemplary nucleic acids of the invention. However, the various aspects and embodiments are also directed to genes which encode homologs, orthologs, and paralogs of other membrane repair proteins, membrane repair polypeptide binding proteins, and membrane repair polypeptide receptor genes and include all isoforms, splice variants, and polymorphisms. Those additional genes can be analyzed for target sites using the methods described for membrane repair polypeptides, MG53 proteins, membrane repair polypeptide binding proteins, MG53 binding proteins, membrane repair polypeptide receptors and/or MG53 receptor genes. Thus, the inhibition and the effects of such inhibition of the other genes can be performed as described herein.

By "down-regulate" it is meant that the expression of the gene, or level of RNAs or equivalent RNAs encoding one or more proteins, or activity of one or more proteins, such as membrane repair polypeptide and membrane repair polypeptide receptor genes, is reduced below that observed in the absence of the nucleic acid molecules of the invention. In one embodiment, inhibition or down-regulation with enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of membrane repair polypeptides, membrane repair polypeptide binding proteins, and membrane repair polypeptide receptor genes with the nucleic acid molecule of the instant invention is greater in the presence of the nucleic acid molecule than in its absence.

By "up-regulate" is meant that the expression of the gene, or level of RNAs or equivalent RNAs encoding one or more protein subunits, or activity of one or more protein subunits, such as membrane repair polypeptides, membrane repair polypeptide binding proteins, and membrane repair polypeptide receptor genes, is greater than that observed in the absence of the nucleic acid molecules of the invention. For example, the expression of a gene, such as membrane repair polypeptides, membrane repair polypeptide binding proteins, and membrane repair polypeptide receptor genes, can be increased in order to treat, prevent, ameliorate, or modulate a pathological condition caused or exacerbated by an absence or low level of gene expression. In one embodiment the invention relates to a method for treating or preventing bladder over activity by up-regulating the expression, release, and/or activity of a membrane repair polypeptides, membrane repair polypeptide binding proteins, and membrane repair polypeptide receptor genes.

By "modulate" is meant that the expression of the gene, or level of RNAs or equivalent RNAs encoding one or more proteins, or activity of one or more proteins is up-regulated or down-regulated, such that the expression, level, or activity is greater than or less than that observed in the absence of the nucleic acid molecules of the invention.

By "gene" it is meant a nucleic acid that encodes RNA, for example, nucleic acid sequences including but not limited to a segment encoding a polypeptide.

"Complementarity" refers to the ability of a nucleic acid to form hydrogen bond(s) with another RNA sequence by either traditional Watson-Crick or other non-traditional types.

By "RNA" is meant a molecule comprising at least one ribonucleotide residue. By "ribonucleotide" or "2'-OH" is meant a nucleotide with a hydroxyl group at the 2' position of a D-ribo-furanose moiety.

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra).

By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

By "homology" is meant the nucleotide sequence of two or more nucleic acid molecules is partially or completely identical. In certain embodiments the homolgous nucleic acid has 30%, 40%, 50%, 60%, 70%, 80%, 90%, or 95% homology to membrane repair polypeptides, for example, at least one of SEQ ID NOs.: 1, 3, 5, 9, 10, 11, 12, 13, 14, 15, or 16, membrane repair polypeptide binding proteins, and membrane repair polypeptide receptor genes.

By "antisense nucleic acid", it is meant a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop or hairpin and/or an antisense molecule can bind such that the antisense molecule forms a loop or hairpin. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol, 40, 1-49, which are incorporated herein by reference in their entirety. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

Long double-stranded RNAs (dsRNAs; typically >200 nt) can be used to silence the expression of target genes in a variety of organisms and cell types (e.g., worms, fruit flies, and plants). Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. In mammalian cells, introduction of long dsRNA (>30 nt) initiates a potent antiviral response, exemplified by nonspecific inhibition of protein synthesis and RNA degradation. The mammalian antiviral response can be bypassed, however, by the introduction or expression of siRNAs.

Injection and transfection of dsRNA into cells and organisms has been the main method of delivery of siRNA. And while the silencing effect lasts for several days and does appear to be transferred to daughter cells, it does eventually diminish. Recently, however, a number of groups have developed expression vectors to continually express siRNAs in transiently and stably transfected mammalian cells. (See, e.g., Brummelkamp T R, Bernards R, and Agami R. (2002). A system for stable expression of short interfering RNAs in mammalian cells. *Science* 296:550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L.

(2002). RNA interference by expression of short-interfering RNAs and hairpin RNAs in mammalian cells. *Proc. Natl. Acad. Sci. USA* 99(9):6047-6052, which are herein incorporated by reference in their entirety).

By "vectors" is meant any nucleic acid-based technique used to deliver a desired nucleic acid, for example, bacterial plasmid, viral nucleic acid, HAC, BAC, and the like.

The nucleic acid molecules of the instant invention, individually, or in combination or in conjunction with other drugs, can be used to treat diseases or conditions discussed above. For example, the subject can be treated, or other appropriate cells can be treated, as is evident to those skilled in the art, individually or in combination with one or more drugs under conditions suitable for the treatment.

By "double stranded RNA" or "dsRNA" is meant a double stranded RNA that matches a predetermined gene sequence that is capable of activating cellular enzymes that degrade the corresponding messenger RNA transcripts of the gene. These dsRNAs are referred to as short intervening RNA (siRNA) and can be used to inhibit gene expression (see for example Elbashir et al., 2001, Nature, 411, 494-498; and Bass, 2001, Nature, 411, 428-429). The term "double stranded RNA" or "dsRNA" as used herein refers to a double stranded RNA molecule capable of RNA interference "RNAi", including short interfering RNA "siRNA" see for example Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.

As used in herein "cell" is used in its usual biological sense, and does not refer to an entire multicellular organism. The cell can, for example, be in vivo, in vitro or ex vivo, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

By "membrane repair polypeptides", "membrane repair polypeptide binding proteins", and "membrane repair polypeptide receptor genes" or "MG53," "MG53 binding protein," and "MG53 receptor" proteins is meant, a peptide or protein comprising a full length membrane repair polypeptide and/or MG53, membrane repair polypeptide binding protein, and/or MG53 binding protein, or a membrane repair polypeptide receptor protein and/or MG53 receptor protein, domain, fusion protein, chimera, or fragment thereof.

Oligonucleotides (eg; antisense, GeneBlocs) are synthesized using protocols known in the art as described in Caruthers et al., 1992, Methods in Enzymology 211, 3 19, Thompson et al., International PCT Publication No. WO 99/54459, Wincott et al., 1995, Nucleic Acids Res. 23, 2677 2684, Wincott et al., 1997, Methods Mol. Bio., 74, 59, Brennan et al, 1998, Biotechnol Bioeng., 61, 33 45, and Brennan, U.S. Pat. No. 6,001,311. All of these references are incorporated herein by reference. In a non-limiting example, small scale syntheses are conducted on a 394 Applied Biosystems, Inc. synthesizer. Alternatively, the nucleic acid molecules of the present invention can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

The nucleic acid molecules of the present invention can be modified extensively to enhance stability by modification with nuclease resistant groups, for example, 2'-amino, 2'-C-allyl, 2'-flouro, 2'-O-methyl, 2'-H (for a review see Usman and Cedergren, 1992, TIBS 17, 34; Usman et al., 1994, Nucleic Acids Symp. Ser. 31, 163).

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized The reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Nucleic acid molecules are preferably resistant to nucleases in order to function as effective intracellular therapeutic agents Improvements in the chemical synthesis of RNA and DNA (Wincott et al., 1995 Nucleic Acids Res. 23, 2677; Caruthers et al., 1992, Methods in Enzymology 211, 3-19 (incorporated by reference herein) have expanded the ability to modify nucleic acid molecules by introducing nucleotide modifications to enhance their nuclease stability as described above. The use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules and/or other chemical or biological molecules). The treatment of subjects with nucleic acid molecules can also include combinations of different types of nucleic acid molecules.

In one embodiment, the invention features modified nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, Nucleic Acid Analogues: Synthesis and Properties, in Modern Synthetic Methods, VCH, 331 417, and Mesmaeker et al., 1994, Novel Backbone Replacements for Oligonucleotides, in Carbohydrate Modifications in Antisense Research, ACS, 24 39. These references are hereby incorporated by reference herein. Various modifications to nucleic acid (e.g., antisense and ribozyme) structure can be made to enhance the utility of these molecules. For example, such modifications can enhance shelf-life, half-life in vitro, bioavailability, stability, and ease of introduction of such oligonucleotides to the target site, including e.g., enhancing penetration of cellular membranes and conferring the ability to recognize and bind to targeted cells.

Administration of Nucleic Acid Molecules. Methods for the delivery of nucleic acid molecules are described in Akhtar et al., 1992, Trends Cell Bio., 2, 139; and Delivery Strategies for Antisense Oligonucleotide Therapeutics, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by a incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. For a comprehensive review on drug delivery strategies including CNS delivery, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400.

The molecules of the instant invention can be used as pharmaceutical agents. Pharmaceutical agents prevent, inhibit the occurrence, or treat (alleviate a symptom to some extent, preferably all of the symptoms) a disease state in a subject.

The negatively charged polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, preferably a human. By "systemic administration" is meant in vivo systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich, D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Prog Neuropsychopharmacol Biol Psychiatry, 23, 941-949, 1999). Other non-limiting examples of delivery strategies, including CNS delivery of nucleic acid molecules include material described in Boado et al., 1998, J. Pharm. Sci., 87, 1308-1315; Tyler et al, 1999, FEBS Lett., 421, 280-284; Pardridge et al., 1995, PNAS USA., 92, 5592-5596; Boado, 1995, Adv. Drug Delivery Rev., 15, 73-107; Aldrian-Herrada et al., 1998, Nucleic Acids Res., 26, 4910-4916; and Tyler et al., 1999, PNAS USA., 96, 7053-7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

An effective amount, pharmaceutically effective dose, therapeutically effective amount, or pharmaceutically effective amount is that dose required to prevent, inhibit the occurrence, or treat (alleviate a symptom to some extent, preferably all of the symptoms) of a disease state or pathological condition. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the negatively charged polymer. In addition, effective amounts of the compositions of the invention encompass those amounts utilized in the examples to facilitate the intended or desired biological effect.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Nucleic acid molecules of the invention can also be administered in the form of suppositories, e.g., for rectal administration of the drug or via a catheter directly to the bladder itself. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle. The amount of active ingredient that can be combined with the carrier materials to produce a single dosage form varies depending upon the host treated and the particular mode of administration. Dosage unit forms generally contain between from about 1 mg to about 5000 mg of an active ingredient. It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water. The composition can also be administered to a subject in combination with other therapeutic compounds to increase the overall therapeutic effect. The use of multiple compounds to treat an indication can increase the beneficial effects while reducing the presence of side effects.

Alternatively, certain of the nucleic acid molecules of the instant invention can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591 5; Kashani-Sabet et al., 1992, Antisense Res. Dev., 2, 3 15; Dropulic et al., 1992, J. Virol., 66, 1432 41; Weerasinghe et al., 1991, J. Virol., 65, 5531 4; Ojwang et al., 1992, Proc. Natl. Acad. Sci. USA, 89, 10802 6; Chen et al., 1992, Nucleic Acids Res., 20, 4581 9; Sarver et al., 1990 Science, 247, 1222 1225; Thompson et al, 1995, Nucleic Acids Res., 23, 2259; Good et al., 1997, Gene Therapy, 4, 45; all of these references are hereby incorporated in their totalities by reference herein). Those skilled in the art realize that any nucleic acid can be expressed in eukaryotic cells from the appropriate DNA/RNA vector.

In one aspect the invention features an expression vector comprising a nucleic acid sequence encoding at least one of the nucleic acid molecules of the instant invention. The nucleic acid sequence encoding the nucleic acid molecule of the instant invention is operably linked in a manner which allows expression of that nucleic acid molecule.

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743 7; Gao and Huang 1993, Nucleic Acids Res., 21, 2867 72; Lieber et al., 1993, Methods Enzymol., 217, 47 66; Zhou et al., 1990, Mol. Cell. Biol., 10, 4529 37). All of these references are incorporated by reference herein. Several investigators have demonstrated that nucleic acid molecules, such as ribozymes expressed from such promoters can function in mammalian cells (e.g. Kashani-Sabet et al., 1992, Antisense Res. Dev., 2, 3 15; Ojwang et al., 1992, Proc. Natl. Acad. Sci. USA, 89, 10802 6; Chen et al, 1992, Nucleic Acids Res., 20, 4581 9; Yu et al., 1993, Proc. Natl. Acad. Sci. USA, 90, 6340 4; L'Huillier et al., 1992, EMBO J., 11, 4411 8; Lisziewicz et al., 1993, Proc. Natl. Acad. Sci. U.S.A, 90, 8000 4; Thompson et al., 1995, Nucleic Acids Res., 23, 2259; Sullenger & Cech, 1993, Science, 262, 1566).

In another aspect the invention features an expression vector comprising nucleic acid sequence encoding at least one of the nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule.

A further object of the present invention is to provide a kit comprising a suitable container, the therapeutic of the invention in a pharmaceutically acceptable form disposed therein, and instructions for its use.

In another embodiment, an isolated nucleic acid molecule of the invention comprises a nucleic acid molecule that is a complement of the nucleotide sequence of a membrane repair polypeptide, MG53, membrane repair polypeptide binding protein, MG53 binding protein, membrane repair polypeptide receptor, and/or MG53 receptor. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect.

As used herein, "fragments" are defined as sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence.

The term "host cell" includes a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

"Derivatives" are compositions formed from the native compounds either directly, by modification, or by partial substitution.

"Analogs" are nucleic acid sequences or amino acid sequences that have a structure similar to, but not identical to, the native compound.

Derivatives or analogs of the nucleic acids or proteins of the invention include, but are not limited to, molecules comprising regions that are substantially homologous to the nucleic acids or proteins of the invention, in various embodiments, by at least about 30%, 40%, 50%, 60%, 70%, 80%, 90%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30%, 40%, 50%, 60%, 70%, 80%, or 90% at the primary amino acid structure level, it is concluded that they share a common ancestor. For purposes of the present invention, genes are homologous if the nucleic acid sequences are sufficiently similar to allow recombination and/or hybridization under low stringency conditions.

As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA.

Furthermore, one of ordinary skill will recognize that "conservative mutations" also include the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202 (1987); PCR PROTOCOLS A GUIDE TO METHODS AND APPLICATIONS (Innis et al. eds), Academic Press, Inc., San Diego, Calif. (1990) (Innis); Amheim & Levinson (Oct. 1, 1990) C&EN 36-47.

In yet another embodiment, a nucleic acid of the invention is expressed in mammalian cells using a mammalian expression vector. For suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

A polynucleotide can be a DNA molecule, a cDNA molecule, genomic DNA molecule, or an RNA molecule. A polynucleotide as DNA or RNA can include a sequence wherein T (thymidine) can also be U (uracil). If a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process.

Transformation of a host cell with recombinant DNA may be carried out by conventional techniques as are well known to those skilled in the art. By "transformation" is meant a permanent or transient genetic change induced in a cell following incorporation of new DNA (i.e., DNA exogenous to the cell).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

In any of the embodiments, the nucleic acids encoding a membrane repair polypeptide, MG53, membrane repair polypeptide binding protein, MG53 binding protein, membrane repair polypeptide receptor, and/or MG53 receptor can be present as: one or more naked DNAs; one or more nucleic acids disposed in an appropriate expression vector and maintained episomally; one or more nucleic acids incorporated into the host cell's genome; a modified version of an endogenous gene encoding the components of the complex; one or more nucleic acids in combination with one or more regulatory nucleic acid sequences; or combinations thereof. The nucleic acid may optionally comprise a linker peptide or fusion protein component, for example, His-Tag, FLAG-Tag, Maltose Binding Protein (MBP)-Tag, fluorescent protein, GST, TAT, an antibody portion, a signal peptide, and the like, at the 5' end, the 3' end, or at any location within the ORF.

In a preferred embodiment, the nucleic acid of the invention comprises a polynucleotide encoding the soluble (i.e., the extracellular) portion of a membrane repair polypeptide receptor or MG53 receptor. Any of the embodiments described herein, can be achieved using standard molecular biological and genetic approaches well known to those of ordinary skill in the art.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$, RbCl, liposome, or liposome-protein conjugate can be used. Transformation can also be performed after forming a protoplast of the host cell or by electroporation. These examples are not limiting on the present invention; numerous techniques exist for transfecting host cells that are well known by those of skill in the art and which are contemplated as being within the scope of the present invention.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. The eukaryotic cell may be a yeast cell (e.g., *Saccharomyces cerevisiae*) or may be a mammalian cell, including a human cell. For long-term, high-yield production of recombinant proteins, stable expression is preferred.

Polypeptides

In other embodiments, the invention pertains to isolated nucleic acid molecules that encode membrane repair polypeptides, MG53, membrane repair polypeptide binding proteins, MG53 binding proteins, membrane repair polypeptide receptors, and/or MG53 receptor polypeptides, antibody polypeptides, or biologically active portions thereof. The polypeptides of the complex can be formed, for example, using a peptide synthesizer according to standard methods; or by expressing each polypeptide separately in a cell or cell extract, then isolating and purifying the polypeptide.

Antibodies

The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')2 fragments, and an Fab expression library. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids of membrane repair polypeptides, MG53, membrane repair polypeptide binding proteins, MG53 binding proteins, membrane repair polypeptide receptors, and/or MG53 receptor protein. In one embodiment, the peptide is located in a non-transmembrane domain of the polypeptide, e.g., in an extracellular or intracellular domain. An exemplary antibody or antibody fragment binds to an epitope that is accessible from the extracellular milieu and that alters the functionality of the protein. In certain embodiments, the present invention comprises antibodies that recognize and are specific for one or more epitopes of a membrane repair polypeptide, MG53, membrane repair polypeptide binding protein, MG53 binding protein, membrane repair polypeptide receptor, and/or MG53 receptor protein, variants, portions and/or combinations thereof. In alternative embodiments antibodies of the invention may target and interfere with the MG53/MG53 receptor interaction to inhibit signaling.

The preparation of monoclonal antibodies is well known in the art; see for example, Harlow et al., Antibodies: A Laboratory Manual, page 726 (Cold Spring Harbor Pub. 1988). Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind to membrane repair polypeptide, MG53, membrane repair polypeptide binding protein, MG53 binding protein, membrane repair polypeptide receptor, and/or MG53 receptor proteins or fragments thereof (as described in, e.g., Ladner et al. U.S. Pat. No. 5,223,409; Fuchs et al. (1991) Bio/Technology 9:1370-1372; Hay et al. (1992) Hum Antibod Hybridomas 3:81-85; Huse et al. (1989) Science 246:1275-1281; Clackson et al. (1991) Nature 352:624-628; Gram et al. (1992) PNAS 89:3576-3580. Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855). A therapeutically useful antibody to the components of the complex of the invention or the complex itself may be derived from a "humanized" monoclonal antibody. Humanized monoclonal antibodies are produced by transferring mouse complementarity determining regions (CDRs) from heavy and light variable chains of the mouse immunoglobulin into a human variable domain, then substituting human residues into the framework regions of the murine counterparts.

The use of antibody components derived from humanized monoclonal antibodies obviates potential problems associated with immunogenicity of murine constant regions. Techniques for producing humanized monoclonal antibodies can be found in Jones et al., Nature 321: 522, 1986 and Singer et al., J. Immunol. 150: 2844, 1993; Wu T. T. and Kabat, E. A. (1970) J. Exp. Med., 132: 211-250; and Johnson G., Wu, T. T. and Kabat, E. A. (1995) In Paul, S. (ed.), Antibody Engineering Protocols. Humana Press, pp. 1-15, which are incorporated herein by reference. The antibodies can also be derived from human antibody fragments isolated from a combinatorial immunoglobulin library; see, for example, Barbas et al., Methods: A Companion to Methods in Enzymology 2, 119, 1991. In addition, chimeric antibodies can be obtained by splicing the genes from a mouse antibody molecule with appropriate antigen specificity together with genes from a human antibody molecule of appropriate biological specificity; see, for example, Takeda et al., Nature 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

In certain embodiments of the invention, at least one epitope encompassed by the antigenic peptide is a region of membrane repair polypeptide, MG53, membrane repair polypeptide binding protein, MG53 binding protein, membrane repair polypeptide receptor, and/or MG53 receptor that is located on the surface of the protein, e.g., a hydrophilic region. A hydrophobicity analysis of the protein sequence will indicate which regions of a polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, *J. Mol. Biol.* 227:381 (1991); Marks et al., *J. Mol. Biol.*, 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and in Marks et al. (*Bio/Technology*, 10:779-783 (1992)); Lonberg et al. (*Nature*, 368:856-859 (1994)); Morrison (*Nature*, 368:812-13 (1994)); Fishwild et al, (*Nature Biotechnology*, 14:845-51 (1996)); Neuberger (*Nature Biotechnology*, 14:826 (1996)); and Lonberg and Huszar (*Intern. Rev. Immunol.*, 13:65-93 (1995)).

Human antibodies may additionally be produced using transgenic nonhuman animals which are modified so as to produce fully human antibodies rather than the animal's endogenous antibodies in response to challenge by an antigen. The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096.

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 500 mg/kg body weight.—Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York. The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., Fab or F(ab)2) can be used. The term "labeled", with regard to the probe or antibody, is intended to encompass direct labeling of the probe or antibody by coupling (i e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbant assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques intracavity, or transdermally, alone or with effector cells.

Preparations for administration of the therapeutic of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The compounds, nucleic acid molecules, polypeptides, and antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. *Proc. Natl. Acad. Sci.* USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

Also disclosed according to the present invention is a kit or system utilizing any one of the methods, selection strategies, materials, or components described herein. Exemplary kits according to the present disclosure will optionally, additionally include instructions for performing methods or assays, packaging materials, one or more containers which contain an assay, a device or system components, or the like.

Additional objects and advantages of the present invention will be appreciated by one of ordinary skill in the art in light of the current description and examples of the preferred embodiments, and are expressly included within the scope of the present invention.

Examples

Discovery of MG53, a muscle specific TRIM family protein. MG53 was isolated using a previously established an immuno-proteomic approach that allows identification of novel proteins involved in myogenesis, $Ca^{2+}$ signaling and maintenance of membrane integrity in striated muscle cells. Briefly, this approach uses a monoclonal antibody library containing ~6500 clones that was generated from mice immunized with triad-enriched membranes from rabbit skeletal muscle. Antibodies of interest were selected based on the z-line staining patterns of striated muscle sections observed under an immunofluorescence microscope. The target-proteins were purified through antibody-affinity column, and partial amino acid sequences of the purified proteins were obtained. Based on the partial amino acid sequence, the complete cDNA coding for the target gene was isolated from a skeletal muscle cDNA library. Homologous gene screening was then used to search for the presence of different isoforms of the identified genes in other excitable tissues. Finally, transgenic or knockout mouse models were generated to study the in vivo physiological function of genes of interest.

Figure 2:
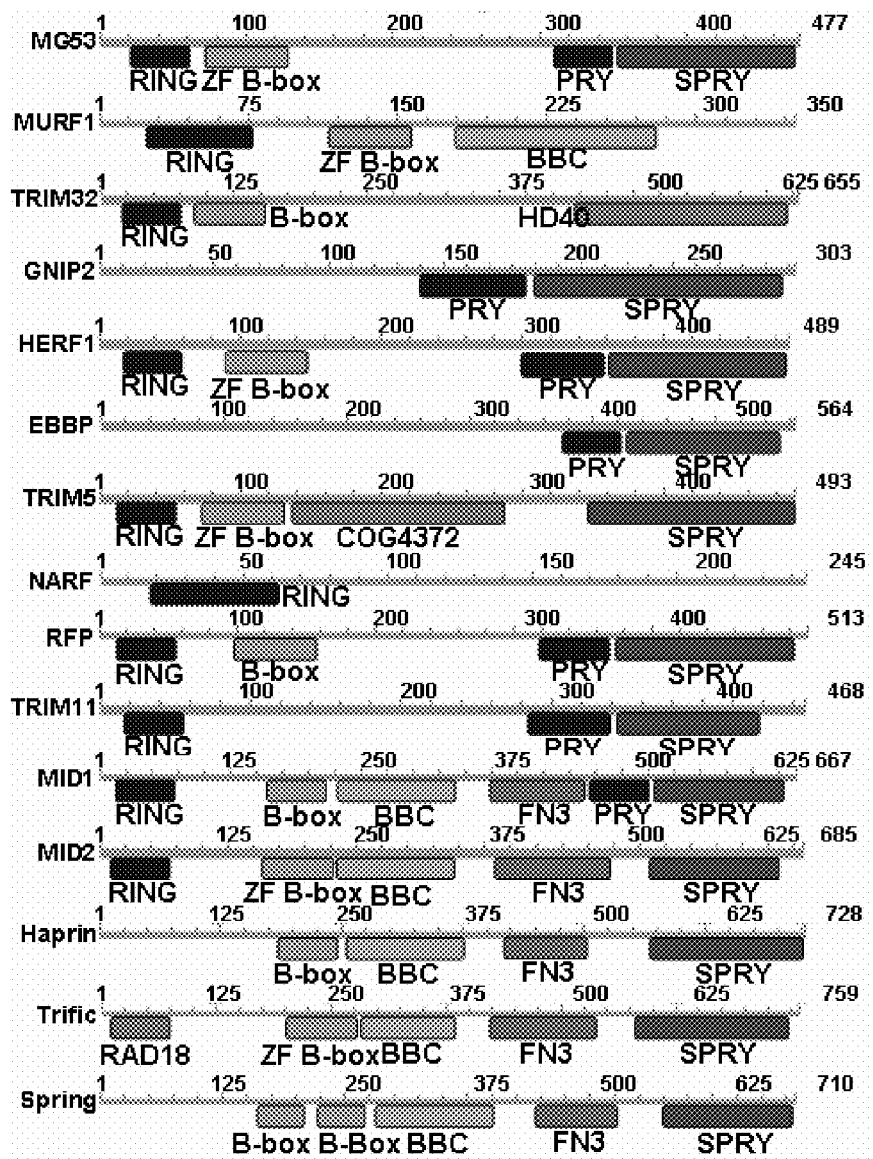
FIG. 2: Illustrates an exemplary domain comparison of some homologous proteins that contain one or more of the conserved tripartite motifs which are present in MG53. MG53 is unique in it's ability to translocate to an injury site at the cell membrane following multiple forms of insult and mediate repair of the damaged membrane—a function which is not exhibited by the other TRIM family proteins listed. While these TRIM proteins all contain similar domains and/or are expressed in striated muscle, none fully recapitulate the domain organization of MG53.
Figure 3:
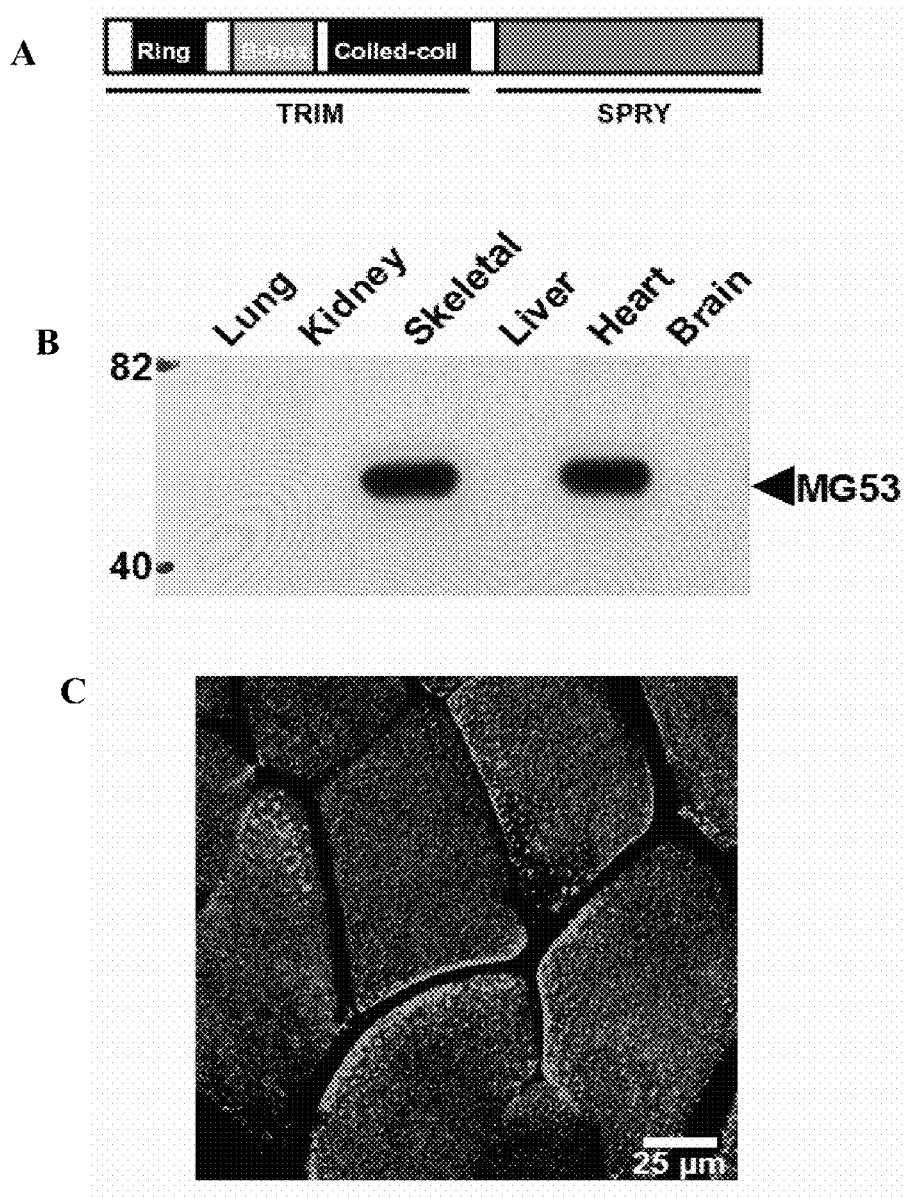
FIG. 3: MG53 contains unique TRIM and SPRY motifs and is predominantly expressed in muscle cells. A. Diagram of motif structure of MG53. From the results of cDNA cloning and homology searches, several motif sequences are detected in MG53 as shown. The sequences of rabbit and mouse MG53 cDNAs have been deposited in the databases under accession numbers AB231473 and AB231474, respectively. B. Western blot analysis shows the specific expression of MG53 in skeletal and cardiac muscles. Lysate (20 µg total protein per lane) from mouse tissues (lung, kidney, skeletal muscle, liver, heart, brain) were analyzed using anti-mouse MG53 polyclonal antibody. C. Immunofluorescence staining of longitudinal transverse sections from mouse skeletal muscle cells. Scale bar is 125 µm.
Figure 1B:
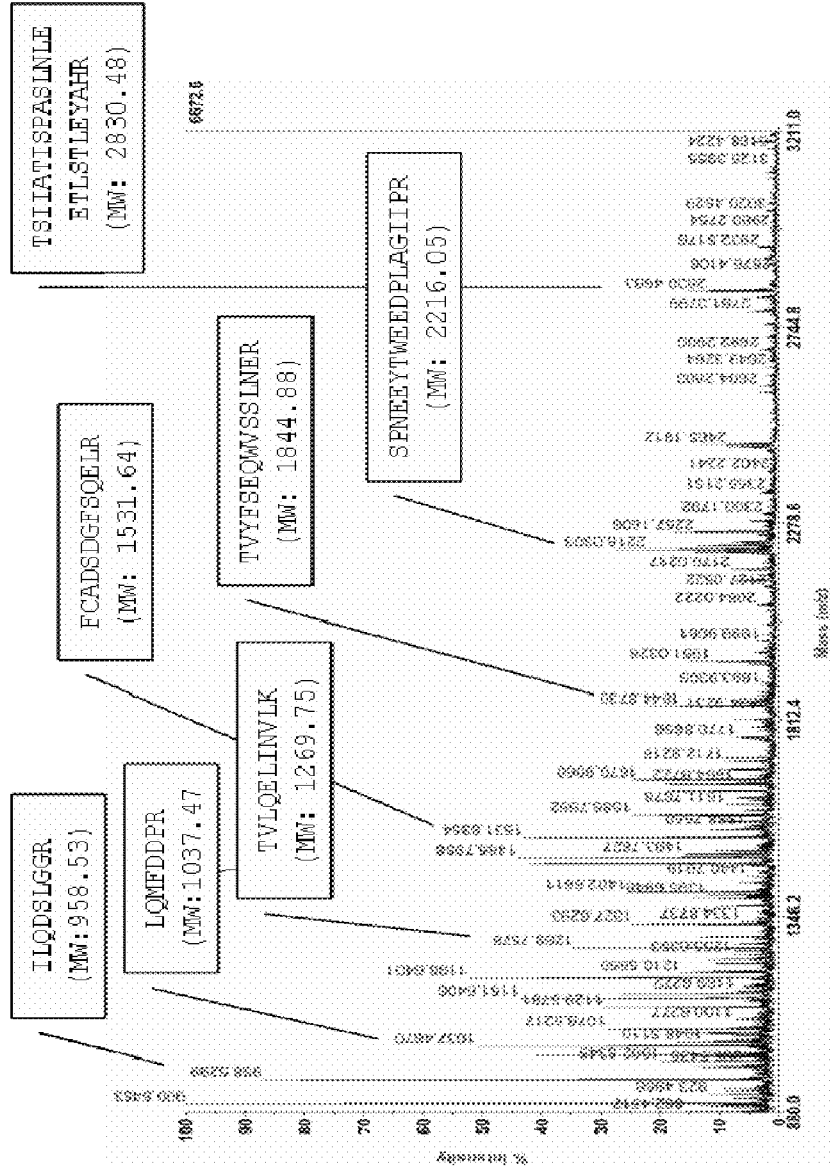
FIG. 1: MG53 is a muscle specific member of the TRIM protein family. An alignment of the protein sequence of MG53 from various organisms (See SEQ ID NOs.: 1, 3, 5, 9-16) reveals this protein to be a member of the TRIM family. Functional domains are boxed in grey while arrows indicate the domain continues onto another line of the sequence. Boxed Leucine residues indicate the location of a highly conserved Leucine zipper motif.

Screening of this immuno-proteomic library for muscle specific proteins led to the identification of an antigen specific proteins led to the identification of an antigen recognized by mAb5259 with a molecular size of 53 kilodaltons (kDa) specifically with striated muscle tissues (FIG. 3B). The protein, "MG53", was partially purified from rabbit skeletal muscle by a mAb5259 immunoaffinity column and subjected to amino acid sequencing. Skeletal muscle cDNA library screening and genomic database searches identified the predicted amino acid sequences for MG53 and the corresponding mg53 gene on the human 16p11.2 locus. Northern blotting for the mg53 mRNA confirmed specific expression with skeletal and cardiac muscle (FIG. 3C). Domain homology analysis revealed that MG53 contains the prototypical tri-partite motifs that include a Ring, B-box and Coiled-Coil (RBCC) moieties, as well as a SPRY domain at the carboxyl-terminus (FIGS. 1, 2, and 3A). The SPRY domain is a conserved sequence first observed in the ryanodine receptor $Ca^{2+}$ release channel in the sarcoplasmic reticulum of excitable cells. Of the approximately 60 TRIM family members so far identified in various mammalian genomes, 15 members carry a similar SPRY domain following the RBCC domain, and MG53 shows a conserved primary structure with these TRIM sub-family proteins.

MG53 mediates vesicle trafficking in muscle cells. Although there is no membrane-spanning segment or lipid-modification motif in its primary structure, MG53 appears to be primarily restricted to membrane structures in skeletal muscle. Immunohistochemical analysis revealed specific labeling for MG53 in the sarcolemma membrane and intracellular vesicles (FIG. 3D). MG53 is a muscle-specific protein that contains TRIM and SPRY motifs. In previous studies we have established a monoclonal antibody (mAb) library that targets proteins associated with the triad junction in skeletal muscle. Screening of this immuno-proteomic library for muscle specific proteins led to the identification of an antigen named MG53 with a molecular size of 53 kilodaltons (kDa), which was recognized by mAb5259. MG53 was partially purified from rabbit skeletal muscle by an immunoaffinity column conjugated with mAb5259, and subjected to amino acid sequencing. Based on the obtained partial amino acid sequences, cDNAs encoding MG53 were isolated from rabbit and mouse skeletal muscle libraries. Genomic library search identified the corresponding MG53 gene on the human 16p11.2 locus. The predicted amino acid sequences for MG53 in several species are shown in FIG. 1.

Domain homology analysis revealed that MG53 contains the prototypical TRIM signature sequence of RBCC plus a SPRY domain at the carboxyl-terminus, and thus belongs to the TRIM/RBCC family (FIG. 1). Of the approximately 60 TRIM family members so far identified in the mammalian genomes, 15 members carry a similar SPRY domain following the RBCC domain, and MG53 shows a conserved primary structure with these TRIM sub-family proteins (FIG. 2). However, surprisingly and unexpectedly our studies indicate that MG53 is the only TRIM family protein of those in FIG. 2 that demonstrate membrane repair function.

Western blot assay confirms the muscle-specific expression of MG53 in mouse tissues (FIG. 3B). Although there is no membrane-spanning segment or lipid-modification motif in its primary structure, MG53 appears to be primarily restricted to membrane structures in skeletal muscle Immunohistochemical analysis with mAb5259 showed specific labeling for MG53 in the sarcolemmal and TT membranes in transverse sections of skeletal muscle fibers (FIG. 3C). Moreover, transverse sections revealed localized concentration of MG53 near the sarcolemmal membrane, with a broader staining pattern than is typically observed for integral membrane proteins of the sarcolemma. Thus, MG53 is a muscle specific TRIM family protein that displays a unique subcellular distribution pattern for a TRIM family protein.

Figure 4:
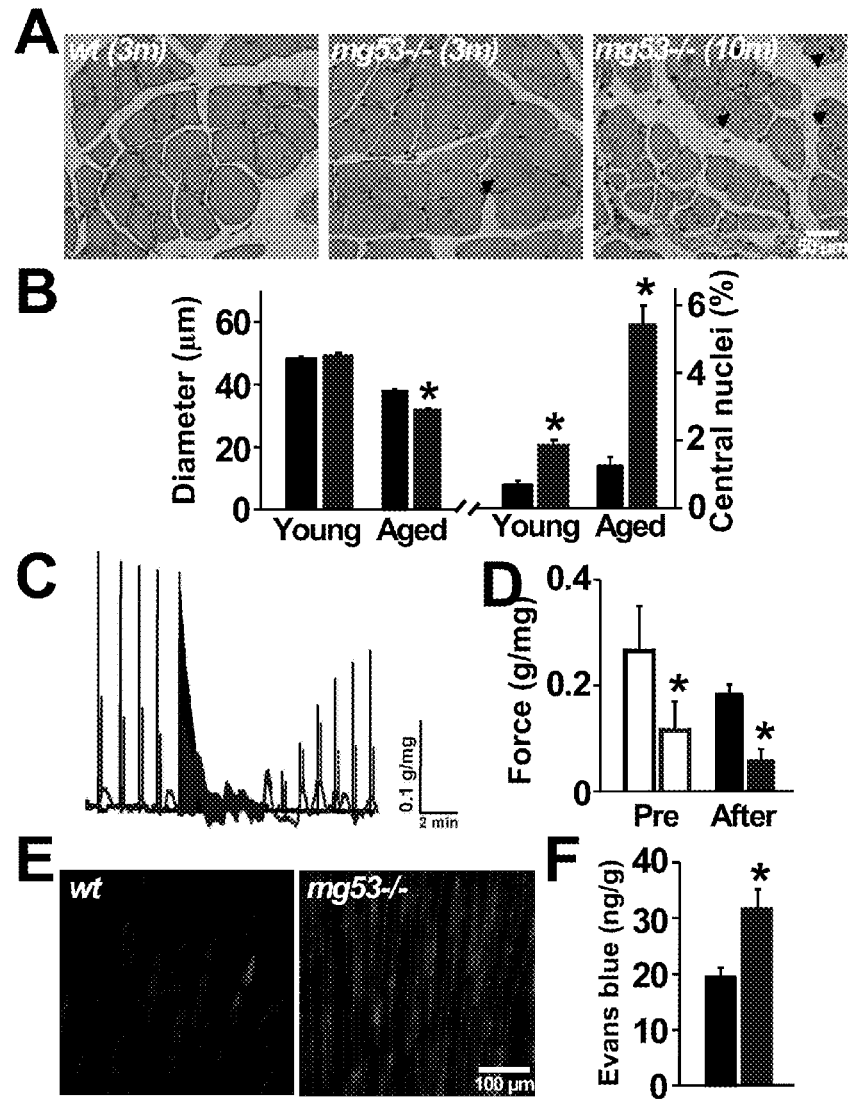
FIG. 4. Progressive pathology is seen in mg53−/− skeletal muscle due to increased damage of cell membranes. A. Haematoxylin and Eosin (H/E) staining illustrates increased number of central nuclei (arrows) in aging mg53−/− muscle (10 m) versus young (3 m) wild type (wt) or mg53−/− mice. B. The diameter of muscle fibers in aged (8-10 month) mg53−/− mice (blue, n=541) decreased compared to aged (8-10 month) wild type controls (black, n=562) while there is no difference in young (3-5 months) wt (n=765) versus mg53−/− (n=673) muscle. Percentage of muscle fibers that display central nuclei in mg53−/− skeletal muscle increases with age when compared to wt. Data is mean±s.e.m., * p<0.05 by ANOVA. C. Trace recordings of contractile performance of intact soleus muscle obtained from mice subjected to 30 min down-hill exercise running was assessed using an in vitro voltage stimulation protocol, following described procedures. Black trace represents wt muscle, blue trace corresponds to mg53−/− muscle. D. Prior to fatigue stimulation (Pre, open bars), the maximal tetanic force, normalized in g/mg total protein, was significantly lower in aging mg53−/− muscle (blue) versus wt (black) (n=4). At 6 min after fatigue stimulation (After, closed bars), the wt muscle recovered significantly more than mg53−/− muscle. * p<0.05 by ANOVA. E. Extensive Evans blue staining reveals serve damage in mg53−/− skeletal muscle subjected to down-hill running when compared to minimal staining in wt muscles. F. Chart of the quantity of Evans blue dye extracted by formamide from aging mg53−/− (blue) and wt (black) skeletal muscle following exercise. The data represents mean value of Evans blue (ng) per g of muscle ±s.e.m. n=8-12, * p<0.005 by Student's t-test.

MG53 mediates acute membrane repair in skeletal muscle fibers following cellular injury. To further define the physiological function of MG53 in muscle membrane repair, a mouse model null for MG53 was generated. The mg53−/− mice are viable up to 11 month of age under unstressed conditions. In vivo stress tests revealed severe defects in membrane repair function of the mg53−/− muscle. As shown in FIG. 4C, membrane injury induced by down-hill running exercise revealed severely compromised contractile function of the soleus muscle from the mg53−/− mice. Without the strenuous exercise, mg53−/− soleus muscles displayed some difficulty in recovery of contractile function after ex vivo fatigue stimulation, compared with the wild type (wt) controls (not shown). These differences can be drastically exaggerated following exercise-induced damages at 8-10 month of age. Clearly, more severe damage could be found with the mg53−/− muscle, where weaker and fluctuating contractile function was observed in comparison with the wt muscle (FIG. 4D).

Injection of Evans blue dye into the intraperitoneal space of mice directly monitors sarcolemmal membrane integrity after down-hill exercise-induced muscle damage. As shown in FIG. 4E, muscle fibers isolated from the mg53−/− mice showed significantly more Evans blue staining than the wt muscle, revealing extensive degree of exercise-induced muscle damage. This was confirmed by H/E staining that illustrated increased dystrophy in the mg53−/− muscle that was increased in aged mg53−/− mice compared to young mg53−/− mice (FIG. 4A). Quantitative assay of total absorbance of Evans blue extracted from muscle bundles provided direct support for the increased muscle damage in the mg53−/− mice after down-hill running (FIG. 4F).

Figure 5:
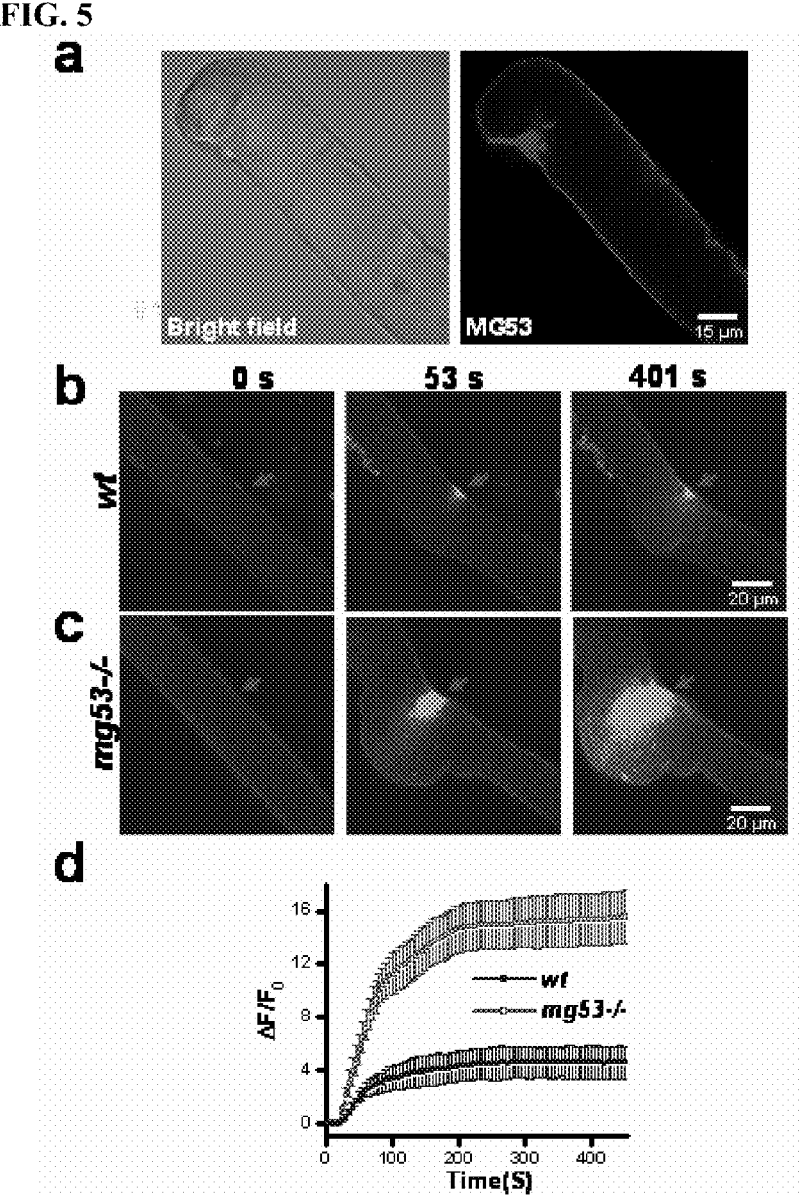
FIG. 5. Ablation of MG53 leads to defective muscle membrane repair function. (a) Immunostaining of MG53 in isolated wt FDB fibers to illustrate their co-localization at the injury site. These are representative images from >20 different muscle fibers which display damage during isolation. (b) Exclusion of membrane-impermeable FM-143 fluorescent dye in a FDB muscle fibers isolated from the wt mice following laser-induced damage of the sarcolemmal membrane. (c) Entry of FM-143 fluorescent dye into a FDB muscle fiber isolated from the mg53−/− mice following laser-induced damage. Times after laser injury were indicated. (d) Time-dependent accumulation of FM-143 inside the FDB muscle fiber induced by a laser damage of the sarcolemmal membrane. Data are means±s.e.m. for n=30 fibers obtained from wt mice and n=18 fibers from mg53−/− mice.

Consistent with the role of MG53 in membrane repair, elevated concentrations of MG53 was observed at the site of injury with immunostaining of individual flexor digitorum brevis (FDB) muscle fibers that were damaged during isolation (FIG. 5A). These membrane patches would frequently co-localize with staining for dysferlin. We directly evaluated the MG53-mediated membrane repair function through measurement of FM-143 fluorescent dye entry after laser-induced membrane damage to individual FDB muscle fibers. The wt muscle fibers possessed intrinsic membrane repair function and were fairly resistant to laser-induced damage of the sarcolemmal membrane, as they displayed effective exclusion of the FM-143 fluorescent dye (FIG. 5B). Significant entry of FM-143 fluorescent dye into the mg53−/− FDB muscle fibers could be observed following laser-induced damage (FIG. 5C). The time-dependent accumulation of FM-143 inside the FDB muscle fibers following laser damage of the sarcolemmal membrane provides direct support for a defective membrane repair function of the mg53−/− muscle (FIG. 5D).

Figure 6:
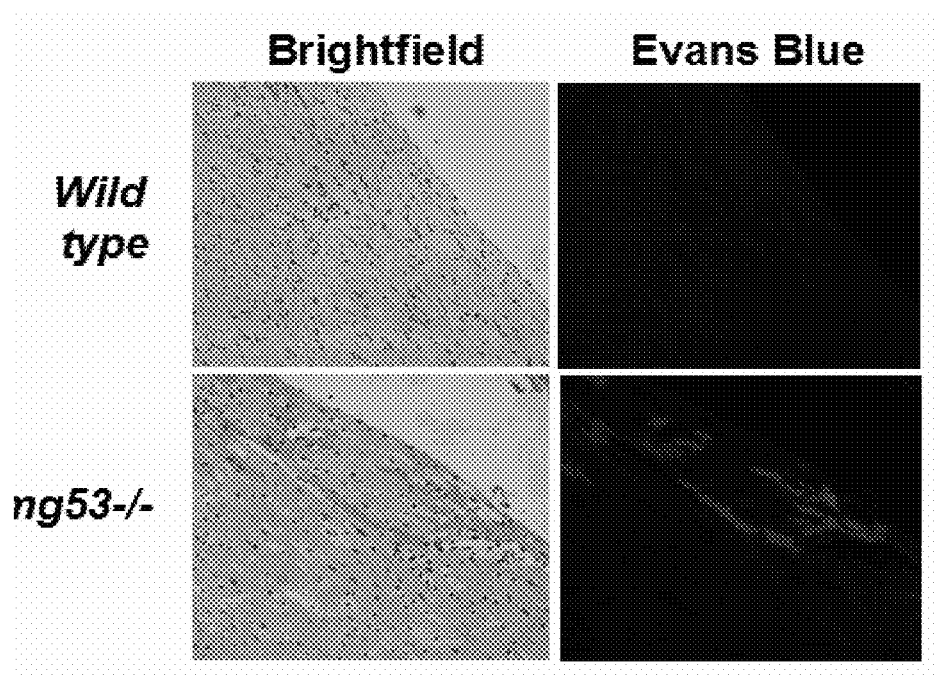
FIG. 6. MG53 knockout mice are susceptible to cardiac damage. Paraffin-embedded sections of myocardium from unexercised wild type mice show normal morphology (left)

Expression of MG53 is essential to maintain normal cardiac membrane integrity. Defects in mg53−/− mice are not limited to skeletal muscle fibers. During injection of Evans blue dye ~50% of the mg53−/− mice would die within 16 hours of injection compared to none of the wild type animals injected. Postmortem examination of mg53−/− hearts revealed extensive labeling of cardiac muscle fibers with Evans blue, even in absence of exercise stress (FIG. 6). We also found that exercise would greatly exacerbate the extent of Evans blue staining in mg53−/− hearts.

Loss of MG53 increases susceptibility to cardiac ischemia reperfusion injury (FIG. 7). Hearts from wild type (WT) and mg53−/− (mg53KO) mice were isolated and perfused on a Langendorff apparatus. Global ischemia was induced for 30 minutes by cessation of perfusate flow. The damage produced in the heart following restoration of perfusate flow (time 0) was measured by enzymatic assays for (a) creatine kinase (CK) or (b) lactate dehydrogenase (LDH). Hearts from mg53−/− mice (dashed lines) show more damage than WT (solid lines). Data is presented as mean±S.D. for each listed time point.

Vesicle fusion with the plasma membrane is required for membrane repair and previous studies indicate a role for dysferlin in maintenance of skeletal muscle membrane integrity. Our findings indicate that MG53 is capable of driving the trafficking of vesicles to the plasma membrane, perhaps to mediate the repair process following membrane disruption. Acute cellular injury generated by physical penetration of the plasma membrane with a microelectrode leads to rapid recruitment of GFP-MG53 vesicles toward the injury site (FIG. 8A). When more severe damage that results in fracture of the cell occurs, the repair site is densely labeled with GFP-MG53 (FIG. 8B). In addition, this acute membrane repair also was observed in mature C2C12 myotubes. This data indicates that MG53-mediated vesicle trafficking play an active role in acute repair of cell membrane.

The function of MG53 appears to be essential to allow membrane patching and survival of muscle cells following injury. When myoblasts are isolated from wild type and mg53 knockout (mg53$^{-/-}$) mice and differentiated to form myotubes, the mg53$^{-/-}$ myotubes cannot recover from mechanical injury induced by microelectrode penetration (FIG. 8). This indicates that MG53 is essential for membrane resealing and cell survival in muscle, as the wild type myotubes can reseal their membrane and survive injury while mg53$^{-/-}$ myotubes cannot (FIG. 8C). This confirms the functional role of MG53 in membrane resealing, and indicated that MG53 is essential for membrane resealing in striated muscle.

Role of TRIM and SPRY motifs in MG53 function. Structure/function assessment of the domains of MG53 (FIG. 9) revealed a remarkable polarity of GFP fusion to MG53 in the intracellular distribution of MG53. In particular, fusion of GFP to the carboxyl-terminal end of MG53 alters the ability of MG53 to partition to the vesicular compartment and to target to the sarcolemmal membrane. To further test the function of the TRIM and SPRY domains in facilitating the membrane-fusion function of MG53, a series of deletion mutants coupled to GFP (FIG. 9A) were generated.

To analyze the subcellular localization of these mutant constructs of MG53, confocal microscopic imaging was applied to C2C12 myoblasts following transient expression. As shown in FIG. 9B (right panels), GFP-TRIM or TRIM-GFP were predominantly localized to intracellular vesicles without apparent labeling of the sarcolemmal membrane. This result suggests that the SPRY domain, which is absent from GFP-TRIM or TRIM-GFP, is necessary for targeting of MG53 to the sarcolemmal membrane. The fact that MG53-GFP exhibited a predominantly cytosolic distribution (FIG. 9B, left panel), further supports the role of SPRY in targeting MG53 to the cell surface membrane.

Interestingly, although GFP-SPRY or SPRY-GFP displayed a predominantly cytosolic pattern of distribution, they are clearly excluded from intracellular vesicles (FIG. 9B, middle panels). The cytosolic distribution pattern coupled with the exclusion of localization at intracellular vesicles of GFP-SPRY and SPRY-GFP likely reflects the role of TRIM. Presumably, the TRIM motif can mediate the adherence of MG53 to intracellular vesicles (FIG. 9B, right panels). The SPRY domain is insufficient to target to the sarcolemma by itself, therefore the TRIM domain must be present in tandem with the SPRY domain for proper trafficking of MG53 to the sarcolemmal membrane.

MG53 cab interact with caveolin-3 (Cav-3). In addition, our co-immunoprecipitation data shows that caveolin-3 interacts with the TRIM motif of MG53 (FIG. 9C). Thus, it is possible that the functional interaction between MG53 and caveolin-3 may underlie some of the cellular factors contributing to the diffuse pattern of GFP-SPRY and SPRY-GFP in C2C12 myoblasts. Overall, the regulated distribution of MG53 to the cell surface and intracellular compartments would likely result from coordinated action between the TRIM and SPRY domains. This requirement for both TRIM and SPRY for proper MG53 subcellular localization also has apparent functional significance, as none of these deletion mutants display the filapodia-like structures or the robust vesicle budding events observed from overexpression of full-length MG53.

MG53 can fully function in non-muscle cell types. Analysis of MG53 function in myogenic C2C12 cells and in isolated skeletal muscle fibers reveals an essential role for MG53 in vesicle trafficking and membrane repair in striated muscle. Considering that membrane repair is an essential to maintain cellular homeostasis, it is likely that similar repair mechanisms in other non-muscle cell types could use similar molecular machinery to facilitate this process. To test this possibility, several of the previous experiments conducted with C2C12 myogenic cells were replicated with non-muscle Chinese hamster ovary (CHO) cells. In these cells, a very similar phenotype to that seen in the C2C12 cells was found. First, GFP-MG53 could produce filapodia-like protrusions of the plasma membrane and localize to both intracellular vesicles and to the plasma membrane. Second, MG53 deletion proteins behaved in an identical fashion to that seen in C2C12 cells. Finally, caveolin-3 can also control the activity of MG53 expressed in CHO cells. As a result, these studies indicate that MG53 acts through a conserved molecular mechanism that is present in other cell types besides muscle.

MG53 can fully function in non-muscle cell types. Analysis of MG53 function in myogenic C2C12 cells and in isolated skeletal muscle fibers reveals an essential role for MG53 in vesicle trafficking and membrane repair in striated muscle. Considering that membrane repair is an essential to maintain cellular homeostasis, it is likely that similar repair mechanisms in other non-muscle cell types could use similar molecular machinery to facilitate this process. To test this possibility, several of the previous experiments conducted with C2C12 myogenic cells were replicated with non-muscle Chinese hamster ovary (CHO) cells. In these cells, a very similar phenotype to that seen in the C2C12 cells was found. First, GFP-MG53 could produce filapodia-like protrusions of the plasma membrane and localize to both intracellular vesicles and to the plasma membrane (FIG. 10). Second, MG53 deletion proteins behaved in an identical fashion to that seen in C2C12 cells. Finally, caveolin-3 can also control the activity of MG53 expressed in CHO cells (FIG. 10). As a result, these studies indicate that MG53 acts through a conserved molecular mechanism that is present in other cell types besides muscle.

MG53 can interact with Kinesin family member 11 (Kif11). Cell lysates were isolated from HEK293 cells stably expressing FLAG-tagged versions of either RFP (mRFP), RFP-MG53 (MG53) or C29L mutant RFP-MG53 (C29L). Extracts were co-immunoprecipitated with anti-FLAG antibody and then run on a SDS-PAGE gel. Commassie staining revealed specific bands that we co-IP by this approach. One prominent band was for Kif11 (arrowhead) (FIG. 11a). Mass spectroscopy was used to identify particular bands from these gels. This representative mass spectroscopy tracing shows that MG53 can pull down Kif11 from cell lysates (FIG. 11b).

MG53 can interact with COP9 complex homolog subunit 6 (CSN6). HEK293 cells were transiently transfected with HA-tagged human MG53 and myc-tagged CSN6 and then used for co-immunoprecipitation (IP) using antibodies against the recombinant tags (FIG. 12). The presence of the protein following pull down was confirmed using Western immunoblots (IB). In some cases, a proteosome inhibitor, MG132, was also added to maintain protein stability during protein overexpression. We find that MG53 can pull down CSN6 and that CSN6 can also pull down MG53. This provides evidence that these two proteins can interact within the cell. Lanes 1=HA-hMG53+hCSN6+DMSO, Lanes 2=HA-hMG53+hCSN6+MG132, Lanes 3=HA-mMG53+hCSN6+DMSO, Lanes 4=HA-mMG53+hCSN6+MG132.

MG53 can interact with myelin basic protein or periaxin. Schematic diagrams of methods for biochemical isolation of vesicle fractions from either wild type (WT) or mg53-/- (KO) skeletal muscle (FIG. 13a). Fractions isolated with methods presented in a were run on with 15% (left) of gradient (right) SDS-PAGE gels. Brilliant Blue (CBB) staining revealed specific bands that we differentially present in WT or KO muscle (FIG. 13b). Two prominent bands were identified as myelin basic protein or periaxin (arrows) by mass spectroscopy.

MG53 interacts with cellular membranes through an association with phosphatidylserine to mediate vesicular trafficking. When GFP-MG53 is expressed in these mg53 (−/−) myotubes, the protein will properly localize to the plasma membrane and intracellular vesicles (FIG. 14A, top). When these mg53(−/−) myotubes are injured the GFP-MG53 can localize to the injury site. (FIG. 14A, bottom). Lipid profiling (22) revealed that the purified recombinant MG53 could interact with phosphatidylserine (PS), lipids that preferentially appear at the inner leaflet of the plasma membrane and the cytoplasmic face of intracellular vesicles. $PIP_2$-Strip lipid dot blot analysis reveals recombinant MG53 (1 µg/ml) specifically binds phosphatidylserine (PS) and not other membrane lipids, including sphingosine-1-P, phosphatidic acid, phosphotidylcholine, phosphatidylethanolamine and various phosphainositol metabolites (FIG. 14B). Using Annexin-V-GFP, we observed rapid labeling of Annexin-V-GFP at the C2C12 myoblast injury site. Annexin-V-GFP (a molecule with well defined ability to bind PS) transfected into C2C12 myoblasts displays minimal translocation following cell wounding with a microelectrode (left), while co-expression of Annexin-V-GFP with RFP-MG53 (right) results in accelerated accumulation of Annexin-V-GFP. (FIG. 14C). The accumulation of Annexin-V-GFP was accelerated by co-expression of RFP-MG53 (0.93±0.21 $\Delta F/F_0$ control; 2.9±0.63 $\Delta F/F_0$+MG53), consistent with a role for MG53 in mediating repairsome formation at the injury site. Entry of extracellular $Ca^{2+}$ through the damaged plasma membrane allowed Annexin-V binding to PS, leading to its transition from a soluble pattern before cell injury to distinct localization to plasma membrane and intracellular vesicles (FIG. 14D). Removal of $Ca^{2+}$ from the extracellular solution disrupted the labeling of PS by Annexin-V-GFP at the injury site, translocation of RFP-MG53 to the injury site was maintained (FIG. 14E).

Cys242 allows MG53 to acts as a sensor of cellular redox state and reseal cellular membranes. Thimerosal oxidizes sulfhydryl groups at cysteine residues, which provided a mutagenesis target to identify specific amino acids that underlie oxidation-mediated oligomerization of MG53. Multiple conserved cysteine residues were mutated into alanines. One particular mutation, C242A, resulted in complete loss of MG53 oligomerization property (FIG. 15A). This mutation maintained membrane targeting, but completely disrupted its ability to facilitate the membrane repair process (FIG. 15E); i.e., no accumulation of C242A was observed at the injury site. A respective conserved cysteine mutant, C313A, maintained oligomerization pattern under oxidized conditions and displayed similar translocation and membrane-repair function as the wild type GFP-MG53 (FIG. 16). Under a reduced extracellular environment (+DTT), translocation of GFP-MG53 toward the injury site was largely disrupted. The addition of an oxidizing agent (Thimerosal) into the extracellular solution results in an increased translocation of GFP-MG53 to injury sites on the cell membrane. These experiments were conducted in C2C12 cells. MG53 with a C242A mutation (GFP-C242A) cannot translocate to injury sites on the plasma membrane. Since a different conserved cysteine mutant, C313A, maintained oligomerization pattern under oxidized conditions and displayed similar translocation and membrane-repair function as the wild type GFP-MG53. Thus, the oxidation of Cys242 likely induces oligomerization of MG53, providing a nucleation site for repairsome formation at injury sites. These experiments were conducted with C2C12 cells. Modulation of the extracellular redox state can affect the resealing of isolated muscle fiber membranes as the addition of DTT to the extracellular solution prevents membrane resealing, as measured by an increase in entry of FM-143 dye applied outside of the cell. Thus, the oxidation of Cys242 likely induces oligomerization of MG53, providing a nucleation site for repairsome formation at injury sites.

MG53-mediated repairsome formation and restoration of acute sarcolemma membrane damage is shown in FIG. 17. The entry of FM4-64, a red-shifted variant of FM1-43, was used as an index of membrane repair capacity in mg53−/− myotubes transfected with GFP-MG53 and GFP-C242A. Following UV-bleaching of the green fluorescence, rapid translocation of GFP-MG53 took place at the injury site, whereas GFP-C242A remained static due to its defective oligomerization properties (FIG. 16E, 17A). Significantly less entry of FM4-64 was observed in cells transfected with GFP-MG53 compared with GFP-C242A, suggesting that the mutant was not able to restore membrane integrity following injury (FIG. 17B). This data provides direct support that MG53 translocation to sites of injury results in membrane resealing. Oligomerization of MG53 appears to be an essential step in repairsome formation, as the GFP-C242A mutant expressed in wt skeletal muscle displayed a dominant negative function over the native MG53 (FIG. 17C). Compared with GFP-MG53, overexpression of GFP-C242A in adult wt muscle fibers inhibited sarcolemmal membrane repair function (FIG. 17C).

Several TRIM-family proteins with diverse cellular functions that contain conserved Ring-finger motifs have been shown to display E3-ligase activity. To test whether MG53 can catalyze ubiquitination in vitro, we prepared a recombinant maltose-binding protein (MBP) fusion protein for MG53. MBP-MG53 was incubated with ATP, ubiquitin, E1 and E2 enzymes, and subjected to immunoblotting with the anti-MBP antibody. High molecular-mass ladders derived from ubiquitination were observed when MBP-MG53 was incubated with Ubc4 or UbcH5 as E2 (FIG. 18a and data not shown). The exclusion of either ubiquitin, E1 or E2 (UbcH5) from the assay abolished the appearance of such ladders, confirming that the modification acquired by MBP-MG53 was indeed auto-ubiquitination. When a conserved cysteine residue (Cys-29) in the Ring-finger motif of MG53 was replaced with leucine (C29L), the intrinsic E3-ligase activity of MG53 was significantly reduced (FIG. 18b). Thus, MG53 is a Ring-finger type ubiquitin ligase that couples with Ubc4/5 sub-family of E2 enzymes.

To test the functional impact of the C29L mutation in MG53, we compared the subcellular distribution of GFP-MG53 and GFP-C29L expressed in C2C12 myotubes. Strikingly, the unique membrane-partition and vesicular tethering of GFP-MG53 was lost in GFP-C29L, with the mutant protein displaying predominantly a cytosolic pattern in C2C12 myotubes (FIG. 18d, left). Western blot demonstrated that the full-length GFP-MG53 and GFP-C29L proteins were present in the differentiated C2C12 myotubes (FIG. 18c), thus it is unlikely that degradation of these fusion proteins contributes to the different subcellular distribution of GFP-C29L and GFP-MG53 observed in FIG. 18d. Furthermore, similar phenomena were observed with transient expression of these fusion proteins into primary cultured skeletal myotubes derived from the mg53−/− neonates, where targeting of GFP-MG53 to sarcolemmal membrane and intracellular vesicles were attenuated for the GFP-C29L mutant (FIG. 18d, right). Similar to the adult mg53−/− muscle fibers that displayed defective membrane repair function (shown previously), the primary cultured mg53−/− myotubes were also defective in membrane repair compared with the wt control, thus providing a homologous reconstruction system to test the cellular function of MG53.

Further studies show that alterations to membrane-trafficking and membrane-partition properties of GFP-C29L lead to defective membrane repair function of MG53. Following acute membrane damage, rapid accumulation of GFP-MG53 is observed in C2C12 myoblasts, whereas GFP-C29L appeared to be immobile and ineffective in repair of membrane injury (FIG. 18e, left). Similar defects with GFP-C29L were also observed in C2C12 myotubes (FIG. 18e, middle). Moreover, while GFP-MG53 could translocate to the plasma membrane following injury in primary cultured mg53−/− myotubes, GFP-C29L expressed in these cells remained generally unresponsive to acute cell injury (FIG. 18e, right). Together, these results show that loss of E3-ligase activity associated with C29L mutation likely caused defective trafficking of MG53, underlying the defective membrane repair function of MG53.

The Ring domain of MG53 also contains a zinc finger motif, which is known to bind Zn to facilitate enzymatic action in numerous proteins. To test if Zn could contribute to the MG53 function in membrane repair, we tested the effect of removing Zn from the extracellular solution before wounding C2C12 myoblasts expressing GFP-MG53. We found that chelating Zn with N,N,N,N-tetrakis(2-pyridyl-methyl)ethylenediamine (TPEN) could prevent the translocation of GFP-MG53 to the site of microelectrode penetration (FIG. 19A), indicating that Zn was necessary for MG53 function. Addition of a Zn ionophore, Zn-1-hydroxypyridine-2-thine (Zn-HPT), could induce the translocation of GFP-MG53 in C2C12 cells (FIG. 19B), suggesting that additional Zn can induce increased MG53 function. This observation was confirmed in wild type FDB muscle fibers, as addition of Zn-HPT to these cells could reduce the amount of FM-1-43 dye that can enter the muscle fiber following injury induced by a UV laser (FIG. 19C). These results indicate that the presence of Zn is vital for the function of MG53, and suggest that provide additional Zn can increase the function of MG53 in membrane resealing. The implication of these results is that function of recombinant MG53 protein used for a therapeutic application could be increased by the addition of Zn into the formulation for the MG53 protein.

Protective effect of zinc on membrane repair is lost in mg53−/− skeletal muscle. To access membrane repair capacity, individual flexor digitorum brevis (FDB) muscle fibers were isolated from wild type (WT) mice (3-6 months) (FIG. 20a). A strong UV laser was applied to the FDB fiber that caused local damage to the muscle (arrow). Entry of FM1-43 fluorescent dye (2.5 μM) was used as an indicator for the measurement of membrane repair capacity. The images were taken 200 s following UV irradiation (control). Application of 2 μM zinc-ionophore (1-hydroxypyridine-2-thione) (+Zn-HPT) led to increased membrane repair capacity as reflected by the decreased amount of FM1-43 dye entry following UV-damage. Addition of 40 μM TPEN (Tetrakis-2-pyridyl-methylenediamine), a specific buffer for zinc ions, led to compromised membrane repair capacity, as reflected by the significant increase in FM1-43 dye entry following UV-damage (+TPEN). FDB muscle fibers isolated from the mg53−/− mice (3-6 months) exhibited defective membrane repair function, as shown by the elevated amount of FM1-43 dye entry following identical treatment of UV-damage (control) (FIG. 20b). Unlike the WT muscle fibers, the membrane repair capacity observed with mg53−/− muscle fibers did not show dependence with changes in zinc movement across the plasma membrane, e.g. addition of Zn-HPT did not produce protective effect on membrane repair (+Zn-HPT), and buffering of extracellular zinc with TPEN did not produce more entry of FM1-43 dye following UV-damage (+TPEN). Summary data for panel a and b (FIG. 20c). The additional data with Ca-EDTA (100 μM), a reagent that buffers zinc without altering extracellular Ca concentration, also caused compromised membrane repair capacity in WT muscle (left). Treatment with Ca-EDTA did not produce any significant changes in membrane repair capacity in mg53−/− muscle. Overall, these data suggest that zinc-entry across the plasma membrane plays an important role in repair of acute UV-laser induced damage to the WT skeletal muscle. The protective effect of zinc on membrane repair is lost in mg53−/− muscle fibers, indicating that MG53 presumably functions as the receptor or target for zinc during the acute membrane repair process. Schematic diagram of zinc-binding motifs in MG53. The amino-terminus of MG53 contains two putative zinc-binding motifs: one located at the RING motif (a.a. 1-56, human cDNA), and the other located at the B-box motif (a.a. 86-117, human cDNA). The specific amino acids that participate in zinc-binding are indicated (FIG. 20d).

Extracellular zinc entry is essential for MG53-mediated vesicle translocation to acute membrane injury sites. To follow the process of intracellular vesicle translocation associated with repair of acute membrane damage, GFP-MG53 fusion protein was expressed in C2C12 myoblast cells (FIG. 21a). GFP-MG53 displayed localization at the intracellular vesicles and the plasma membrane under resting condition (left). Acute injury of the cell generated by penetration of a microelectrode caused rapid translocation of MG53-containing vesicles at the injury site (arrow, right panel). Incubation of the C2C12 cell with 40 μM Ca-EDTA prevented translocation of GFP-MG53 containing vesicles at the acute injury site (FIG. 21b). Addition of 20 μM TPEN to the extracellular solution also completely abolished the translocation of GFP-MG53 containing vesicles toward the mechanical injury site (FIG. 21c). C2C12 cells transiently transfected with GFP-MG53 was incubated with 20 μM Zn-HPT. Under control condition (0 min), GFP-MG53 was distributed in the cytosol, as well as intracellular vesicles (FIG. 21d). Prolonged incubation with Zn-HPT caused redistribution of GFP-MG53 toward the cell surface membrane and the intracellular membrane compartments (15 min). Summary data with Ca-EDTA and TPEN on GFP-MG53 mediated membrane repair in C2C12 myoblast cells (FIG. 21e). The results show that chelation of extracellular zinc with either Ca-EDTA or TPEN produced significant defects in repair of acute damage to the cell.

Zn-binding to RING and B-box motifs of MG53 is critical for membrane repair. Toward understanding the molecular mechanisms underlying the role of zinc-binding to MG53 in repair of acute damage to cell membrane, we generated several site-specific mutations in the RING and B-box motifs of MG53. These mutant constructs were transiently expressed in C2C12 myoblast cells (FIG. 22). 24 hours after transfection, the cells were harvested and the expression of the various GFP-MG53 mutants was assayed by Western blot with specific antibody against MG53. In the absence of DTT (left panel), with the exception of C242A mutant, all other constructs exhibited oligomeric patterns (marked dimer), indicating that disulfide-cross link of MG53 was maintained with these mutant constructs. With the addition of 10 mM DTT, all mutant constructs displayed monomeric forms of ~75 kD (predicted molecular size of GFP-MG53).

The GFP-C29L mutant expressed in C2C12 cells displayed defective movement toward the acute injury site, in an extracellular solution that contain nominal free zinc (FIG. 50a). Addition of 2 μM Zn-HPT, which serves as ionphore for zinc entry across the plasma membrane, could partially rescue the movement of GFP-C29L toward the acute injury site. GFP-C105S mutant expressed in C2C12 cells could not move to the acute injury site following microelectrode penetration, in an extracellular solution that contain nominal free zinc. Similar to GFP-C29L, the addition of 2 μM Zn-HPT could lead to partial rescue of the membrane repair capacity of the GFP-C105S mutant (e.g. movement toward the injury site, (FIG. 50b, right panel). GFP-C29L/C105S double mutant expressed in C2C12 cells is completely defective in repair of acute membrane damage, under conditions with nominal free zinc or following addition of 2 μM Zn-HPT (FIG. 50c). Single mutation of the RING motif (C29L), or the B-box motif (C105S) led to significant defects in membrane repair capacity in an extracellular solution with nominal free zinc (FIG. 51). The addition of Zn-HPT ionophore could partially restore the membrane repair capacity of these single cysteine mutants. The membrane repair function of the C29L/C105S double mutant is completely lost, and is independent of the movement of zinc across the plasma membrane. Data with other mutants of MG53 are summarized in Table 1. Overall, these results suggest that zinc-binding to the RING and B-box motifs of MG53 plays an important role in the intracellular vesicle translocation process associated with repair of membrane damage.

TABLE 1

Characteristics of MG53 mutants.

| Mutations | Oligomerization | Zinc-binding | Membrane Repair (−Zn-HPT) | Membrane Repair (+Zn-HPT) |
|---|---|---|---|---|
| WT | + | + | + | + |
| C29L | + | − | − | + |
| H31A | + | − | − | + |
| C29L/C105S | + | − | − | − |
| C105S | + | − | − | + |
| C242A | − | N/A | − | − |
| C53, 55, 56A | + | N/A | + | + |
| C86A | + | N/A | − | + |

MG53 can bind Zn through a RING motif. MG53 contains a canonical TRIM domain that contains a Zn binding motif (Ring) and a Bbox motif (FIG. 23a). Bacterial culture was lysed by sonication, centrifuged and bind to Amylose resin in column buffer containing 10 uM zinc for overnight at 4 degree (FIG. 23b). Then the resin was washed by zinc free column buffer following by 50 ml of zinc free column buffer with 0.3 mM maltose. Protein levels and stability were confirmed by SDS-PAGE gel as shown. Lane 1 (Marker), Lane 2 (mMG53), Lane 3 (mC29L-MG53 mutant), Lane 4 (mC29L/C105S double mutant DM clone1) Lane 5 (mC29L/C105S double mutant DM clone2), Lane 6 (10 mg/ml BSA), Lane 7 (5 mg/ml BSA), Lane 8 (2.5 mg/ml BSA), Lane 9 (1 mg/ml BSA). The proteins on beads were first tested for the presence of free zinc in the solution (from 0.01 to 0.1 uM or ND depending on the preparation) (FIG. 23c). The beads (aliquot) were stained with a zinc-specific probe TSQ and fluorescence was observed under the fluorescent microscope and relative fluorescence intensity taken. Then the proteins were denatured at 56 C for 5 min, vortexed, centrifuged, and the measurements were taken again from the solution. The assay uses TSQ (Mol Probe) and an atomic standard solution of zinc (Sigma) for calibration. Chart indicates the amount of Zn binding to recombinant wild type (WT) MG53, C29L mutant (C29L) and double mutant (DM). Both mutants are located in the Ring motif of the TRIM domain. Data presented as mean±S.D. *$P<0.05$, **$P<0.001$ compared to wt; n=4~5.

Disruption of Zn-binding to MG53 correlates with defects in MG53-mediated repair of acute membrane damage. To directly monitor the participation of zinc in membrane repair, FDB muscle fibers isolated from the wild type mice were loaded with 2 μM TSQ, a specific fluorescent indicator for zinc in the intracellular solution (lower panels) (FIG. 24). A strong UV-laser was used to cause local damage to the FDB muscle fiber, as reflected by the accumulation of FM4-64 fluorescent day at the local injury site (top panels). Notice that significant elevation of TSQ fluorescence (and therefore more zinc) was observed at the acute injury site.

Production of recombinant MG53 protein by secretion from cultured cells. Our previous methodology used E. coli bacteria to produce recombinant protein at levels for experimental use. These bench-level preparations provided the initial reagent for our biochemical and in vitro cell culture assays. To improve the yield and purity of the hMG53 preparation, we plan to optimize the purification protocol by adding an additional step to the Ni-column that involves immuno-affinity chromatography. Since our initial monoclonal antibody generated against the rabbit MG53 protein does not bind human MG53, we have recently generated a hybridoma that produces mAb against hMG53. This monoclonal antibody (mAb 4A3F6F2) is highly effective at detecting human (and mouse) MG53 protein on a Western blot (FIG. 25). This antibody should be very useful in generating an immune-affinity column to improve our protein purification. Protein purified from E. coli has two potential disadvantages, one is the possibility of contamination with endotoxin from bacteria, and the other is the chance that the lack of post-translational modifications, such as glycosylation and phosphorylation, in prokaryotes may prevent the recombinant protein from fully functioning. Thus, we have developed additional methodology for the production of recombinant MG53 from cultured mammalian cells. To achieve this, we have also adapted the methodology used for the generation of other commercial protein therapeutics, such as humanized monoclonal antibody for cancer treatment, which involve purification of secreted protein from culture media from engineered CHO cells. A signal-peptide at the amino-terminus of hGM53 allows export of the recombinant MG53 as a secretory protein. Western blot showed that abundant MG53 protein could be purified from conditioned media with CHO cells that are transiently transfected with the engineered hMG53 cDNA. This methodology was generally accepted by FDA. We are in the process of establishing stable CHO cell lines that express MG53 as a secretory product, to generate recombinant MG53 for broad use in treatment to protect against damage to the skin, heart and muscle cells.

Expression of recombinant MG53 can be performed in eukaryotic or prokaryotic cells. FIG. 26 illustrates that recombinant MG53 can be expressed in either eukaryotic or prokaryotic systems. Briefly, recombinant MG53 is expressed in Sf9 cells as a fusion protein containing both a TAT peptide portion and a six-histidine tag (6-HIS tag). This histidine tag can be used to isolate and purify recombinant protein using filtration chromatography techniques well known in the art. Panel (A) shows the Coomassie blue stained gel of recombinant human MG53 protein (arrow) fractions isolated from Sf9 cells with a Ni-NTA column Input=cell extract, FT=flow through, M=marker, E=elution number. (B) Coomassie blue stained gel of recombinant human TAT-MG53 (arrow) isolated from Sf9 cells. The Coomassie blue stained gel in (C) represents recombinant mouse TAT-MG53 (arrow) expressed and isolated from *E. coli*.

FIG. 27 Illustrates that a signal-peptide at the amino-terminus of hMG53 allows export of the recombinant MG53 as a secretory protein. Western blot shows that abundant MG53 protein could be purified from conditioned media with CHO cells that are transiently transfected with the engineered hMG53 cDNA.

Co-immuno-precipitation (Co-IP) experiments in HEK293 cells transfected with a Flag-MG53 fusion protein construct and a series of HA-MG53 fusion protein mutants. Co-IP was performed with an anti-Flag antibody on whole cell extracts followed by Western blot with an anti-HA antibody (FIG. 28a). The anti-Flag antibody can pull down wild type MG53 and all conserved cysteine residue MG53 mutants tagged with HA, indicating that MG53 proteins associate to form dimers and that this association is not dependent on oxidation of the cysteine residues. Co-IP experiments show that formation of MG53 dimers requires the presence of the coiled-coil domain (FIG. 28a). HEK293 cells were co-transfected with a HA-MG53 fusion protein construct and a series of GFP-MG53 fusion protein mutants, including a construct containing only the coiled-coil domain of MG53 linked to GFP (GFP-CC). An anti-HA antibody was used to Co-IP from whole cell extracts and the resulting proteins were analyzed by Western blot with an anti-GFP antibody.

Heterologous expression of MG53 in a human cell line results in membrane repair in response to acute injury. FIG. 29 demonstrates that recombinant MG53 can be expressed in a heterologous expression system and retain its ability to repair cell membrane damage without the expression of additional proteins. Specifically, MG53 was cloned into an expression vectors as a fusion protein with red fluorescent protein (RFP). The fusion protein was expressed in a human embryonic kidney cell line (HEK293 fibroblast cell line) and the cell's ability to repair membrane damage was compared to cells expressing only RFP. Panel (a) demonstrates that cell lines stably expressing an RFP (red fluorescent protein) control protein show a cytosolic expression pattern. However, in HEK293 cells expressing RFP only (FIG. 29a); injury with a microelectrode results in no translocation of RFP to the injury site (arrow). Some bleaching of RFP fluorescence occurs from excessive entry of extracellular buffer (*). In contrast, HEK293 cells that are stably expressing RFP-MG53 (FIG. 29c) show localization to intracellular vesicles. Microelectrode injury of HEK293 cells expressing RFP-MG53 (FIG. 29d) results in massive translocation of MG53 to the injury site (arrow) in less than 90 seconds. This result demonstrates that recombinant MG53 can be useful for repairing cellular and/or tissue damage in any cellular environment. Although recombinant MG53 is able to repair injury to cellular membranes when expressed in a heterologous system the invention is not so limited. In certain embodiments, the invention encompasses methods of co-expression of MG53 and caveolin-3 in order to promote membrane repair in order to treat or prevent tissue damage. In another embodiment, the present invention relates to a therapeutic composition comprising a TAT-MG53 polypeptide and a TAT-caveolin-3 polypeptide; or a MG53 and a caveolin-3 polypeptide either with of without another protein tag linked to either.

An active ingredient from *notoginseng* can facilitate MG53-membrane repair function. GFP-MG53 was expressed in C2C12 cells and then these cells were perfused with an alcohol extract from *notoginseng*. As can be seen in FIG. 30, application of this active ingredient can rapidly induce MG53 translocation to the plasma membrane within 2 min after perfusion. This rapid response was not observed with the carrier control, suggesting that *notoginseng* can potentially energize MG53 membrane repair function. Based on this observation, we reasoned that a therapeutic approach with the combination of MG53 and *notoginseng* may provide additive protective effects in preventing both inflammation and membrane damage to the cells, and thus can improve the function of MG53 when applied in tandem with recombinant MG53 protein or when applied alone as a supplement of pharmaceutical.

*Notoginseng* (*Panax notoginseng*) is an important component of traditional Chinese herbal medicines that has been widely used for treatment of a number of different disorders. Such herbal medicines frequently use the plant's root that is harvested after the fruit has ripened. The natural habitat of this herb is in southwest Asia, mainly in Yunnan Province of China. The importance in traditional medicine is emphasized in *Materia Medica* by Li Shi-zhen (1518-1593 AD), which refers to *notoginseng* as "more valuable than gold." The long history of *notoginseng* use at therapeutic doses emphasizes the proven safety and efficacy of this herbal compound.

*Notoginseng* has been particularly prized in wound treatment due to its ability to control both internal and external hemorrhaging (*J Nat Med.* 2006 60: 135). *Notoginseng* extracts can reduce bleeding time and improves hemostasis more effectively than placebo controls. Other studies have shown beneficial effects on cardiovascular system by decreasing blood pressure, improving blood supply and providing protection against shock. Many studies have also shown that *notoginseng* acts as a broad inhibitor of inflammation in a number of tissues. Due to these findings, *notoginseng* is increasingly the focus of research in complementary and alternative medicine (CAM). We have tested the effect of *notoginseng* on the membrane repair function of MG53. GFP-MG53 was expressed in C2C12 cells and then these cells were perfused with an alcohol extract from *notoginseng*. As can be seen in FIG. 30, application of this active ingredient can rapidly induce MG53 translocation to the plasma membrane within 2 min after perfusion. This rapid response was not observed with the carrier control, suggesting that *notoginseng* can potentially energize MG53 membrane repair function. Based on this observation, we reasoned that a therapeutic approach with the combination of MG53 and *notoginseng* may provide additive protective effects in preventing both inflammation and membrane damage to the cells, and thus can improve the function of MG53 when applied in tandem with recombinant MG53 protein or when applied alone as a supplement of pharmaceutical.

Patching of plasma membrane by external application of MG53. The therapeutic use of recombinant MG53 as a tissue repair reagent is demonstrated in FIG. 31. Our previous experiments shown that MG53 expressed within a cell can increase resistance to cellular damage, however we have not shown that protein applied externally can reseal the plasma membrane following damage. To establish if this is the case, we isolated RFP-MG53 (a MG53 fusion protein that contains a red fluorescent protein) expressed in HEK293 cells and applied this protein extract to the external media surrounding C2C12 myoblasts in culture. Cells were mechanically wounded with a microelectrode while the localization of the fusion protein was observed by confocal microscopy. There was clear accumulation of RFP-MG53 at injury sites where resealing took place (FIG. 31). These results indicate that MG53 protein can be applied externally to cells and remain effective at resealing the damaged membrane. This finding has significant consequences for the application of MG53 as a therapeutic protein. By simply providing the protein outside the cell at the time of damage, MG53 can facilitate resealing of the membrane and prevent cellular damage. Such an approach will significantly simplify the formulation of MG53 into an effective therapeutic compound.

Genetic overexpression of MG53 can prevent membrane damage. Human embryonic kidney (HEK293) cells were transfected with RFP-MG53 or RFP and then electroporated with fields of varying strength (FIG. 32). The amount of membrane damage was measured by assessing the amount of lactate dehydrogenase (LDH) that leaks into the extracellular media out of holes in the plasma membrane produced by electroporation. The more damage that occurs to the membrane, the higher the reading on the LDH assay will be. We observed that HEK293 cells transfected with RFP-MG53 can reseal their membranes more effectively following electro-poration and prevent the leak of LDH into the extracellular solution. Thus, expression of exogenous MG53 in non-muscle cells can increase the capacity for cell membrane repair in such non-muscle cells.

Fluorescent dye entry can be used to measure membrane damage following electroporation. Human embryonic palatal mesenchymal (HEPM) cells ($1 \times 10^6$) were placed in a spinning cuvette of a PTI fluorescence system (FIG. 33). FM1-43 day was added outside of the cells and displayed minimal fluorescence with an excitation of 479 nm and an emission of 598 nm. When cells were electroporated with a field strength of 50 V/cm or 100 V/cm there was a dose dependent increase in fluorescence detected. Electroporation does not produce auto-fluorescence in cells where the dye is not present (control).

Fluorescent dye entry can be used to measure membrane damage following mechanical damage. Human embryonic palatal mesenchymal (HEPM) cells ($1 \times 10^6$) were placed in a spinning cuvette of a PTI fluorescence system (FIG. 34). FM1-43 day was added outside of the cells and displayed minimal fluorescence with an excitation of 479 nm and an emission of 598 nm. Cells were removed from the cuvette (Pour) sheared with a 28 gauge needle (Shear), leading to an increase in FM1-43 fluorescence. Mechanical shear stress does not produce auto-fluorescence in cells where the dye is not present (control).

Recombinant MG53 can protect kidney cells from cell membrane damage. (a) HEK293 cells ($8 \times 10^4$) were treated with 10 ug/mL recombinant human MG53 or vehicle control and then electroporated at various field strengths (FIG. 35). Extracellular recombinant MG53 can prevent damage from electroporation. (b) MG53 or a vehicle control was added to recombinant LDH to generate standard curves for LDH activity. Since MG53 does not affect the LDH reactions the LDH assay is valid for measuring membrane damage under these conditions.

Recombinant MG53 can protect gum lining cells from cell membrane damage. (a) HEPM cells ($5 \times 10^4$) were treated with 10 ug/mL recombinant human MG53 or vehicle control and then electroporated at various field strengths (FIG. 36). Extracellular recombinant MG53 can prevent damage from electroporation. (b) MG53 or a vehicle control was added to recombinant LDH to generate standard curves for LDH activity. Since MG53 does not affect the LDH reactions the LDH assay is valid for measuring membrane damage under these conditions.

Recombinant MG53 can protect kidney cells from mechanical cell membrane damage. HEK293 cells ($8 \times 10^4$) were treated with glass microbeads to induce mechanical damage (FIG. 37). Different does of recombinant human MG53 or vehicle control was applied to the samples when glass beads were added to the media. Cells were rotated on an orbital shaker and then the supernatant was analyzed for LDH levels. We find that MG53 can prevent mechanical membrane damage and that 10 ug/mL is likely a saturating dose of the protein.

Effects of MG53 are specific to the function of the protein. MG53 proved to be effective at resealing damage in Hela cervical epithelial cells that was produced due to exposure to glass beads (FIG. 38). When the recombinant protein is boiled the protein can no longer facilitate membrane resealing. This indicates that the resealing activity is specific to the function of the MG53 protein that depends on the proper conformation of the protein.

Membrane damage to human keratinocytes induced by nitrogen mustard can be prevented by MG53. Various doses of nitrogen mustard, a skin blistering agent, can produce LDH release from primary human keratinocytes (FIG. 39). Some of this damage can be prevented by the application of recombinant protein after exposure and removal of the nitrogen mustard. Inset picture illustrates the effects of exposure to a skin blistering agent.

Figure 41:
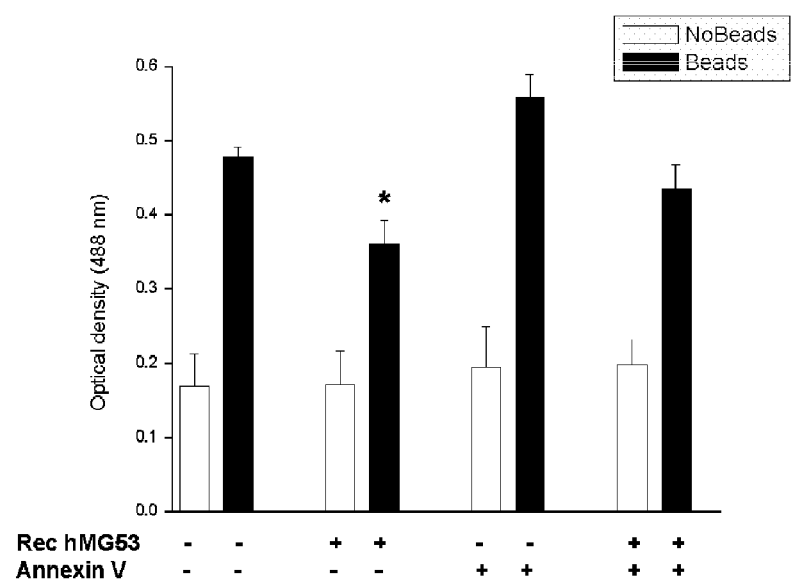
Figure 42:
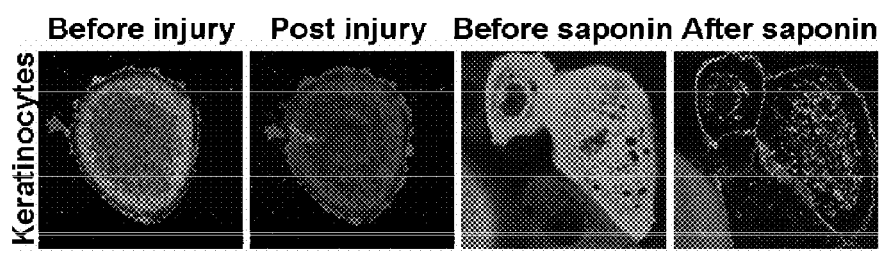

Externally applied recombinant MG53 requires phosphatidylserine (PS) binding to reseal damaged membranes. HEK293 cells were treated with recombinant human MG53 or vehicle and them damaged by shaking in the presence of glass microbeads (black bars) (FIG. 40). Membrane damage is measured by LDH release from cells that is recorded by colormetric assay recorded at 488 nm. Simultaneous treatment of cells with phosphatidylserine (PS) can prevent resealing of plasma membrane. Thus, MG53 must be able to bind exposed PS on damaged cells in order to facilitate membrane repair. * $p<0.05$ Competition with another phosphatidylserine (PS) binding protein reveals externally applied recombinant MG53 requires PS binding to reseal damaged membranes. HEK293 cells were treated with recombinant human MG53 or vehicle and them damaged by shaking in the presence of glass microbeads (black bars) (FIG. 41). Membrane damage is measured by LDH release from cells that is recorded by colormetric assay recorded at 488 nm. Simultaneous treatment of cells with an excess (5:1) of a phosphatidylserine (PS) binding protein, Annexin V, can prevent resealing of plasma membrane. Thus, MG53 must be able to bind exposed PS on damaged cells in order to facilitate membrane repair. * $p<0.05$ MG53 can patch the plasma membrane in many different human cell types and prevent cell death. To test if exogenous MG53 can recapitulate membrane resealing function in non-muscle cell types, we used either adenovirus or liposome-based transfection methods to express GFP-MG53 in a number of different cell types. In all cell types tested, MG53 performed in a similar fashion as that seen in muscle cells. Here we illustrate these effects in immortalized human cell lines, including HEK293 (not shown) and human embryonic palatal mesenchymal (HEPM) dental cells (FIG. 43), as well as primary cultures of human keratinocytes (FIG. 42). Not only does GFP-MG53 localize properly in these cell types, it also effectively translocates to the plasma membrane following membrane damage by either physical penetration of a microelectrode or treatment with saponin detergent. The function of MG53 appears to be essential to allow membrane patching and survival of muscle cells following injury. Thus, providing MG53 in different cell types can recapitulate MG53 function in membrane resealing, indicating that MG53 has therapeutic potential for many different tissues beyond the musculoskeletal and cardiovascular system.

Lipopolysaccharides can induce membrane damage in HEPM cells that can be prevented by exposure to MG53. When HEPM cells are treated with LPS (1 mg/mL) for 24 hours LDH release can be observed, suggesting that membrane damage has occurred (FIG. 44). Application of MG53 can prevent the normal levels of LDH release from the HEPM cells, while co-incubation with LPS and MG53 shows normal release of LDH from cells. This suggests that MG53 can prevent damage to HEPM cells produced by LPS.

MG53 can translocate to membrane repair sites in gastric cells. Human gastric adenocarcinoma (AGS) cells were transfected with GFP-MG53 and then subjected to mechanical membrane damage by microelectrode needle penetration (top) or treatment with 0.005% saponin to permeabilize the membrane (bottom) (FIG. 45). Translocation of GFP-MG53 to the injury site (arrow) was monitored by live cell confocal microscopy. In both cases, cell membrane damage resulted in the translocation of MG53 to the plasma membrane.

MG53 can translocate to membrane repair sites in neural cells. Mouse primary astrocytes were transfected with GFP-MG53 and then subjected to mechanical membrane damage by microelectrode needle penetration (top) or treatment with 0.005% saponin to permeabilize the membrane (bottom) (FIG. 46). Translocation of GFP-MG53 to the injury site (arrow) was monitored by live cell confocal microscopy. In both cases, cell membrane damage resulted in the translocation of MG53 to the plasma membrane.

MG53 can translocate to membrane repair sites in airway epithelial cells. Human C38 airway epithelial cells were transfected with GFP-MG53 and then subjected to mechanical membrane damage by microelectrode needle penetration (top) or treatment with 0.005% saponin to permeabilize the membrane (bottom) (FIG. 47). Translocation of GFP-MG53 to the injury site (arrow) was monitored by live cell confocal microscopy. In both cases, cell membrane damage resulted in the translocation of MG53 to the plasma membrane.

Figure 49:
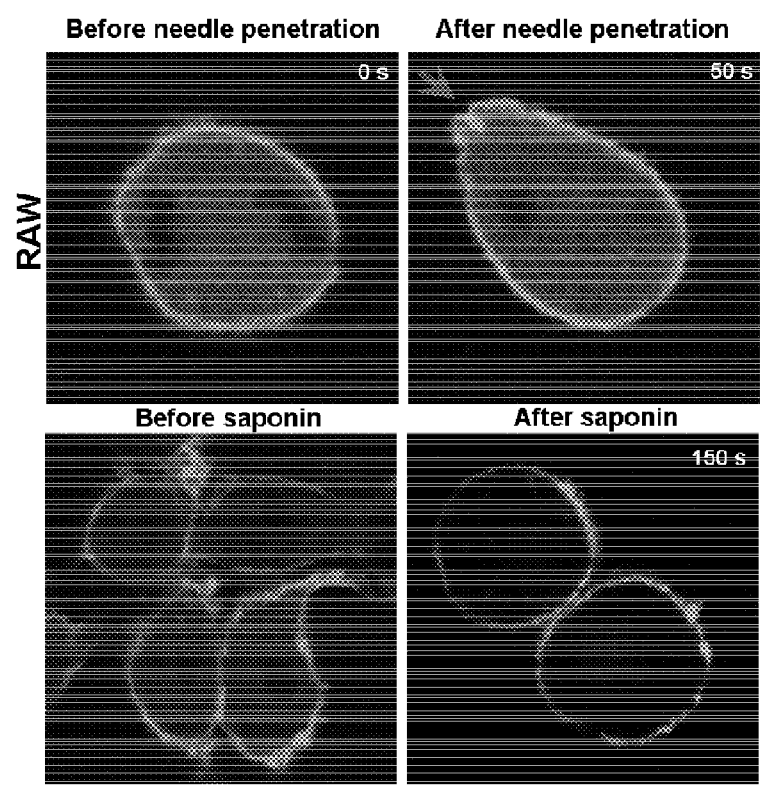

External MG53 can reseal to membrane damage in airway epithelial cells. Human IB3 airway epithelial cells were treated with external recombinant human MG53 or vehicle control and then exposed to mechanical membrane damage by glass beads (FIG. 48). Membrane damage is measured by LDH release from cells that is recorded by colormetric assay recorded at 488 nm MG53 could prevent cell membrane damage due to mechanical damage. * $p<0.05$ MG53 can translocate to membrane repair sites in immune cells. Mouse leukaemic monocyte macrophage (RAW 264.7) cells were transfected with GFP-MG53 and then subjected to mechanical membrane damage by microelectrode needle penetration (top) or treatment with 0.005% saponin to permeabilize the membrane (bottom) (FIG. 49). Translocation of GFP-MG53 to the injury site (arrow) was monitored by live cell confocal microscopy. In both cases, cell membrane damage resulted in the translocation of MG53 to the plasma membrane.

FIG. 50 illustrates the inventors' current hypothesis on the mechanism of membrane repair mediated by MG53. While not being limited to any particular theory, experimental evidence indicates that MG53 is likely localized to the inner surface of the plasma membrane due to its association with phosphatidylserine-containing vesicles. Under normal conditions MG53 is likely monomeric and sequestered proximal to the membrane surface due to associations with other proteins. Following damage to the cellular membrane MG53, which is normally in its reduced form, is exposed to a localized oxidative environment which triggers the formation of disulfide cross-bridges and intermolecular MG53 oligomerization. The oligomerization of MG53 brings phosphatidylserine-containing vesicles together at the damage site.

These studies demonstrate that MG53 is a critical component of the cell membrane repair machinery, as illustrated by the significant deficiency in membrane repair function of the mg53−/− muscle. The response of MG53-mediated membrane patching is rapid, occurring on the order of seconds after injury, therefore MG53 appears to mediate acute repair processes. For MG53 to function in membrane repair it must oligomerize, a process that depends on oxidation of the protein rather than entry of extracellular $Ca^{2+}$. Extracellular $Ca^{2+}$ likely acts to facilitate the fusion of the vesicles after they have moved to the plasma membrane through the oxidation-activated translocation of MG53. Through interaction with PS, MG53 oligomerization provides a nucleation site for recruitment of intracellular vesicles to the injury site (FIG. 50). This two step process is essential for the maintenance of cellular integrity. Thus, modulation of the extracellular oxidation state surrounding a cell or the $Ca^{2+}$ available for membrane resealing would potentially constitute a methodology for improving the membrane repair capacity of a cell.

Exemplary Methods

Identification and cloning of MG53—The preparation and screening of a mAb library for microsomal proteins of rabbit skeletal muscle were described previously. The preparation of mAb5259 (IgG1 subclass) and immunoaffinity purification was carried out as described previously (21). Purified MG53 was subjected to amino acid sequence analysis and all sequences determined were encoded in the rabbit MG53 cDNA (data not shown). Homology searches in the databases found mouse and human MG53 using the rabbit partial amino acid sequences. An exon region of the mouse MG53 gene was amplified from mouse genomic DNA, and rabbit and mouse skeletal muscle libraries were screened using the $^{32}$P-labeled exon fragment to yield full-length cDNAs.

Immunohistochemical and Immunostaining analysis—Immunochemical analyses using mAb5259 were carried out as described previously Immunoelectron-microscopy using secondary antibody conjugated with 15 nm gold particles was conduced as described previously.

Cell culture—The C2C12 murine myoblast cell line used for all studies was purchased from the American Type Culture Collection (Manassas, Va.). Cells were grown in a humidified environment at 37° C. and 5% $CO_2$ in DMEM medium for C2C12 or Ham's F12 medium for CHO cells supplemented with 10% fetal bovine serum, 100 units/ml penicillin and 100 ug/ml streptomycin. In order to induce myotube differentiation, C2C12 myoblasts were grown to confluence and the medium was switched to DMEM containing 2% horse serum, penicillin (100 U/ml), streptomycin (100 μg/ml). For transient transfections, C2C12 myoblasts or CHO cells were plated at 70% confluence in glass-bottom dishes. After 24 hours, cells were transfected with plasmids described above using GeneJammer reagent (Stratagene). Cells were visualized by live cell confocal imaging at 24-48 hours after transfection or at times indicated for individual experiments. In some experiments, C2C12 myoblasts were allowed to differentiate into myotubes for the indicated time before observation.

Plasmids construction—The full-length mouse MG53 cDNA and associated truncation mutants were generated by PCR using the primers described in supplemental table 1. For construction of pCMS-MG53, after digestion by the appropriate restriction enzymes, the PCR-amplified cDNA was inserted into pCMS-EGFP vector (Invitrogen) at Nhe I/Xba I sites. For construct the GFP-MG53, GFP-TRIM, GFP-SPRY, MG53-GFP, TRIM-GFP and SPRY-GFP, PCR products were inserted into pEGFP-C1 at the XhoI/XbaI sites, or pEGFP-N1 at the XhoI/KpnI sites.

Live cell imaging—To monitor intracellular trafficking of GFP-MG53 either CHO or C2C12 cells were cultured in glass-bottom dishes (Bioptechs Inc.) and transfected with the plasmids described above. Fluorescence images (512× 512) were captured at 3.18 s/frame using a BioRad 2100 Radiance laser scanning confocal microscope with a 63×1.3NA oil immersion objective.

RNAi assay—The target sequence for shRNA knockdown of MG53 is at position 622-642 (GAG CTG TCA AGC CTG AAC TCT) in the mouse MG53 cDNA. For caveolin-3, the target sequence is at position 363-380 (GAC ATT CAC TGC AAG GAG ATA). Complementary sense and antisense oligonucleotides were synthesized. To construct the MG53 shRNA and control plasmids, annealed oligonucleotides were inserted into psiRNA-hH1GFPzeoG2 (InvivoGene) at the Acc 65I/Hind III restriction enzyme sites. For caveolin-3 shRNA and control plasmids, annealed oligonucleotides were inserted into pRNAiDsRed vector (BD Biosciences) at the EcoR I/BamH I restriction enzyme sites. Each vector has as independent fluorescent protein expression cassette (green or red) to act as markers of cell transfection. All plasmids were confirmed by direct sequencing with flanking primers and the down-regulation of MG53 and caveolin-3 protein expression was examined by Western blot analysis.

Western blot and Co-immunoprecipitation—Immunoblots were using standard techniques. Briefly, C2C12 or CHO cells were harvested and lysed with ice-cold modified RIPA buffer (150 mM NaCl, 5 mM EDTA, 1% NP40, 20 mM Tris-HCl, pH 7.5) in the presence of a cocktail of protease inhibitors (Sigma). 20 µg of total protein were separated on a 4-12% SDS-polyacrylamide gel. A standard protocol was used for co-immunoprecipitation studies of MG53 and interacting proteins, e.g., Caveolin-3. In brief, skeletal muscle tissue or C2C12 myotubes were lysed in 0.5 ml modified RIPA buffer. The whole cell lysate (500 µg) was incubated overnight with 5 µg polyclonal anti-MG53 (polyclonal antibody), or anti-caveolin-3 antibody (mAb). As a negative control, 500 µg whole cell lysate was incubated with 5 µg normal rabbit and mouse IgG and processed as described above. The immune complexes were collected on protein G-Sepharose beads by incubating for 2 hours and washed four times with RIPA buffer.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims.

The invention claimed is:

1. A composition comprising an effective amount of a mitsugumin53 (MG53) polypeptide sufficient to treat a tissue damage or injury related disease or disorder, wherein the MG53 polypeptide has at least 95% sequence identity to the amino acid sequence as set forth in SEQ ID NO. 1, a pharmaceutically acceptable carrier, and an agent capable of modulating, synergistically, the membrane repair activity of MG53 selected from the group consisting of a zinc ionophore, an oxidizing agent, and *notoginsing*.

2. The composition of claim 1, wherein the MG53 polypeptide is bound or complexed with at least one member selected from the group consisting of CSN6, kinesin, caveolin-3, periaxin, and myelin-basic-protein, wherein the complex facilitates cell membrane repair.

3. A method of treating a pathological condition related to cell membrane damage comprising administering to an individual an effective amount of the composition of claim 1 wherein the composition is effective in ameliorating the effects of the pathological condition.

4. The composition of claim 1, wherein the agent capable of modulating, synergistically, the membrane repair activity of MG53 is phosphotidylserine.

5. The composition of claim 1, wherein the agent capable of modulating, synergistically, the membrane repair activity of MG53 is *notoginsing*.

6. The composition of claim 1, wherein the agent capable of modulating, synergistically, the membrane repair activity of MG53 is an oxidizing agent.

7. A method of treating cell membrane damage comprising administering extracellularly the composition of claim 1, wherein the composition is effective in treating cell membrane damage.

8. The method of claim 7, wherein the composition comprises *notoginsing*.

9. The method of claim 7, wherein the composition comprises an oxidizing agent.

10. The method of claim 7, wherein the composition is administered to a cell in vitro.

11. The method of claim 7, wherein the composition is administered to a cell in vitro.

12. The method of claim 7, wherein the cell is at least one of a fibroblast cell, epithelial cell, ovary cell, kidney cell, neuronal cell, keratinocyte, dental cell, gastric cells, immune cells, skeletal muscle, cardiac muscle cell or combination thereof.

13. The method of claim 3, wherein the pathological condition is selected from the group consisting of muscle or vascular cell/tissue injury, tissue injury that occurs as a result of cardiovascular disease, myocardial infarction or rigorous physical activity, sports-related injuries, muscular dystrophy, cardiac ischemia, heart failure, aging degeneration, neurodegeneration, sepsis, bacterial infection, gingivitis, gum recession, periodontal disease, wrinkle protection, dermal abrasion, UV damage, nitrogen mustard (chemical blistering agents), ulcers, COPD, wound healing, geriatric medicine, anti-inflammatory, and any combination thereof.

14. The method of claim 13, wherein the composition comprises *notoginsing*.

15. The method of claim 13, wherein the composition comprises an oxidizing agent.

16. The method of claim 13, wherein the composition is administered in at least one form selected from the group consisting of a lotion, spray, gel, suave, liquid, paste, aerosol, powder, injectable, transdermal application.

17. The method of claim 16, wherein the form is adapted for topical administration.

* * * * *